US011229951B2

(12) United States Patent
Pecina et al.

(10) Patent No.: US 11,229,951 B2
(45) Date of Patent: Jan. 25, 2022

(54) MONOLITHIC PRECURSOR TEST COUPONS FOR TESTING MATERIAL PROPERTIES OF METAL-INJECTION-MOLDED COMPONENTS AND METHODS AND APPARATUSES FOR MAKING SUCH COUPONS

(71) Applicant: THE BOEING COMPANY, Chicago, IL (US)

(72) Inventors: Joseph A. Pecina, Lynnwood, WA (US); Gary M. Backhaus, Lake Stevens, WA (US)

(73) Assignee: The Boeing Company, Chicago, IL (US)

( * ) Notice: Subject to any disclaimer, the term of this patent is extended or adjusted under 35 U.S.C. 154(b) by 283 days.

(21) Appl. No.: 16/425,727

(22) Filed: May 29, 2019

(65) Prior Publication Data
US 2020/0376558 A1    Dec. 3, 2020

(51) Int. Cl.
*B22F 3/22* (2006.01)
*B22F 3/24* (2006.01)
(Continued)

(52) U.S. Cl.
CPC ............ *B22F 3/225* (2013.01); *B22D 17/005* (2013.01); *B22D 17/14* (2013.01);
(Continued)

(58) Field of Classification Search
CPC .............................. B22F 3/225; B22D 17/005
(Continued)

(56) References Cited

U.S. PATENT DOCUMENTS 141,006 A    7/1873 Larnee
626,634 A    6/1899 Rylands
(Continued)

FOREIGN PATENT DOCUMENTS

DE    363990 C    11/1922
DE    1292115 B    4/1969
(Continued)

OTHER PUBLICATIONS

Ti-2007, Science and Technology, Proceedings of the 11th World Conference on Titanium (JIMIC50 held at Kyoto International Converence Center, Kyoto, Japan, Jun. 3-7, 2007, vol. II (9 pgs.).
(Continued)

*Primary Examiner* — Coris Fung
*Assistant Examiner* — Danielle M. Carda
(74) *Attorney, Agent, or Firm* — Kwan & Olynick LLP

(57) ABSTRACT

A method of making a test coupon using a mold is provided. The mold defines a mold cavity that comprises a first-grip-portion cavity, a second-grip-portion cavity, an intermediate-portion cavity, interconnecting the first-grip-portion cavity and the second-grip-portion cavity, and runner cavities, directly interconnecting the first-grip-portion cavity and the second-grip-portion cavity and not directly connected to the intermediate-portion cavity. The method comprises injecting feedstock material, comprising a metal powder, into the mold cavity to form a monolithic precursor test coupon in the mold cavity, wherein the monolithic precursor test coupon comprises a first grip portion, a second grip portion, an intermediate portion, and runners. The method also comprises removing the runners from the monolithic precursor test coupon.

20 Claims, 28 Drawing Sheets

(51) Int. Cl.
    *G01N 33/20*     (2019.01)
    *B22F 5/00*     (2006.01)
    *B22D 17/14*     (2006.01)
    *B22D 17/00*     (2006.01)
    *B22D 17/20*     (2006.01)
    *B22D 29/00*     (2006.01)

(52) U.S. Cl.
    CPC ............ *B22D 17/2084* (2013.01); *B22F 3/24* (2013.01); *B22F 5/00* (2013.01); *G01N 33/20* (2013.01); *B22D 29/00* (2013.01); *B22F 2003/247* (2013.01)

(58) Field of Classification Search
    USPC .......................................................... 419/66
    See application file for complete search history.

(56) References Cited

U.S. PATENT DOCUMENTS

| | | |
|---|---|---|
| 780,451 A | 10/1903 | Strehlan |
| 782,081 A | 6/1904 | Stone |
| 1,206,884 A | 12/1916 | Morton |
| 1,361,215 A | 12/1920 | Williams |
| 1,484,023 A | 2/1924 | Willis |
| 1,691,688 A | 11/1928 | Wells |
| 1,715,844 A | 6/1929 | Kienzl |
| 1,923,416 A | 8/1933 | Blomgren |
| 2,145,091 A | 1/1939 | Mansfield |
| 2,727,438 A | 12/1955 | Ludwig |
| 2,785,593 A | 3/1957 | Wing |
| 3,146,677 A | 9/1964 | Kochar |
| 3,545,311 A | 12/1970 | Messer |
| 3,938,373 A | 2/1976 | Fletcher et al. |
| 4,408,785 A | 10/1983 | Legros et al. |
| 4,625,611 A | 12/1986 | Bauman |
| 4,686,751 A | 8/1987 | Gracey |
| 5,015,289 A | 5/1991 | Toda et al. |
| 5,475,914 A | 12/1995 | Bornhorst, Jr. et al. |
| 5,595,424 A | 1/1997 | Nakagawa |
| 5,677,494 A | 10/1997 | Keener et al. |
| 5,795,463 A | 8/1998 | Prokopowicz |
| 5,798,463 A | 8/1998 | Doudican et al. |
| 5,810,876 A | 9/1998 | Kelleher |
| 2004/0126196 A1 | 7/2004 | Burr et al. |
| 2006/0241517 A1 | 10/2006 | Fowler et al. |
| 2016/0067795 A1 | 3/2016 | Gurnavage |
| 2019/0015897 A1* | 1/2019 | Roth-Fagaraseanu ...................... B22F 1/025 |

FOREIGN PATENT DOCUMENTS

| | | |
|---|---|---|
| DE | 19935276 A1 | 2/2000 |
| KR | 1020060014828 A | 2/2006 |
| WO | 2011120066 A1 | 10/2011 |

OTHER PUBLICATIONS

Extended European Search Report re Application No. 20160063.2 dated Oct. 8, 2020; pp. 9.

* cited by examiner

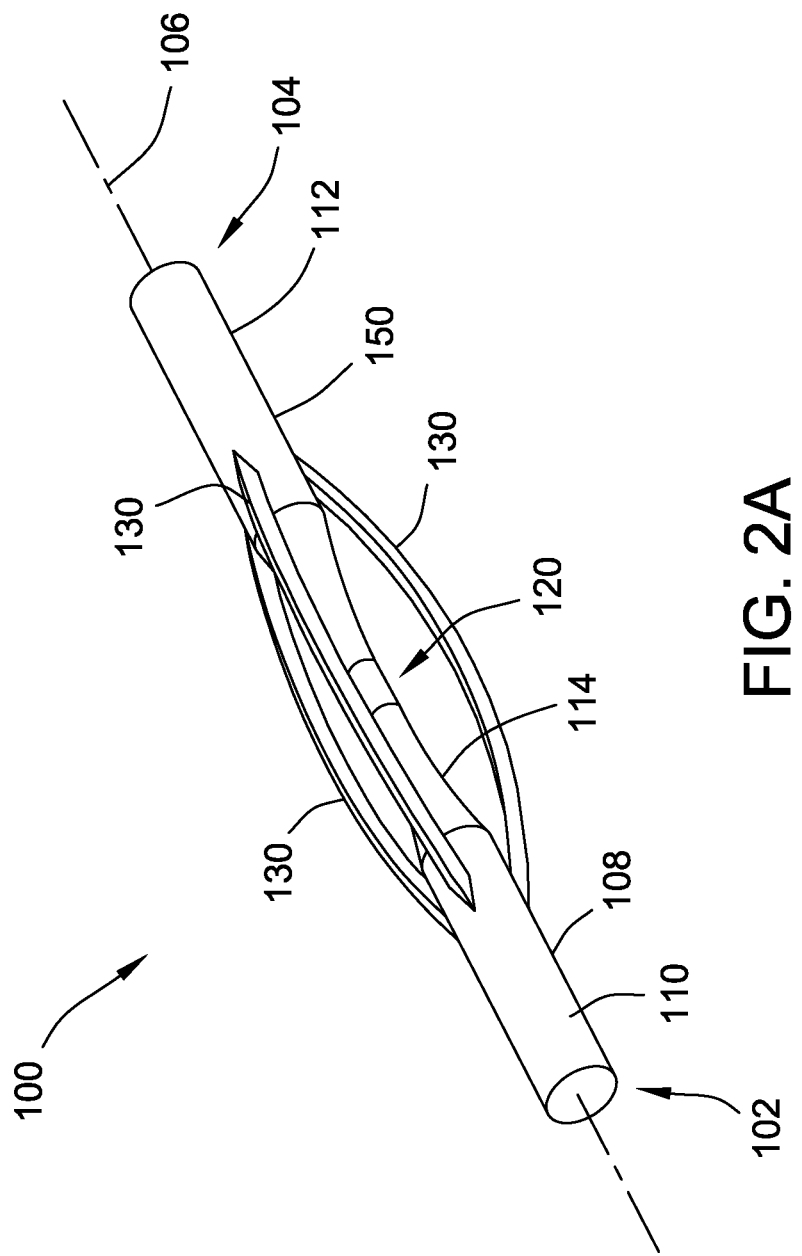

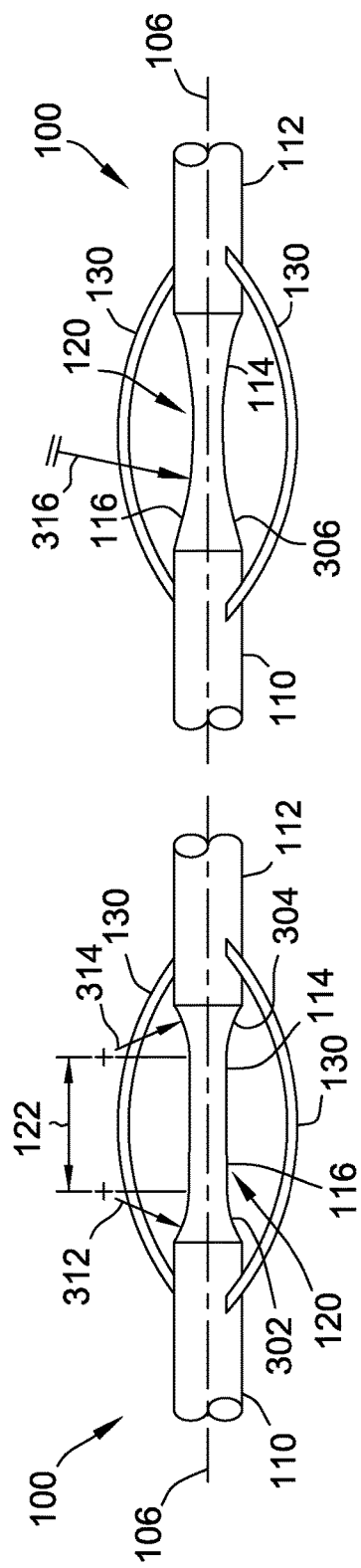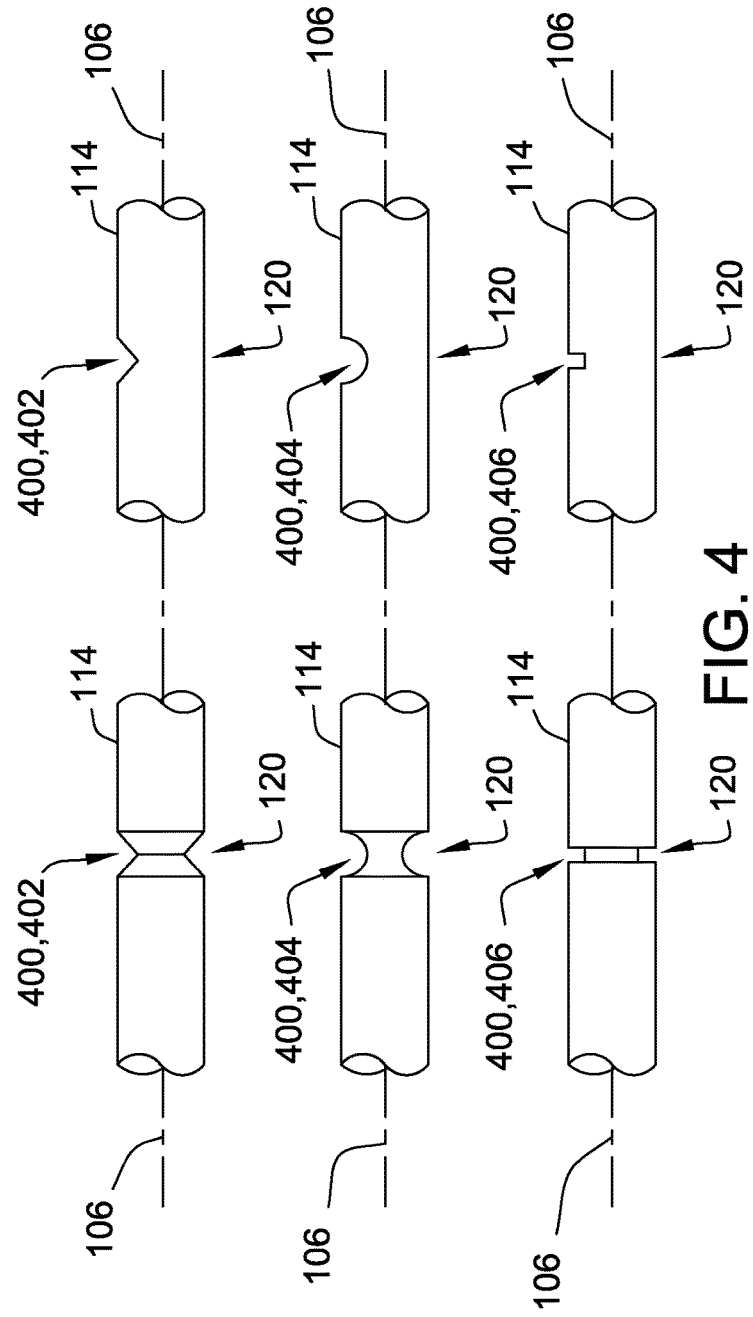

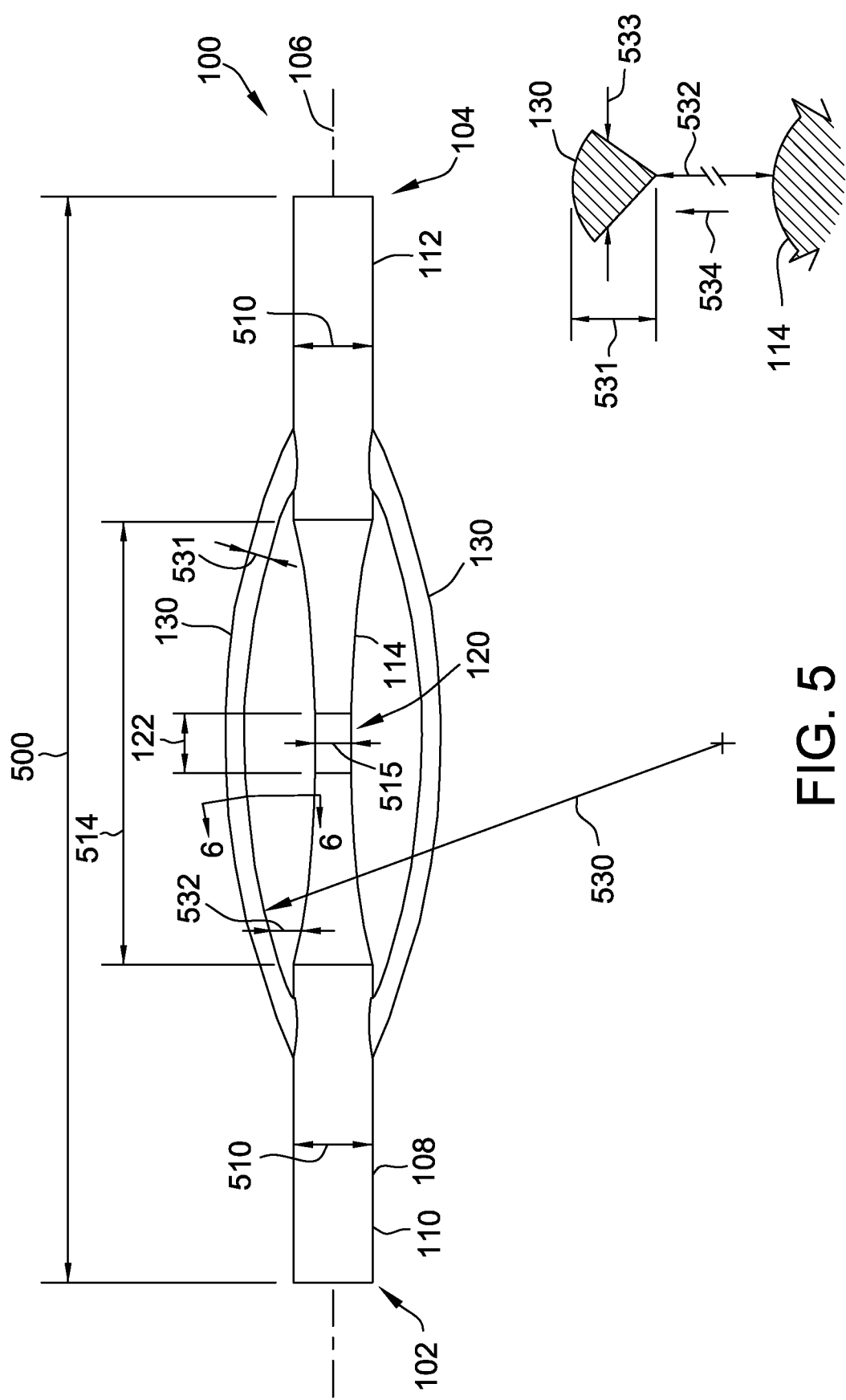

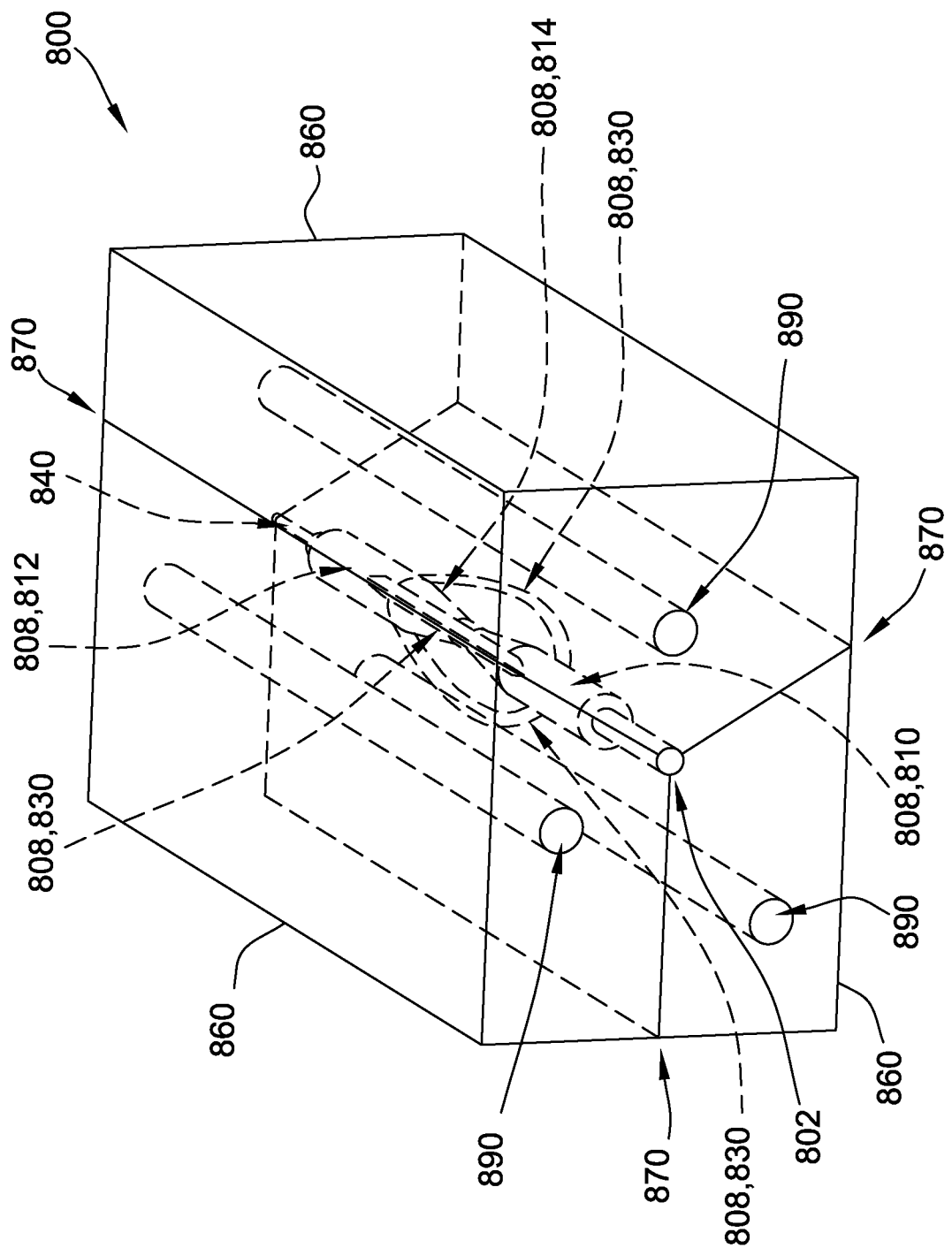

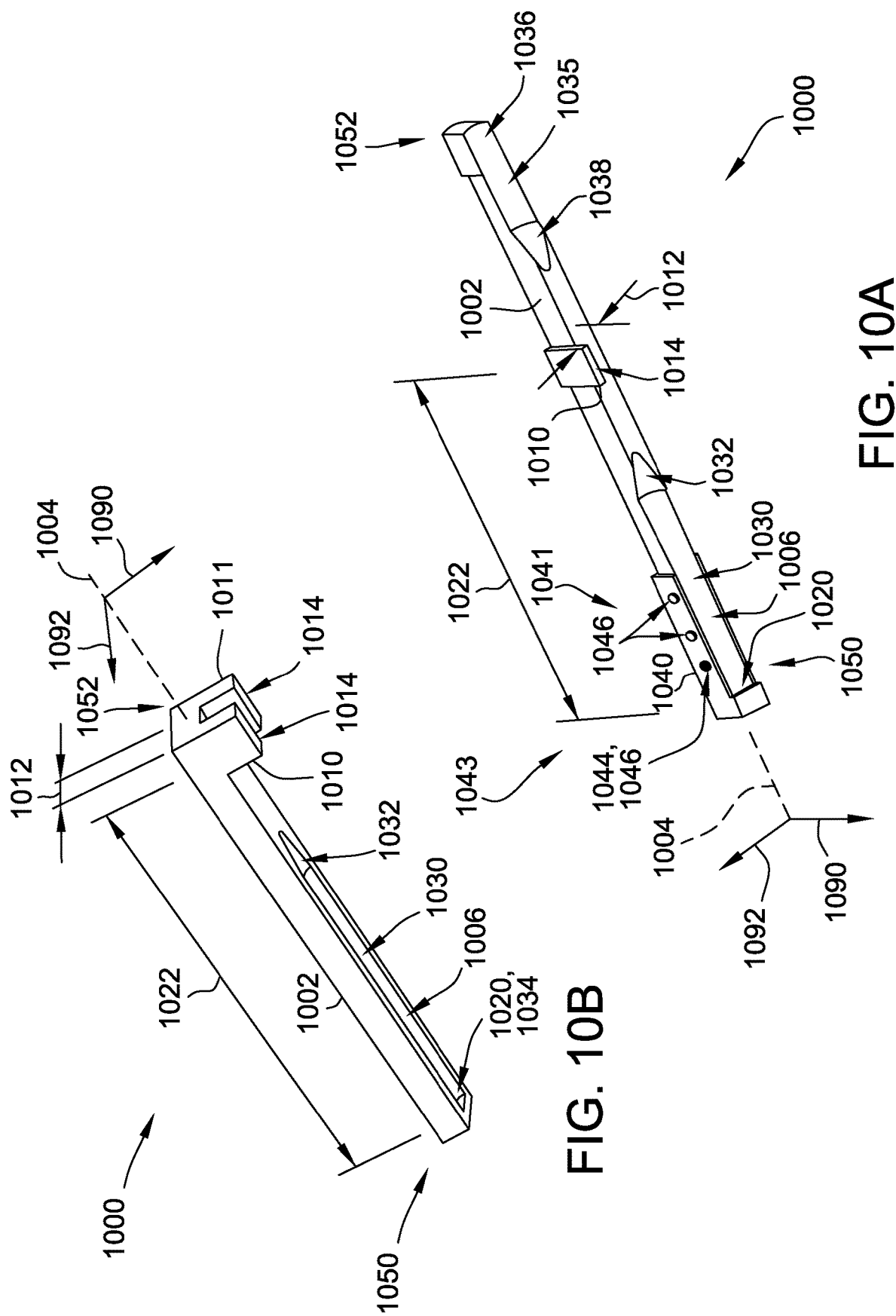

MONOLITHIC PRECURSOR TEST COUPONS FOR TESTING MATERIAL PROPERTIES OF METAL-INJECTION-MOLDED COMPONENTS AND METHODS AND APPARATUSES FOR MAKING SUCH COUPONS

TECHNICAL FIELD

The present disclosure relates to a monolithic precursor test coupon for testing material properties of metal-injection-molded components.

BACKGROUND

Components of various structures are manufactured using metal injection molding (MIM) techniques. MIM processes employ granular feedstock that includes powdered metal. Such feedstock is injected into a mold to form a green part, which is substantially geometrically similar to the final component, although the green part may be oversized relative to the final component to account for shrinkage during the subsequent sintering step. Next, the green part is subjected to de-binding, for example in a thermal or solvent-based process, to remove the binder and form a brown part. The brown part is then sintered at high temperatures to form the final, substantially metallic component.

It is often necessary and/or desirable to quantify certain material properties of MIM-manufactured components by testing coupons, formed in the same way and from the same materials as the components of interest. Such test coupons typically have a reduced central cross-sectional area and are sometimes referred to as "dog bone" coupons. When injecting feedstock through the mold during the MIM process to produce a test coupon, the reduced central cross-sectional area acts as a restriction that inhibits proper flow of the feedstock through the reduced-area section of the coupon. If feedstock injection pressure is increased to overcome the restriction, in some cases feedstock material is pushed through the restriction too quickly, shearing the binder away from the feedstock. If the binder is not uniformly distributed throughout the green test coupon after the injection-molding process is completed, the coupon may become warped during sintering. On the other hand, if the feedstock is pushed through the restriction too slowly, the binder cross-links before injection is completed, and the feedstock material tends to solidify, preventing further injection.

Due to the fact that green parts are relatively brittle, a long, narrow green part having a reduced-area central section may not survive typical mold-ejection techniques without damage. Mold-release agents are typically not used in MIM processes because of potential feedstock contamination problems. Accordingly, an increased number of ejector pins may be incorporated into the mold to provide better distribution of the ejection force, experienced by the green test coupon during the mold-release step, in an attempt to reduce the possibility of damaging the coupon as it is released from the mold. However, since the long, narrow shape and the reduced central cross-sectional area of the coupon require elevated injection pressures during the MIM processes, binder may flow into spaces between the ejector pins and the mold, causing the ejector pins to stick to the mold and become incapable of ejecting the coupon from the mold. Moreover, a long, narrow green part having a reduced-area central section, such as a green test coupon formed by an MIM process, as described above, may warp at the elevated temperatures, associated with sintering.

A green test coupon formed in an MIM process may also have undesirable "flash," i.e., ridges of excess material, formed by feedstock, seeping into the mold parting lines during the MIM process. Removal of flash from a long, narrow green part using conventional manual techniques introduces the risk of damaging the coupon.

SUMMARY

Accordingly, apparatuses and methods, intended to address at least the above-identified concerns, would find utility.

The following is a non-exhaustive list of examples, which may or may not be claimed, of the subject matter, disclosed herein.

Disclosed herein is a monolithic precursor test coupon that comprises a first grip portion, a second grip portion, and an intermediate portion, interconnecting the first grip portion and the second grip portion. The monolithic precursor test coupon also comprises runners, directly interconnecting the first grip portion and the second grip portion and not directly connected to the intermediate portion. The first grip portion, the second grip portion, the intermediate portion and the runners are composed of a substance that comprises metal powder and is in a green state.

The runners provide the monolithic precursor test coupon with increased stability and inhibit breakage or warping of the first grip portion, the second grip portion, and the intermediate portion during and after a process of forming the monolithic precursor test coupon, such as during one or more of: removal, in the green state, from a mold such as a metal injection molding (MIM) apparatus; de-binding; and sintering. In addition, because the runners interconnect the first grip portion and the second grip portion, and thus are not directly attached to the intermediate portion, removal of the runners during a process of forming a test coupon from the monolithic precursor test coupon poses a decreased risk of damage to the intermediate portion, facilitating accuracy in subsequent material property testing using the test coupon formed from the monolithic precursor test coupon.

Also disclosed herein is a metal-injection-molding (MIM) apparatus for making a monolithic precursor test coupon. The MIM apparatus comprises a mold, defining a mold cavity. The mold cavity comprises a first-grip-portion cavity and a second-grip-portion cavity. The mold cavity also comprises an intermediate-portion cavity, interconnecting the first-grip-portion cavity and the second-grip-portion cavity. The mold cavity further comprises runner cavities, directly interconnecting the first-grip-portion cavity and the second-grip-portion cavity and not directly connected to the intermediate-portion cavity. The MIM apparatus additionally comprises an injector that is operable to inject feedstock material, comprising a metal powder, into the mold cavity to form the monolithic precursor test coupon.

The MIM apparatus enables homogeneous distribution of the feedstock material within the first-grip-portion cavity, the intermediate-portion cavity, and the second-grip-portion cavity to facilitate formation of the monolithic precursor test coupon in the mold with reduced or eliminated voids, and further with reduced or eliminated shearing of a binder that is included in the feedstock material along with the metal powder. More specifically, the runner cavities enable a portion of the feedstock material to bypass a flow restriction caused by the intermediate-portion cavity and provide backfill of downstream portions of the monolithic precursor test coupon. The bypass flow area provided by the runner cavities thus enables formation of the monolithic precursor test coupon having a proper distribution and integrity of the feedstock material at an injection rate that avoids problems of binder shearing or premature binder cross-linking.

Additionally disclosed herein is a flash-removal tool that comprises a tool body, extending along a longitudinal tool axis. The flash-removal tool also comprises a tooth, projecting from the tool body in a first direction. The flash-removal tool further comprises an engagement surface, located a preselected distance away from the tooth along the longitudinal tool axis and perpendicular to the longitudinal tool axis. The tooth comprises a shearing surface, facing in the first direction and located an offset distance away from the longitudinal tool axis in a second direction. The first direction and the second direction are orthogonal to each other and define a plane, perpendicular to the longitudinal tool axis.

The engagement surface being spaced apart from the tooth by the preselected distance enables the tooth to align longitudinally with the gauge portion when the engagement surface engages the monolithic precursor test coupon. Moreover, the tooth projecting from the tool body in the first direction and having the shearing surface spaced at the offset in the second direction enables the tooth to slide between runners of the monolithic precursor test coupon such that the shearing surface aligns precisely with the flash on a gauge portion of the monolithic precursor test coupon. Thus, the flash-removal tool facilitates removal of the flash from the gauge portion, while the runners are still attached to the monolithic precursor test coupon, without requiring complex alignment procedures or adjustments.

Further disclosed herein is a method of making a test coupon using a mold. The mold defines a mold cavity that comprises a first-grip-portion cavity, a second-grip-portion cavity, and an intermediate-portion cavity, interconnecting the first-grip-portion cavity and the second-grip-portion cavity. The mold cavity further comprises runner cavities, directly interconnecting the first-grip-portion cavity and the second-grip-portion cavity and not directly connected to the intermediate-portion cavity. The method comprises injecting feedstock material, comprising a metal powder, into the mold cavity to form the monolithic precursor test coupon in the mold cavity. The monolithic precursor test coupon comprises a first grip portion, having a shape complementary to that of the first-grip-portion cavity, and the second grip portion, having a shape complementary to that of the second-grip-portion cavity. The monolithic precursor test coupon also comprises an intermediate portion, having a shape, complementary to that of the intermediate-portion cavity, and runners, each having a shape complementary to that of a corresponding one of the runner cavities. The method also comprises removing the runners from the monolithic precursor test coupon.

The method enables homogeneous distribution of the feedstock material within the first-grip-portion cavity, the intermediate-portion cavity, and the second-grip-portion cavity to facilitate formation of the monolithic precursor test coupon in the mold with reduced or eliminated voids, and further with reduced or eliminated shearing of a binder that is included in the feedstock material along with the metal powder. More specifically, the runner cavities enable a portion of the feedstock material to bypass a flow restriction caused by the intermediate-portion cavity and provide backfill of downstream portions of the monolithic precursor test coupon. The bypass flow area provided by the runner cavities thus enables the formation of the monolithic precursor test coupon having a proper distribution and integrity of the feedstock material at an injection rate that avoids problems of binder shearing or premature binder cross-linking. Removal of the runners from the monolithic precursor test coupon leaves the first grip portion, the intermediate portion, and the second grip portion of a test coupon for material property testing, such as in a tensile-test machine.

Also disclosed herein is a method of removing flash from a gauge portion of a monolithic precursor test coupon using a flash-removal tool. The flash-removal tool comprises a tool body, extending along a longitudinal tool axis. The flash-removal tool also comprises a tooth and an engagement surface, spaced apart from the tooth along the longitudinal tool axis. The tooth projects from the tool body in a first direction and comprises a shearing surface, facing in the first direction and located an offset distance away from the longitudinal tool axis in a second direction. The first direction and the second direction are orthogonal to each other and define a plane, perpendicular to the longitudinal tool axis. The method comprises coupling the engagement surface of the flash-removal tool against a first precursor-coupon end of the monolithic precursor test coupon. The method also comprises orienting the longitudinal tool axis parallel to a longitudinal symmetry axis of the monolithic precursor test coupon, wherein the shearing surface registers longitudinally.

The tooth projecting from the tool body in the first direction and having the shearing surface spaced at the offset in the second direction, such that the shearing surface registers longitudinally with the flash when the engagement surface of the flash-removal tool couples against the first precursor-coupon end and the longitudinal tool axis is oriented parallel to the longitudinal symmetry axis of the monolithic precursor test coupon, facilitates removal of the flash from the gauge portion at an increased speed, without requiring complex alignment procedures or adjustments.

BRIEF DESCRIPTION OF THE DRAWINGS

Figure 1A:
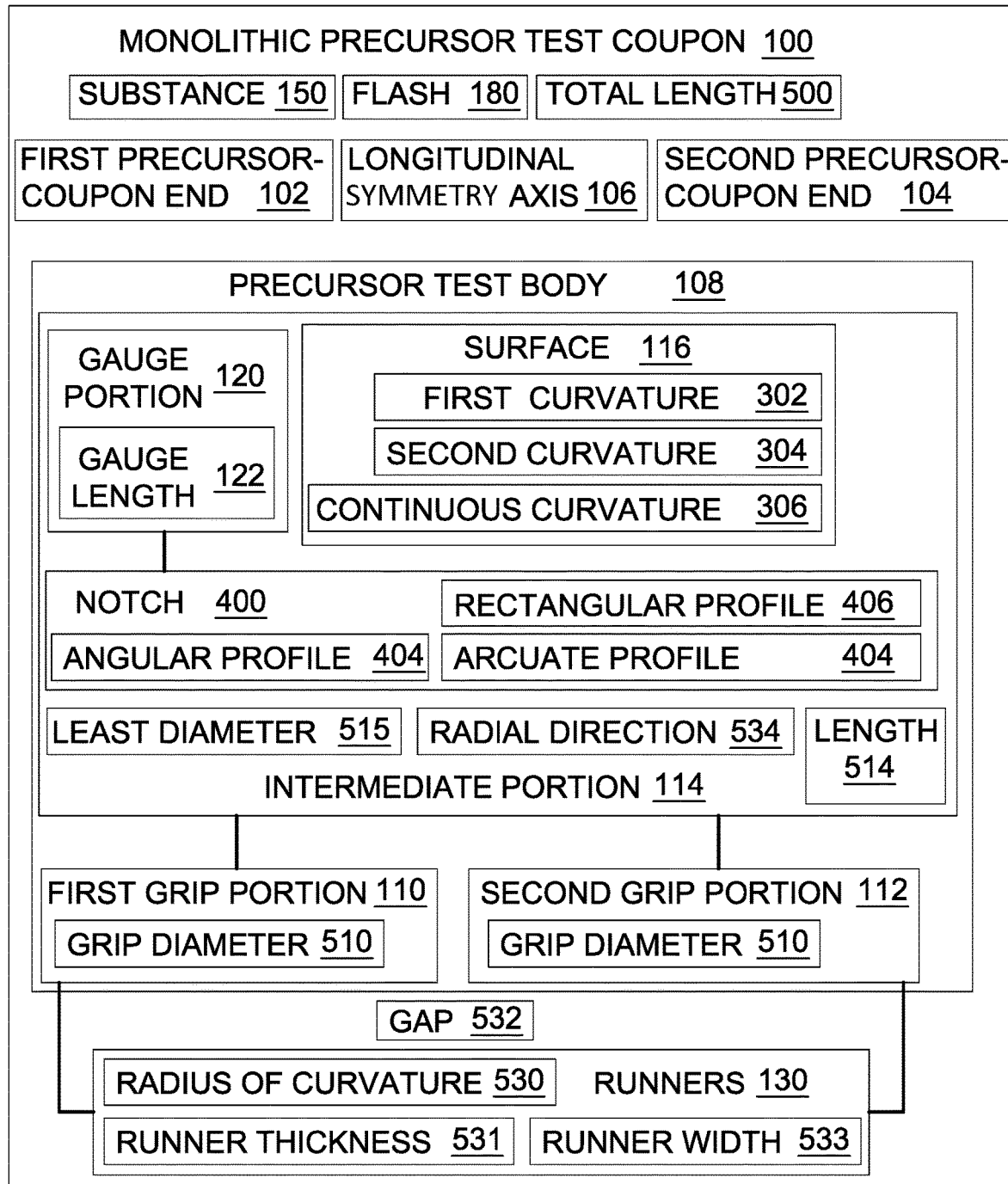
Figure 1B:
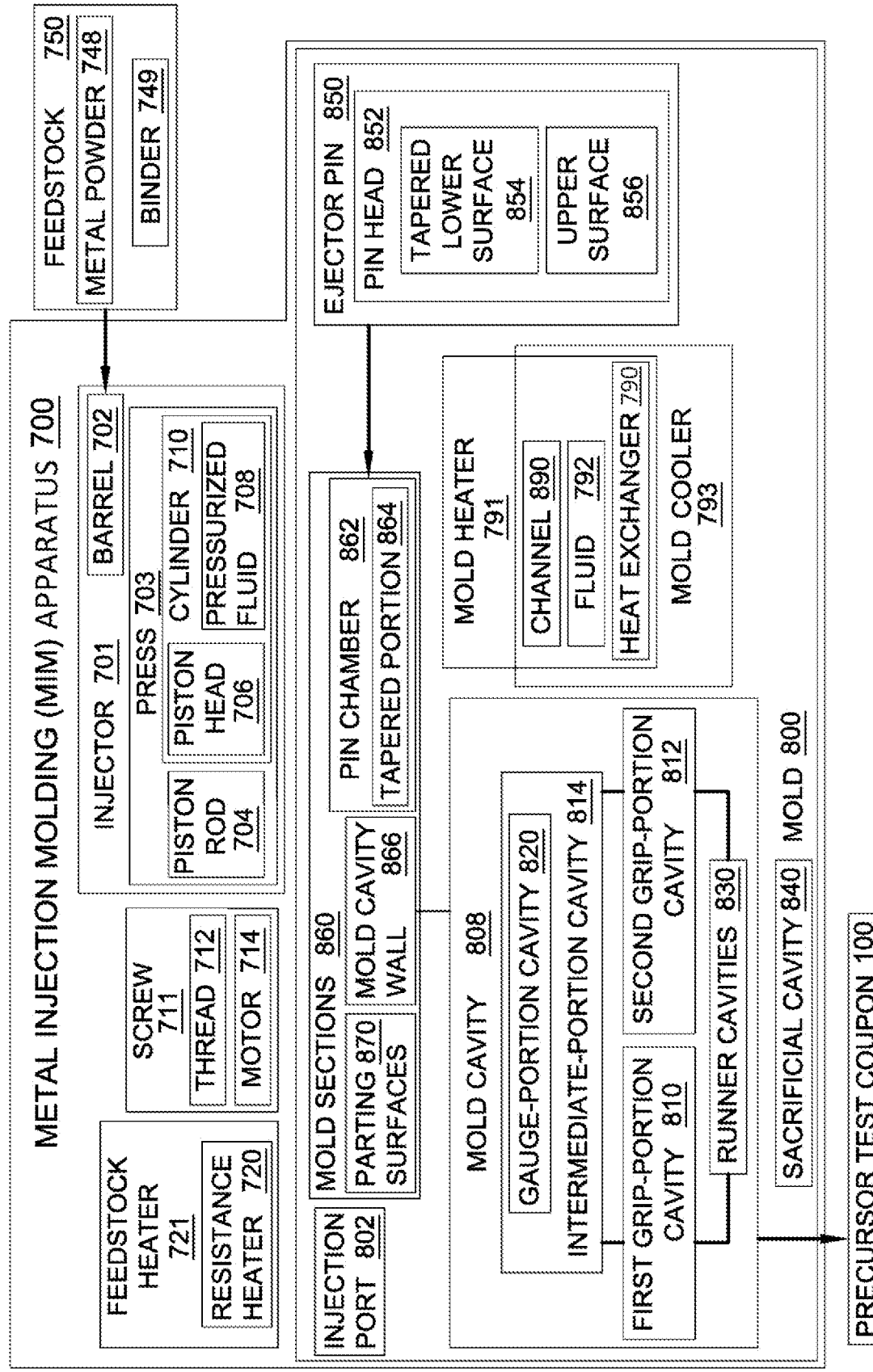
Figure 1C:
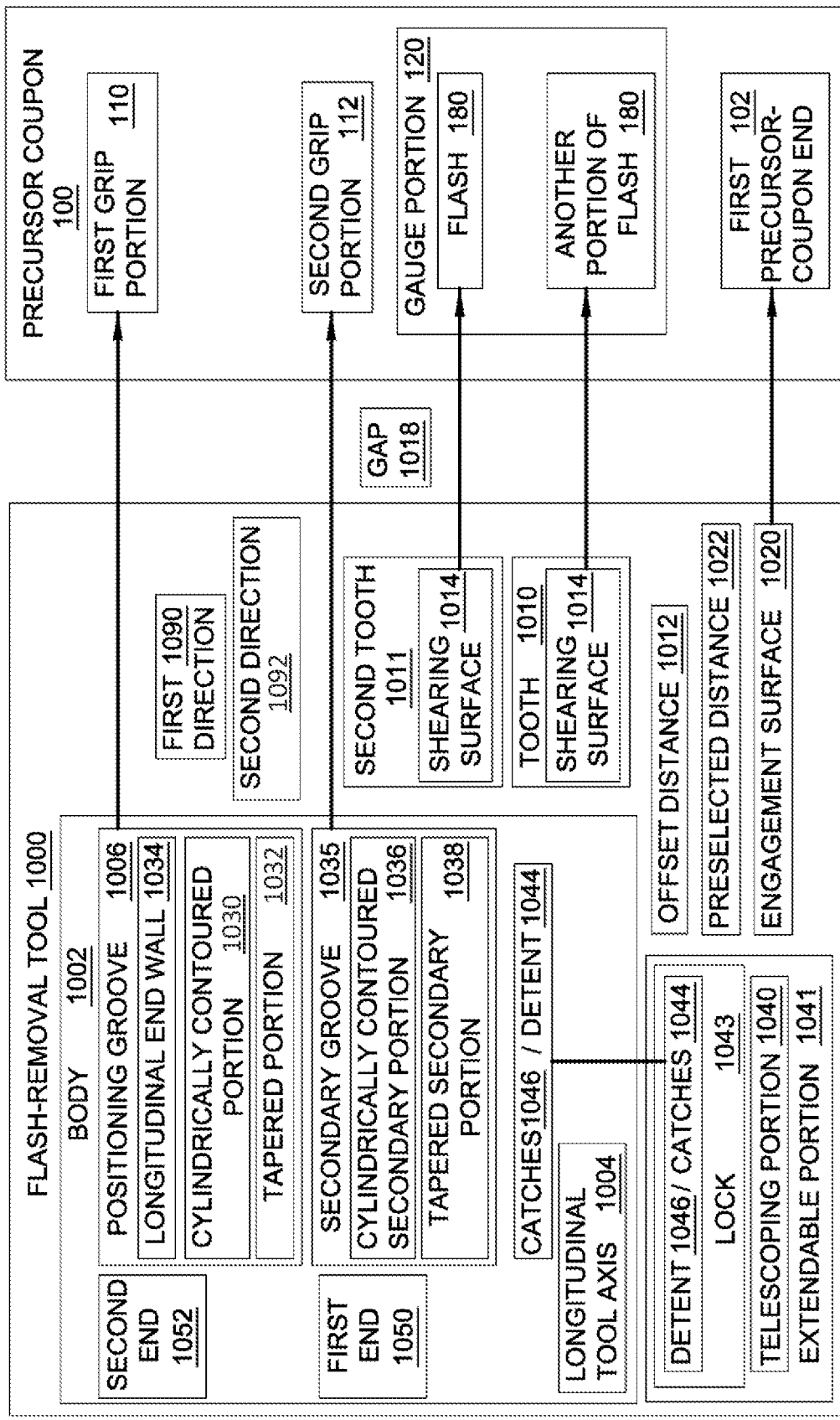
Figure 2B:
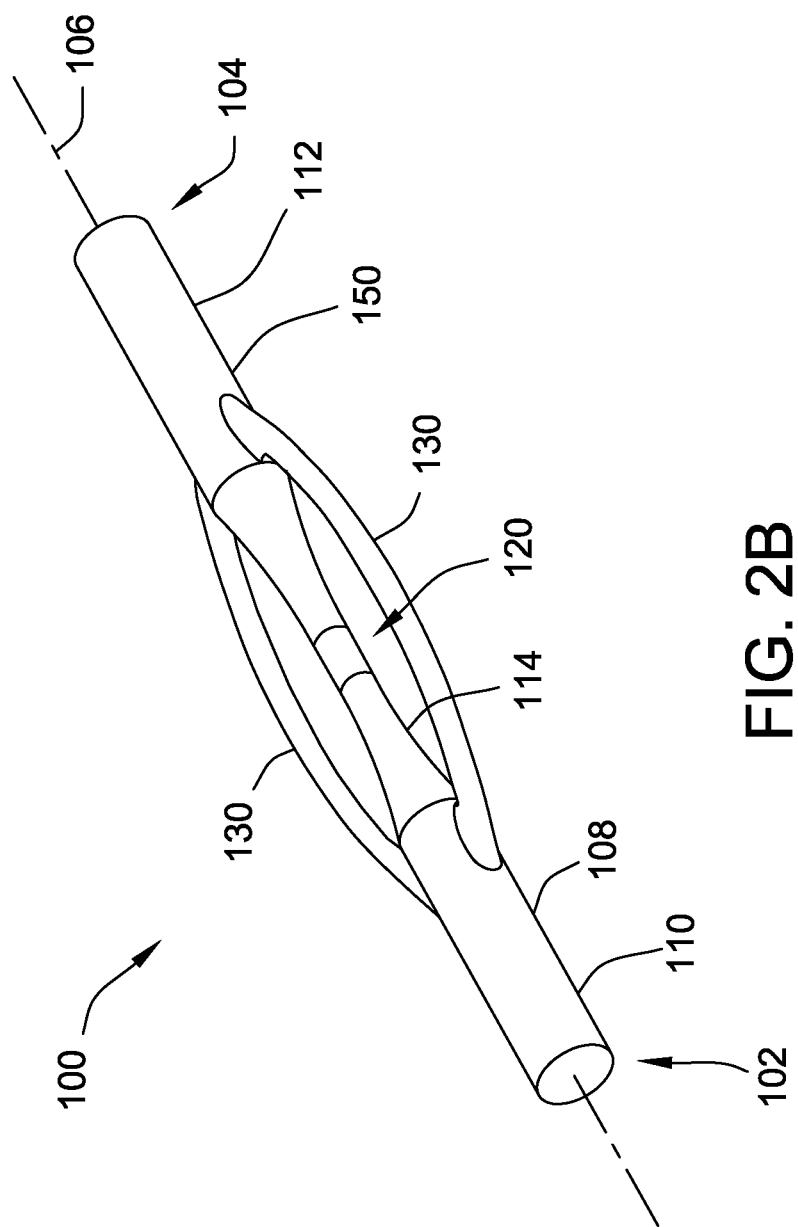
Figure 2C:
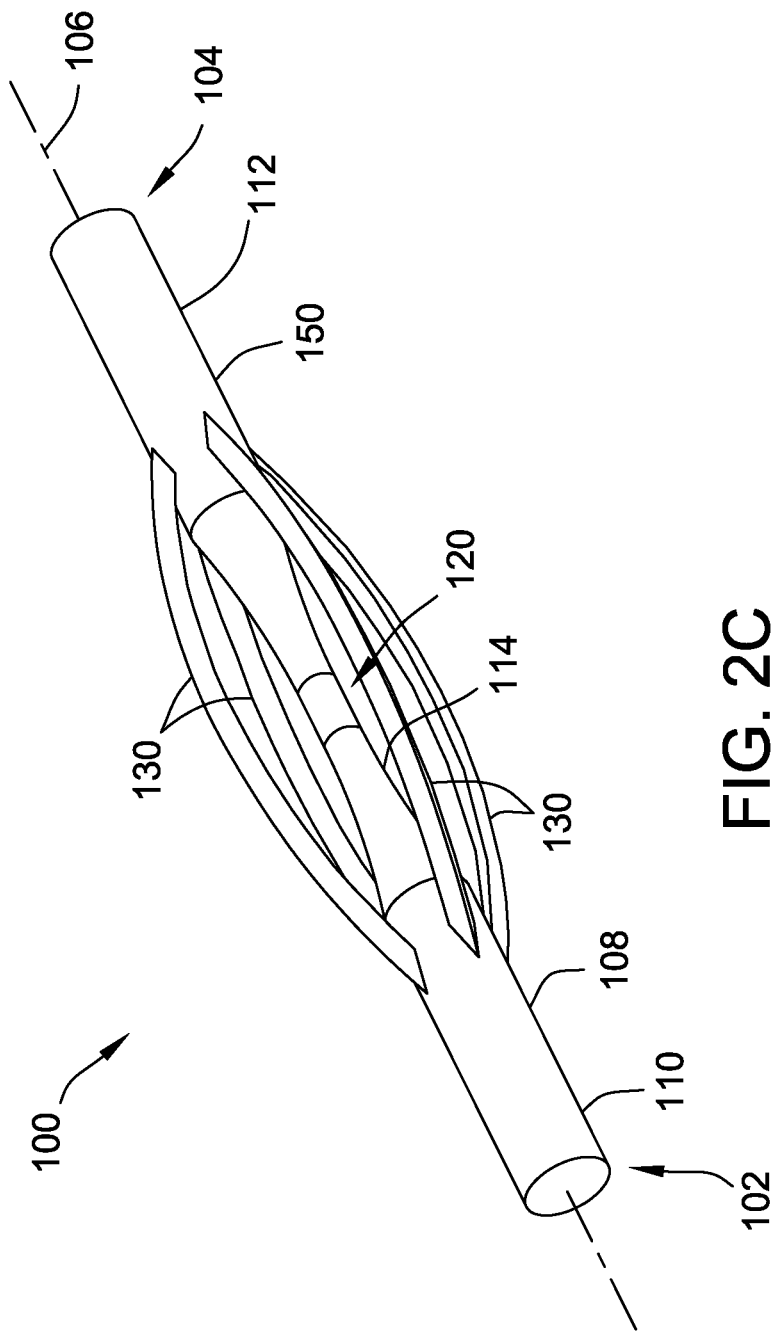
Figure 7:
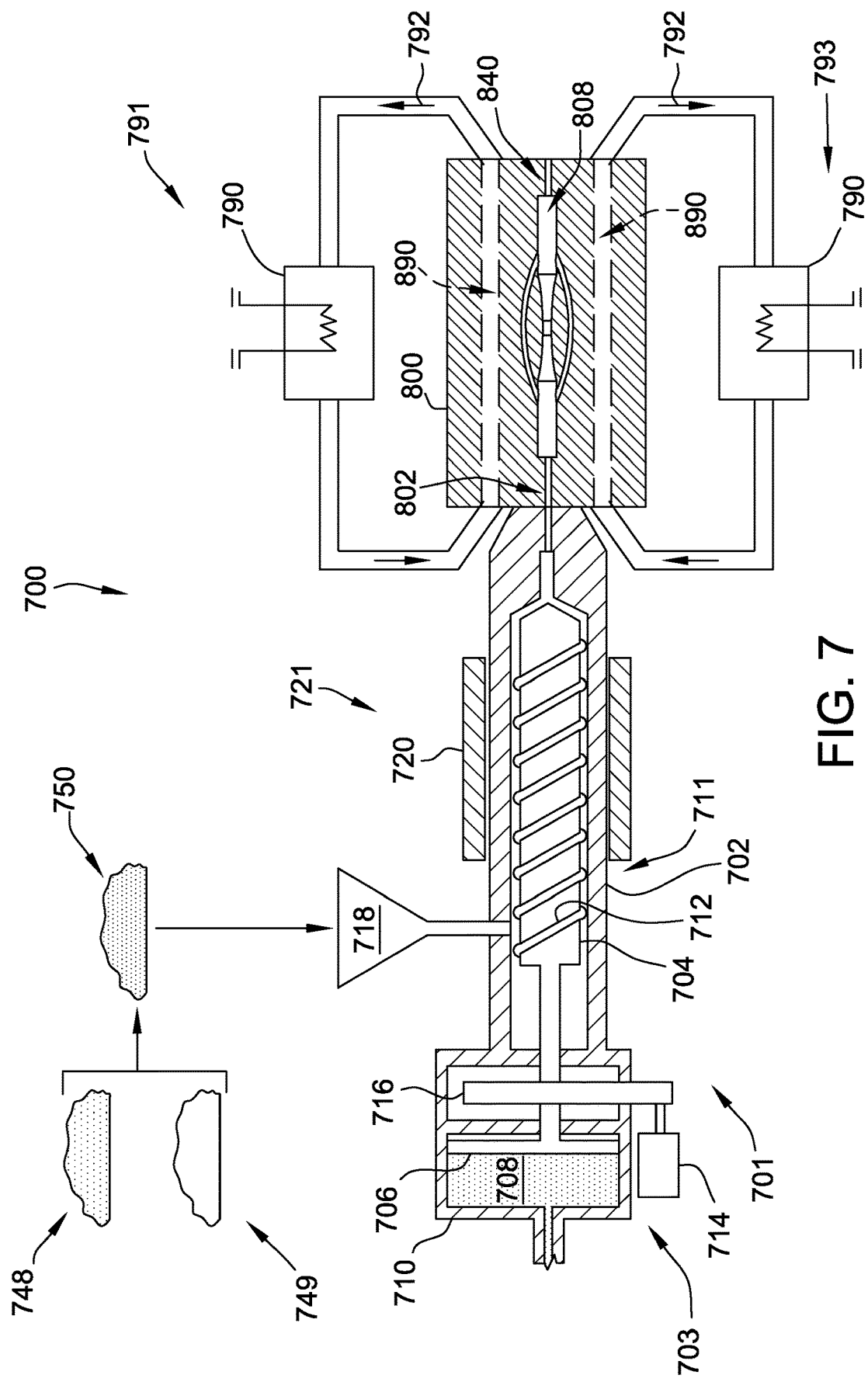
Figure 8B:
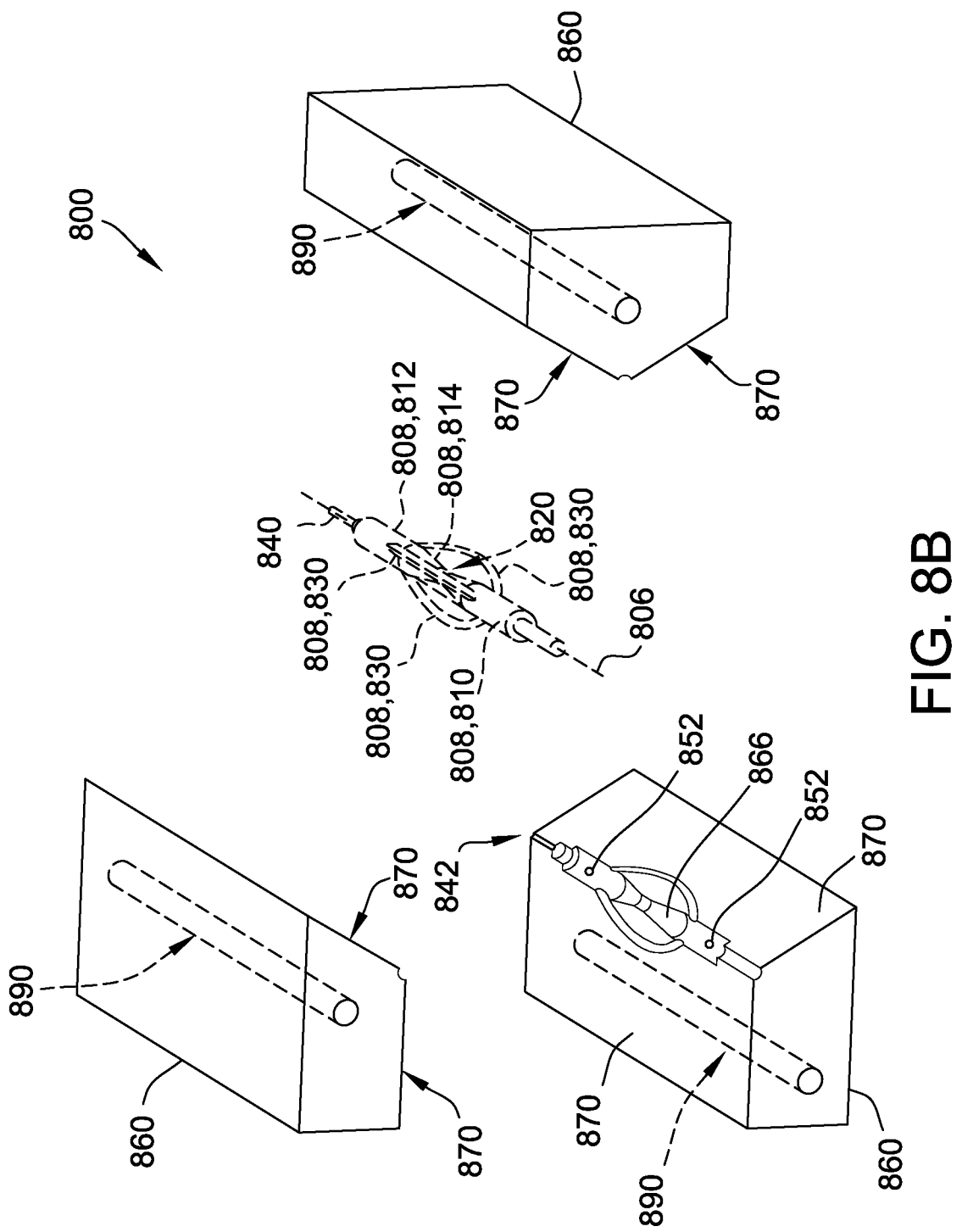
Figure 8C:
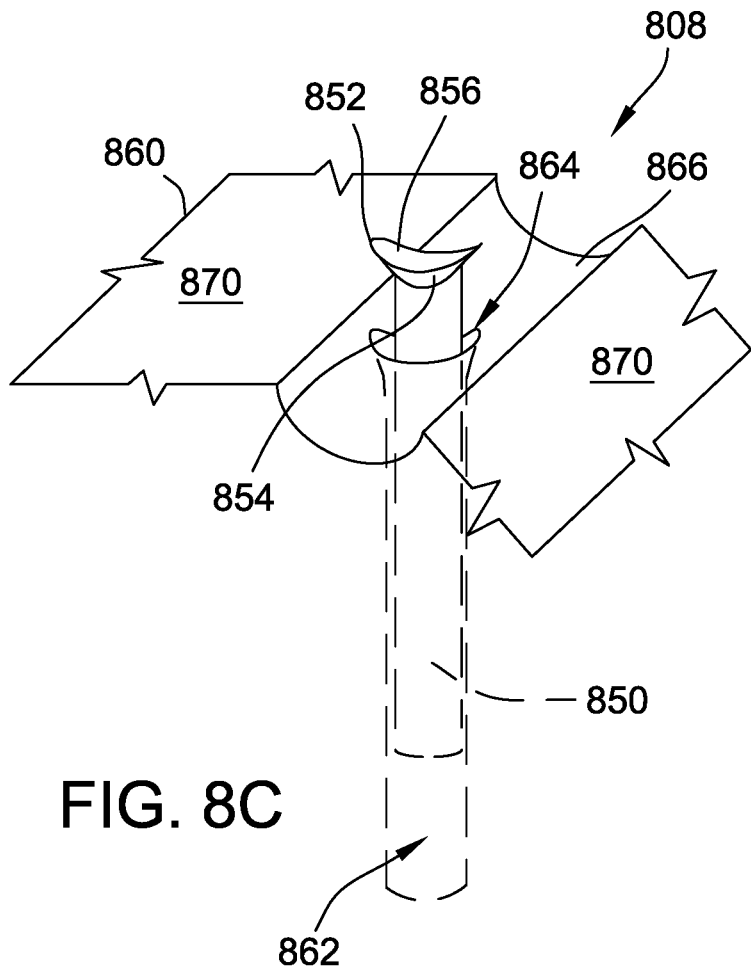
Figure 8D:
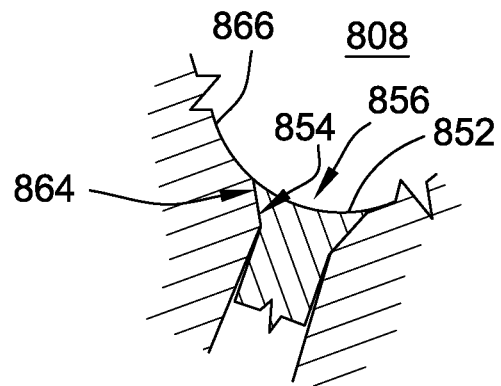
Figure 8E:
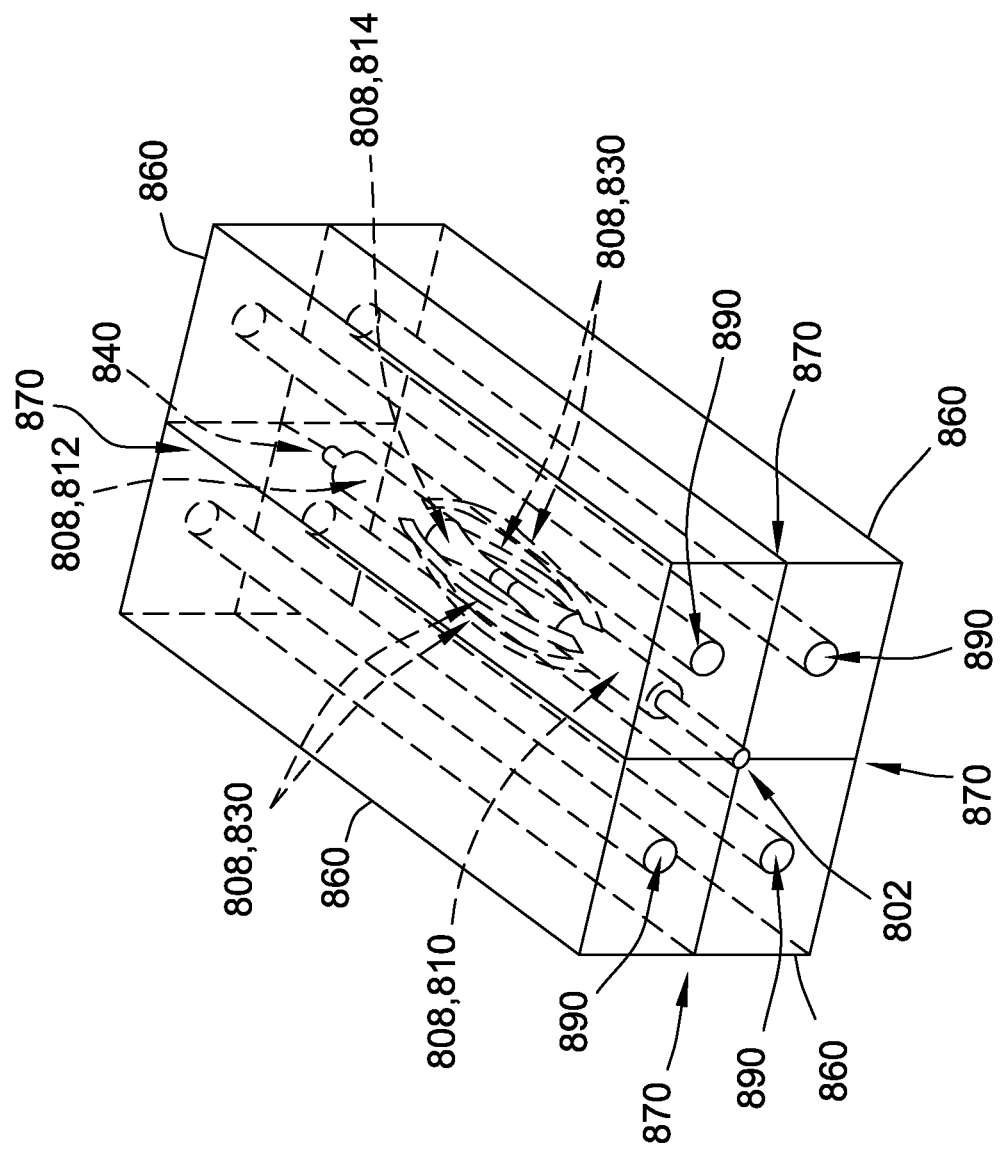
Figure 8F:
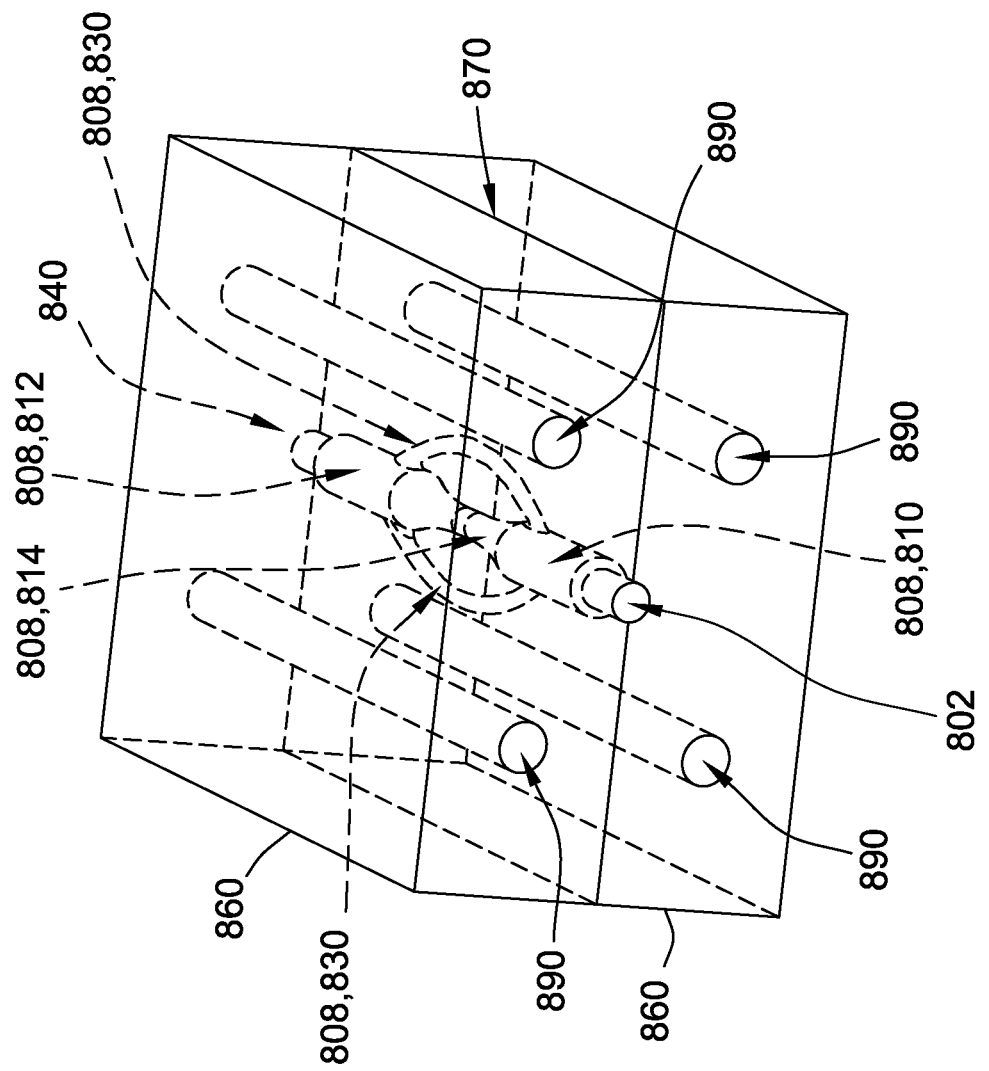
Figure 9:
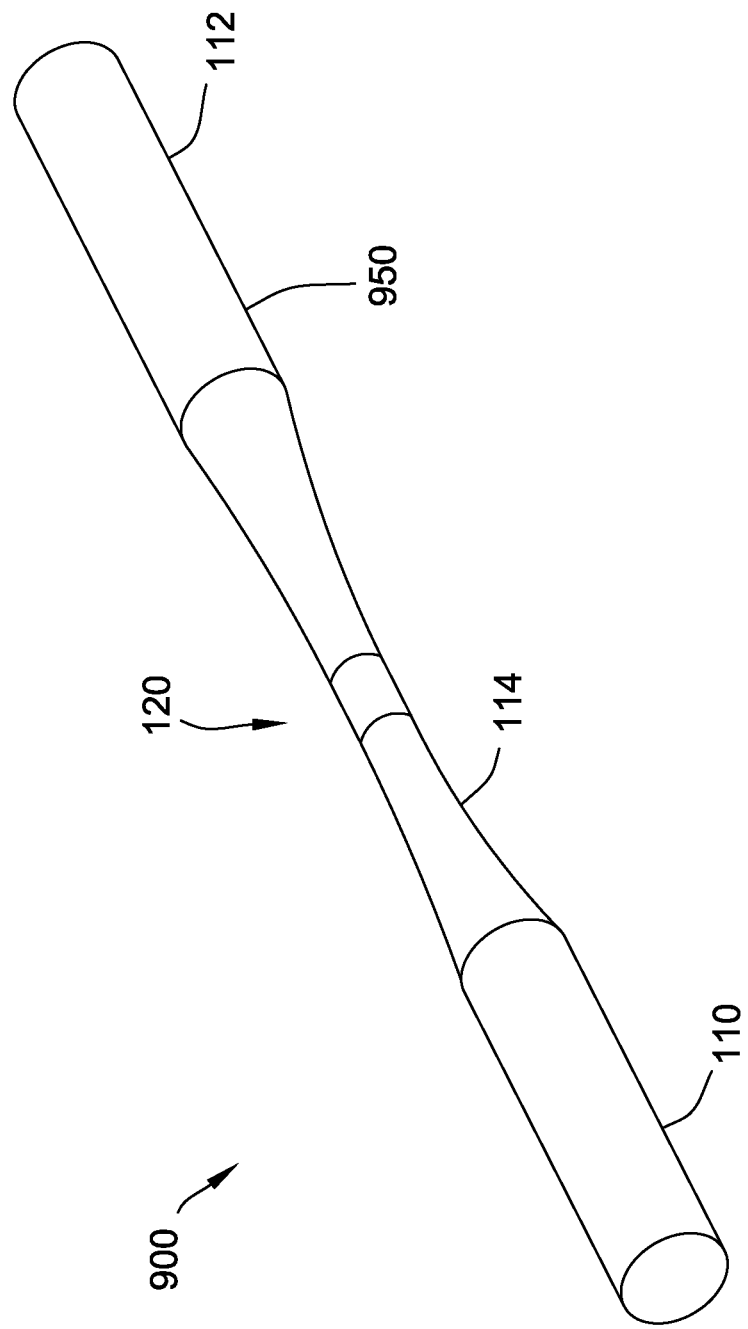
Figure 10C:
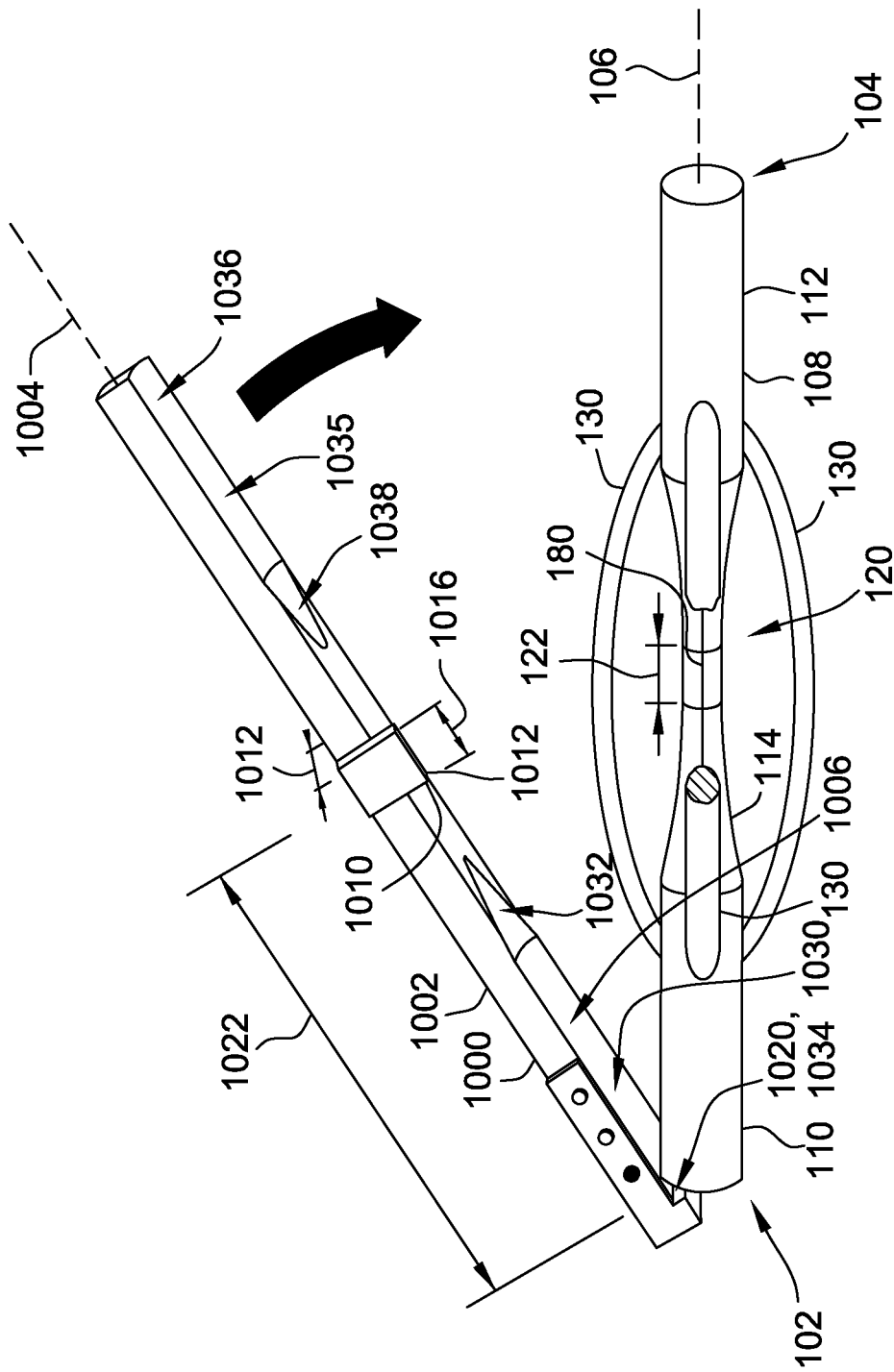
Figure 10D:
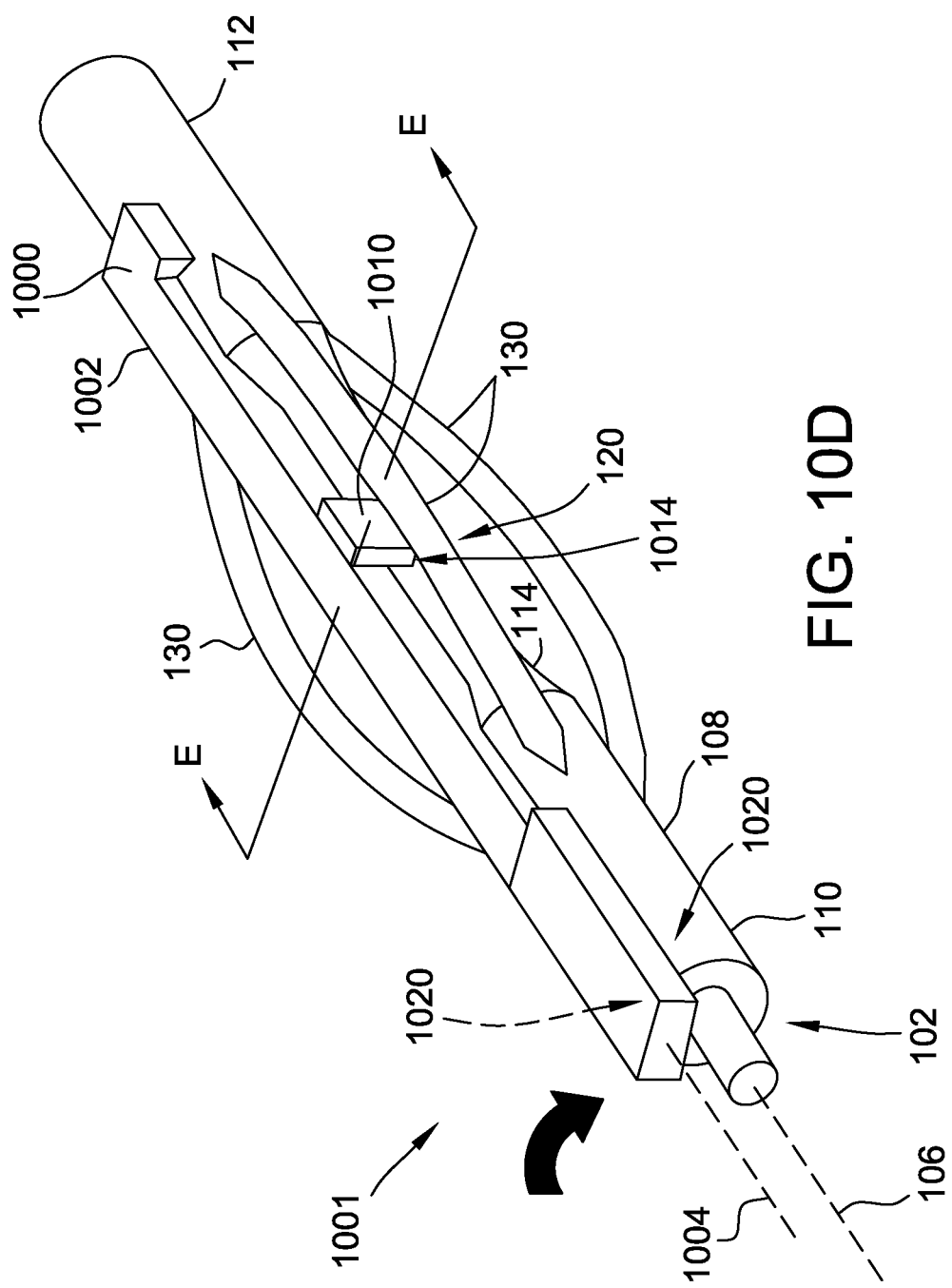
Figure 10E:
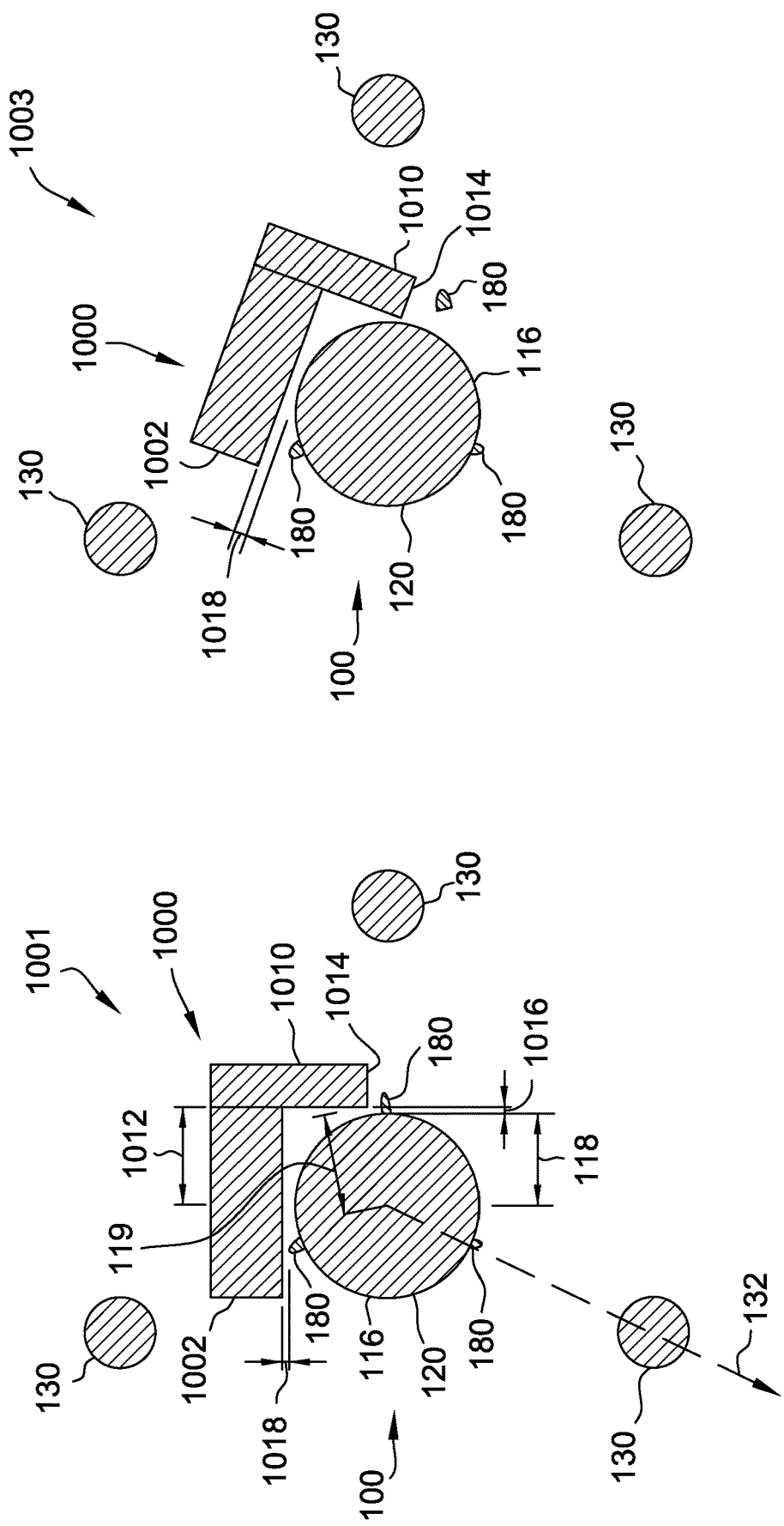
Figure 11A:
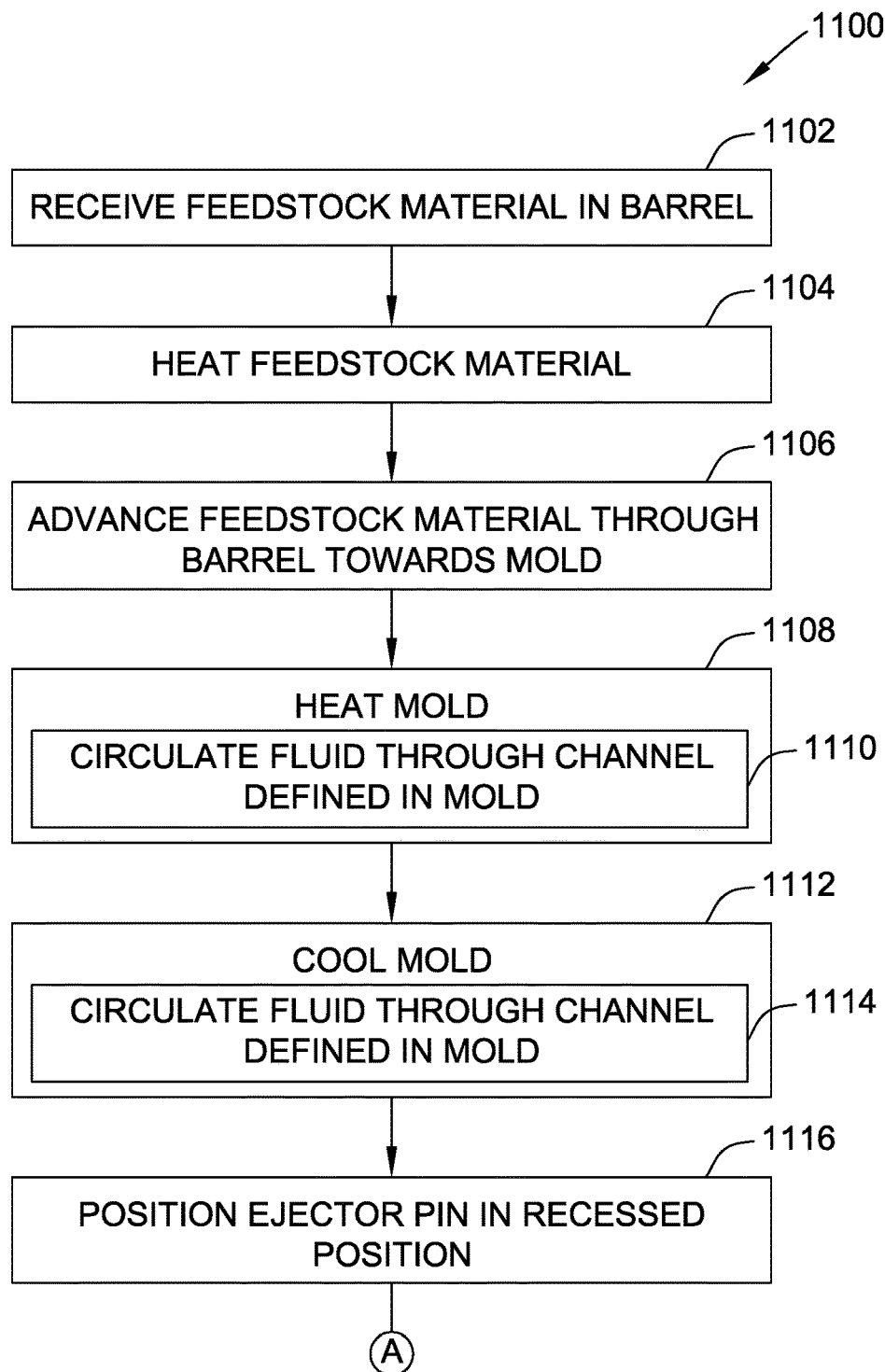
Figure 11B:
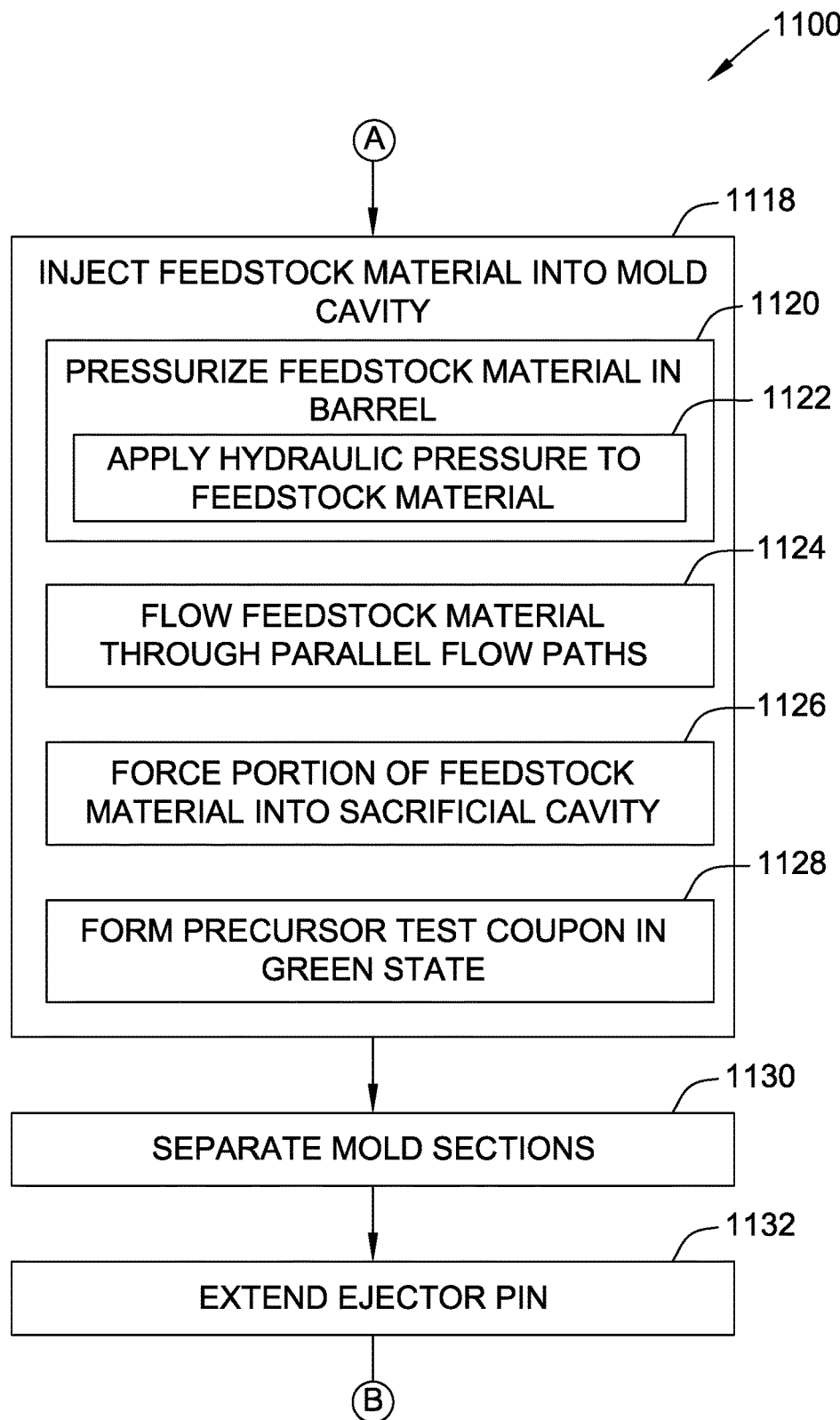
Figure 11C:
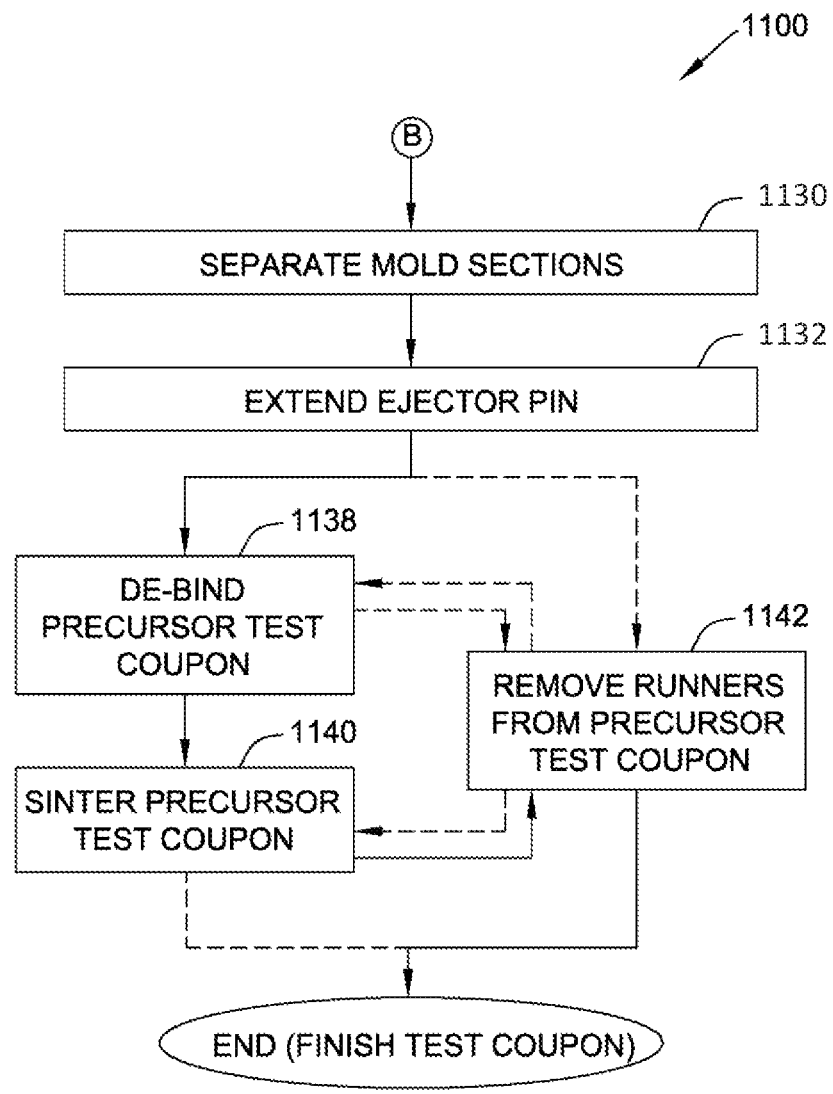
Figure 12A:
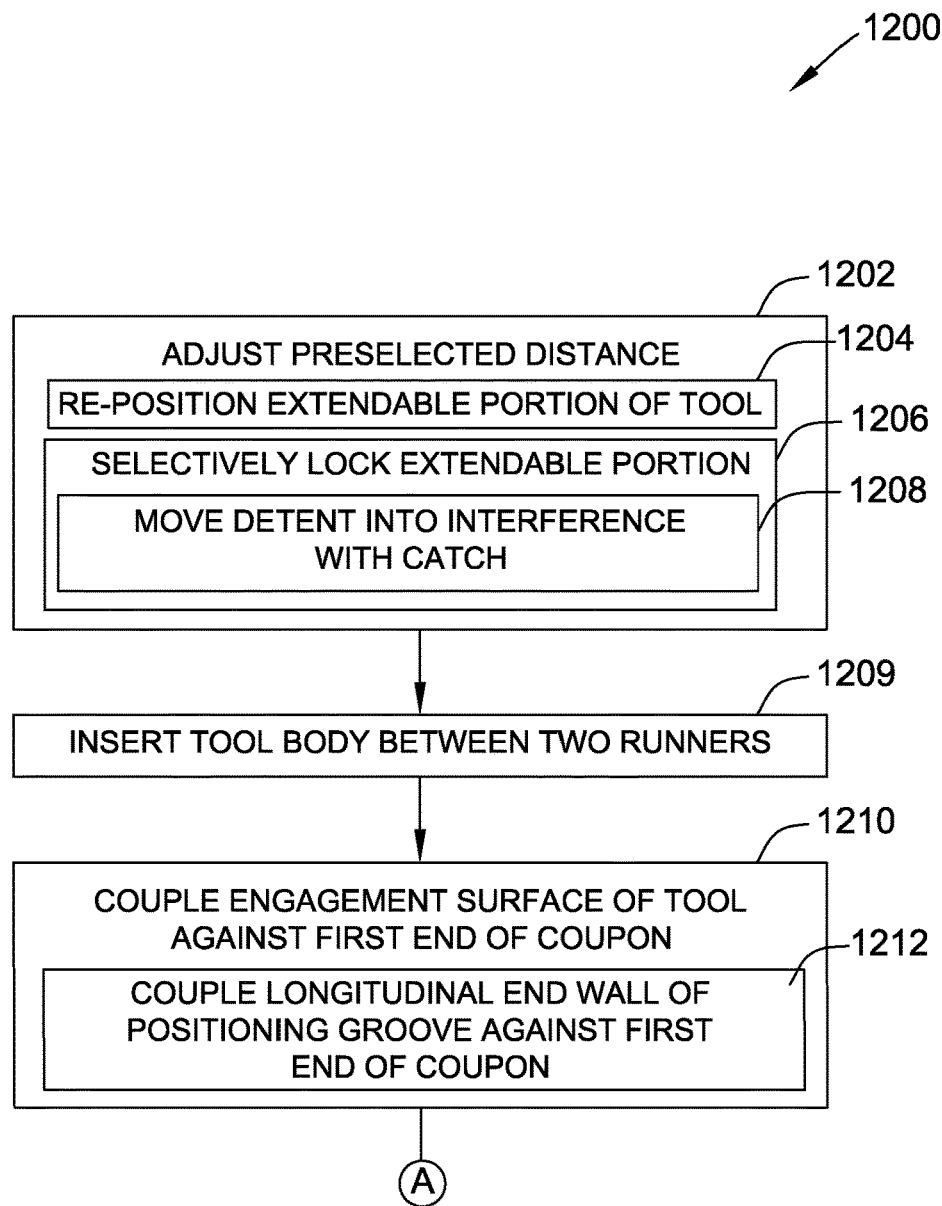
Figure 12B:
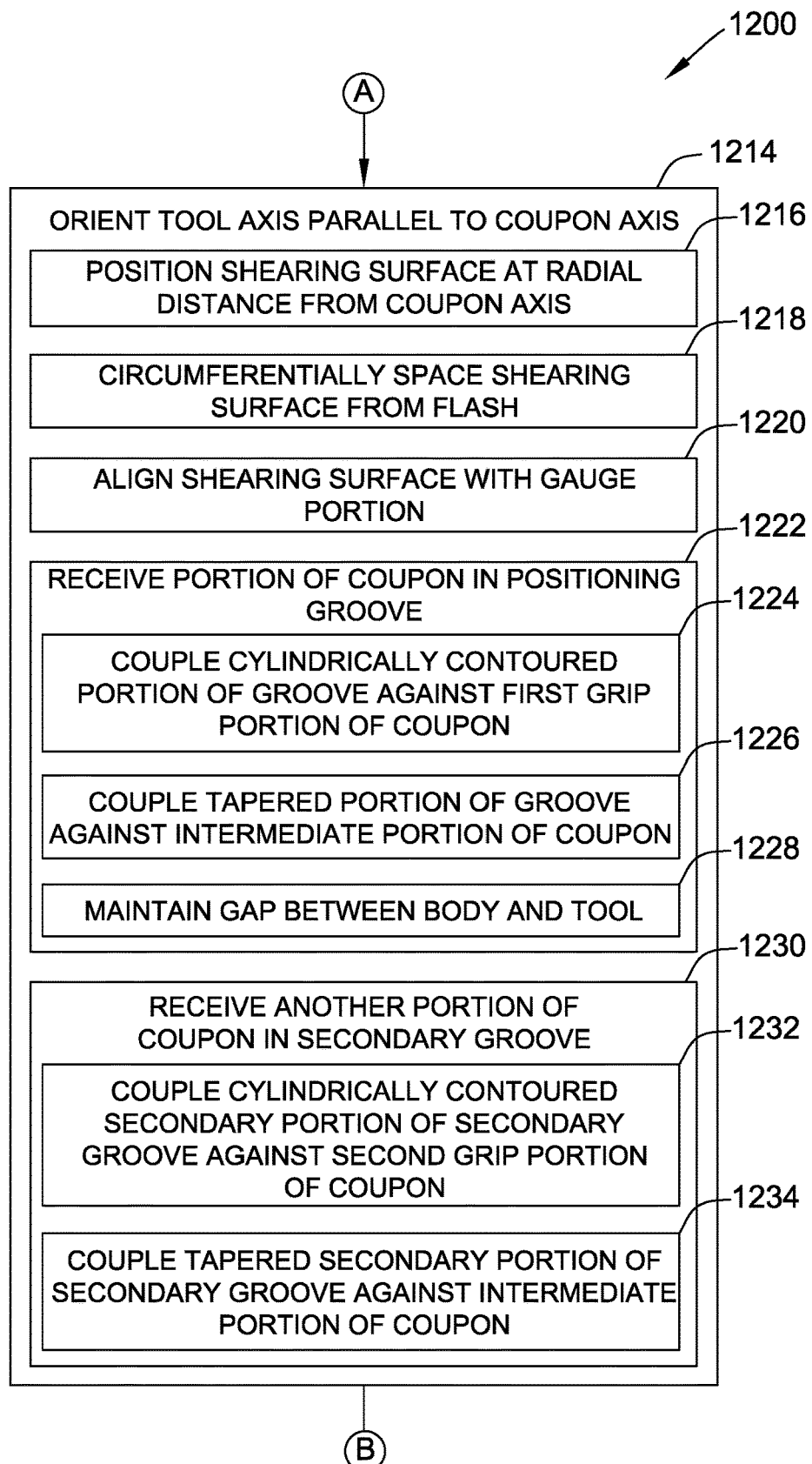
Figure 12C:
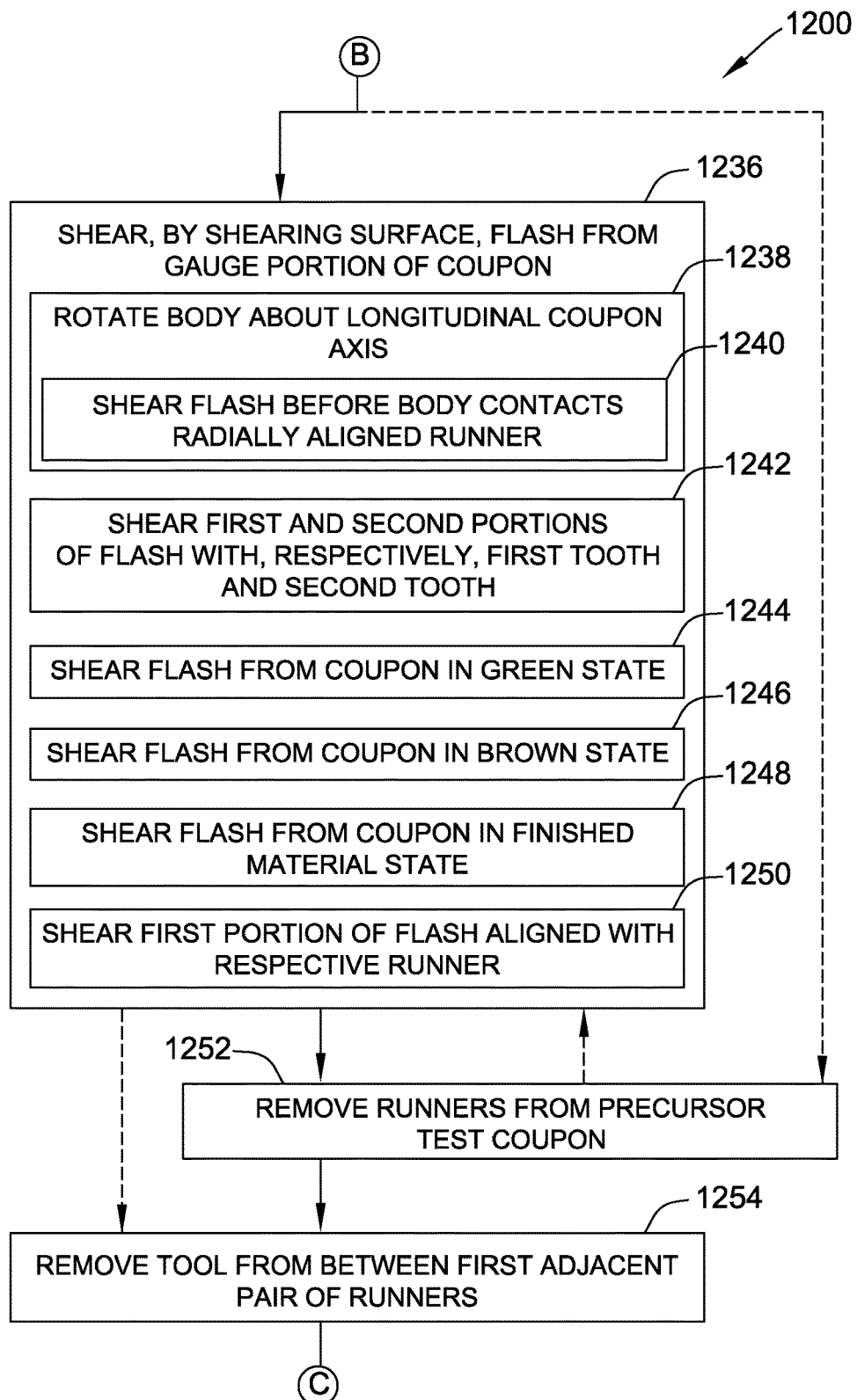
Figure 12D:
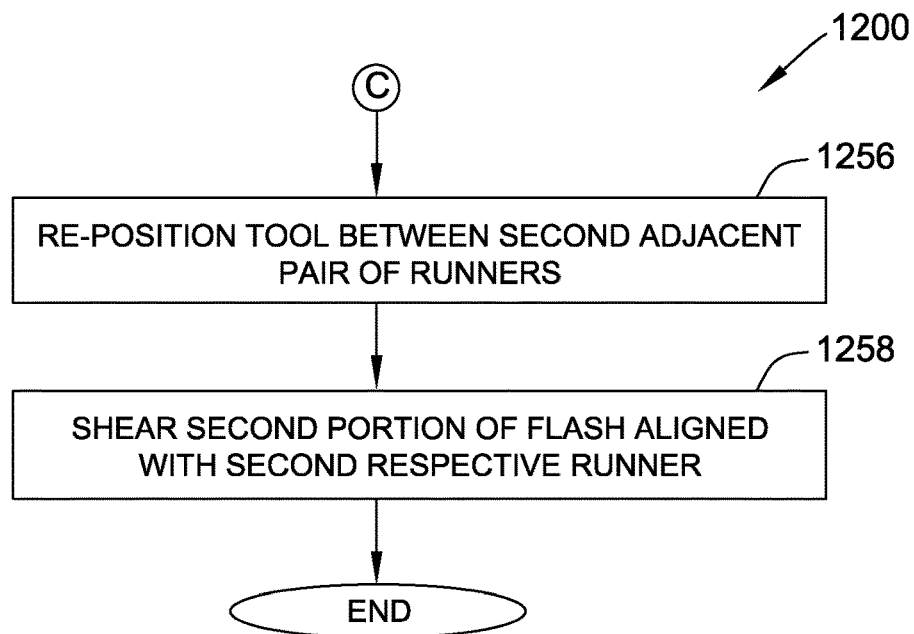
Figure 13:
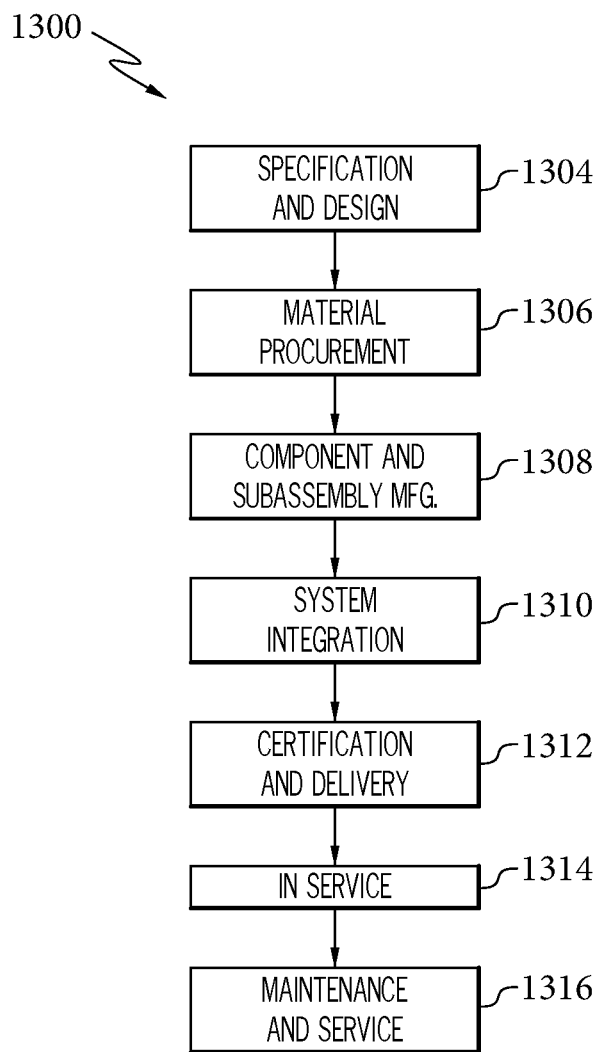

Having thus described one or more examples of the present disclosure in general terms, reference will now be made to the accompanying drawings, which are not necessarily drawn to scale, and wherein like reference characters designate the same or similar parts throughout the several views, and wherein:

FIG. 1A is a block diagram of a monolithic precursor test coupon, according to one or more examples of the present disclosure;

FIG. 1B is a block diagram of a metal injection molding apparatus, according to one or more examples of the present disclosure;

FIG. 1C is a block diagram of a flash removal tool, according to one or more examples of the present disclosure;

FIG. 2A is a schematic, perspective view of the monolithic precursor test coupon of FIG. 1A, having three runners, according to one or more examples of the present disclosure;

FIG. 2B is a schematic, perspective view of the monolithic precursor test coupon of FIG. 1A, having two runners, according to one or more examples of the present disclosure;

FIG. 2C is a schematic, perspective view of the monolithic precursor test coupon of FIG. 1A, having four runners, according to one or more examples of the present disclosure;

FIG. 3A is a schematic, elevation view of the monolithic precursor test coupon of FIG. 1A, having respective curvatures contiguous with respective grip portions, according to one or more examples of the present disclosure;

FIG. 3B is a schematic, elevation view of the monolithic precursor test coupon of FIG. 1A, having a continuous curvature between respective grip portions, according to one or more examples of the present disclosure;

FIG. 4 is a set of schematic, elevation views of respective intermediate portions of the monolithic precursor test coupon of FIG. 1A, having notches, according to one or more examples of the present disclosure;

FIG. 5 is a schematic, elevation view of the monolithic precursor test coupon of FIG. 1A, according to one or more examples of the present disclosure;

FIG. 6 is a schematic, sectional view of a portion of the monolithic precursor test coupon of FIG. 5, according to one or more examples of the present disclosure;

FIG. 7 is a schematic, elevation, partial cut-away view of the metal injection molding apparatus of FIG. 1B, according to one or more examples of the present disclosure;

FIG. 8A is a schematic, perspective view of the metal injection molding apparatus of FIG. 1B, having three runner cavities, according to one or more examples of the present disclosure;

FIG. 8B is a schematic, perspective, exploded view of the metal injection molding apparatus of FIG. 1B, having three runner cavities, according to one or more examples of the present disclosure;

FIG. 8C is a schematic, perspective view of a portion of the metal injection molding apparatus of FIG. 1B, including an ejector pin, according to one or more examples of the present disclosure;

FIG. 8D is a schematic, elevation, sectional view of a portion of the metal injection molding apparatus of FIG. 1B, including an ejector pin, according to one or more examples of the present disclosure;

FIG. 8E is a schematic, perspective view of the metal injection molding apparatus of FIG. 1B, having four runner cavities, according to one or more examples of the present disclosure;

FIG. 8F is a schematic, perspective view of the metal injection molding apparatus of FIG. 1B, having two runner cavities, according to one or more examples of the present disclosure;

FIG. 9 is a schematic, perspective, view of a test coupon formed from the monolithic precursor test coupon of FIG. 1A, according to one or more examples of the present disclosure;

FIG. 10A is a schematic, perspective view of the flash-removal tool of FIG. 1C, extending longitudinally on opposite sides of a tooth, according to one or more examples of the present disclosure;

FIG. 10B is a schematic, perspective view of the flash-removal tool of FIG. 1C, extending longitudinally on one side of a tooth, according to one or more examples of the present disclosure;

FIG. 10C is a schematic, perspective view of the flash-removal tool of FIG. 1C, being applied to the monolithic precursor test coupon of FIG. 1A shown in partial cutaway view, according to one or more examples of the present disclosure;

FIG. 10D is a schematic, perspective view of the flash-removal tool of FIG. 1C, applied to the monolithic precursor test coupon of FIG. 1A, according to one or more examples of the present disclosure;

FIG. 10E is a schematic, elevation, sectional view of the flash-removal tool of FIG. 1C applied to the monolithic precursor test coupon of FIG. 1A, according to one or more examples of the present disclosure;

FIGS. 11A, 11B, and 11C, collectively, are a block diagram of a method, according to one or more examples of the present disclosure, of making a test coupon utilizing the apparatus of FIG. 1B, according to one or more examples of the present disclosure;

FIGS. 12A, 12B, 12C, and 12D, collectively, are a block diagram of a method, according to one or more examples of the present disclosure, of removing flash from a gauge portion of a monolithic precursor test coupon utilizing the apparatus of FIG. 1C, according to one or more examples of the present disclosure;

FIG. 13 is a block diagram of aircraft production and service methodology; and

Figure 14:
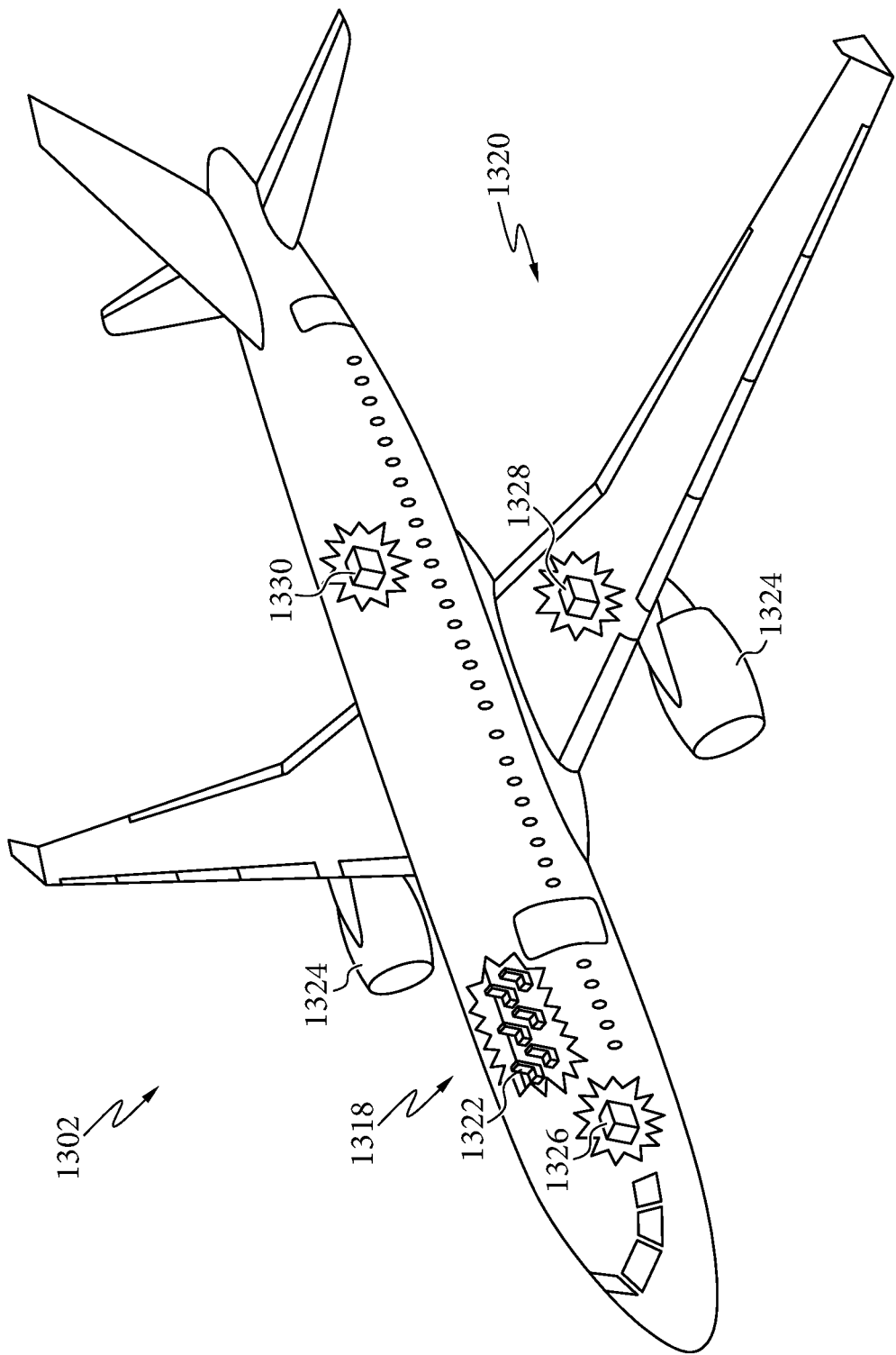

FIG. 14 is a schematic illustration of an aircraft.

DETAILED DESCRIPTION

In FIGS. 1A, 1B, and 1C, referred to above, solid lines, if any, connecting various elements and/or components may represent mechanical, electrical, fluid, optical, electromagnetic and other couplings and/or combinations thereof. As used herein, "coupled" means associated directly as well as indirectly. For example, a member A may be directly associated with a member B, or may be indirectly associated therewith, e.g., via another member C. It will be understood that not all relationships among the various disclosed elements are necessarily represented. Accordingly, couplings other than those depicted in the block diagrams may also exist. Dashed lines, if any, connecting blocks designating the various elements and/or components represent couplings similar in function and purpose to those represented by solid lines; however, couplings represented by the dashed lines may either be selectively provided or may relate to alternative examples of the present disclosure. Likewise, elements and/or components, if any, represented with dashed lines, indicate alternative examples of the present disclosure. One or more elements shown in solid and/or dashed lines may be omitted from a particular example without departing from the scope of the present disclosure. Environmental elements, if any, are represented with dotted lines. Virtual (imaginary) elements may also be shown for clarity. Those skilled in the art will appreciate that some of the features illustrated in FIGS. 1A, 1B, and 1C may be combined in various ways without the need to include other features described in FIGS. 1A, 1B, and 1C, other drawing figures, and/or the accompanying disclosure, even though such combination or combinations are not explicitly illustrated herein. Similarly, additional features not limited to the examples presented, may be combined with some or all of the features shown and described herein.

In FIGS. 11A, 11B, 11C, 12A, 12B, 12C and 12D, referred to above, the blocks may represent operations and/or portions thereof and lines connecting the various blocks do not imply any particular order or dependency of the operations or portions thereof. Blocks represented by dashed lines indicate alternative operations and/or portions thereof. Dashed lines, if any, connecting the various blocks represent alternative dependencies of the operations or portions thereof. It will be understood that not all dependencies among the various disclosed operations are necessarily represented. FIGS. 11A, 11B, 11C, 12A, 12B, 12C and 12D and the accompanying disclosure describing the operations of the method(s) set forth herein should not be interpreted as necessarily determining a sequence in which the operations are to be performed. Rather, although one illustrative order is indicated, it is to be understood that the sequence of the operations may be modified when appropriate. Accordingly, certain operations may be performed in a different order or simultaneously. Additionally, those skilled in the art will appreciate that not all operations described need be performed.

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one or more examples" means that one or more feature, structure, or characteristic described in connection with the example is included in at least one implementation. The phrase "one or more examples" in various places in the specification may or may not be referring to the same example.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

Illustrative, non-exhaustive examples, which may or may not be claimed, of the subject matter according the present disclosure are provided below.

Referring generally to FIGS. 1A and 1B, and particularly to, e.g., FIGS. 2A, 2B, and 2C, monolithic precursor test coupon 100 is disclosed. Monolithic precursor test coupon 100 comprises first grip portion 110, second grip portion 112, and intermediate portion 114, interconnecting first grip portion 110 and second grip portion 112. Monolithic precursor test coupon 100 also comprises runners 130, directly interconnecting first grip portion 110 and second grip portion 112 and not directly connected to intermediate portion 114. First grip portion 110, second grip portion 112, intermediate portion 114 and runners 130 are composed of substance 150 that comprises metal powder 748 and is in a green state. The preceding subject matter of this paragraph characterizes example 1 of the present disclosure.

Runners 130 provide monolithic precursor test coupon 100 with increased stability and inhibit breakage or warping of first grip portion 110, second grip portion 112, and intermediate portion 114 during and after a process of forming monolithic precursor test coupon 100, such as during one or more of: removal, in the green state, from a mold such as metal injection molding (MIM) apparatus 700 (shown in FIG. 8A); de-binding; and sintering. In addition, because runners 130 interconnect first grip portion 110 and second grip portion 112, and thus are not directly attached to intermediate portion 114, removal of runners 130 during a process of forming test coupon 900 (shown in FIG. 9) from monolithic precursor test coupon 100 poses a decreased risk of damage to intermediate portion 114, facilitating accuracy in subsequent material property testing using test coupon 900 formed from monolithic precursor test coupon 100.

Referring generally to FIG. 1A and particularly to, e.g., FIGS. 2A, 2B, and 2C, first grip portion 110, intermediate portion 114, and second grip portion 112 extend in series from first precursor-coupon end 102 to second precursor-coupon end 104 along longitudinal symmetry axis 106 and together define precursor-coupon body 108. The preceding subject matter of this paragraph characterizes example 2 of the present disclosure, wherein example 2 also includes the subject matter according to example 1, above.

First grip portion 110, intermediate portion 114, and second grip portion 112 extending in series from first precursor-coupon end 102 to second precursor-coupon end 104 along longitudinal symmetry axis 106 enable test coupon 900 (shown in FIG. 9) to be formed in near net shape from monolithic precursor test coupon 100 by removing runners 130.

Referring generally to FIG. 1A and particularly to, e.g., FIGS. 2A, 2B, and 2C, first grip portion 110 and second grip portion 112 have identical orders of symmetry about longitudinal symmetry axis 106. The preceding subject matter of this paragraph characterizes example 3 of the present disclosure, wherein example 3 also includes the subject matter according to example 2, above.

First grip portion 110 and second grip portion 112 having identical orders of symmetry about longitudinal symmetry axis 106 enable first grip portion 110 and second grip portion 112 to be mounted in a standard, off-the-shelf material property testing apparatus (not shown; for example, a tensile-test machine) with little or no modification required.

Referring generally to FIG. 1A and particularly to, e.g., FIGS. 2A, 2B, and 2C, intermediate portion 114 comprises gauge portion 120. Gauge portion 120 has gauge-portion cross-section, perpendicular to longitudinal symmetry axis 106. Gauge-portion cross-section is less than a cross-sectional area, perpendicular to longitudinal symmetry axis 106, of every portion of intermediate portion 114 other than gauge portion 120. The preceding subject matter of this paragraph characterizes example 4 of the present disclosure, wherein example 4 also includes the subject matter according to example 2 or 3, above.

Gauge portion 120 provides a location of smallest cross-section along test coupon 900 (shown in FIG. 9) formed from monolithic precursor test coupon 100. Gauge portion 120 thus provides an expected site of failure of test coupon 900 during material properties testing, and the cross-section of gauge portion 120 is usable, along with applied force measurements from a standard, off-the-shelf material property testing apparatus (not shown; for example, a tensile-test machine), to calculate the material properties of the material of test coupon 900.

Referring generally to FIG. 1A and particularly to, e.g., FIG. 3A, surface 116 of intermediate portion 114 has, in a plane that contains longitudinal symmetry axis 106, first curvature 302, contiguous with first grip portion 110, second curvature 304, contiguous with second grip portion 112, and a linear profile, defining gauge portion 120 over gauge length 122 between first curvature 302 and second curvature 304. The preceding subject matter of this paragraph characterizes example 5 of the present disclosure, wherein example 5 also includes the subject matter according to example 4, above.

First curvature 302, being contiguous with first grip portion 110, second curvature 304, being contiguous with second grip portion 112, and the linear profile, positioned between first curvature 302 and second curvature 304 and defining gauge portion 120, facilitates forming gauge portion 120 with a preselected stress profile, which simplifies calculation of material properties from results of testing test coupon 900 (shown in FIG. 9). In some examples, first curvature 302 is formed with first radius of curvature 312 and second curvature 304 is formed with second radius of curvature 314 that is substantially identical to first radius of curvature 312.

Referring generally to FIG. 1A and particularly to, e.g., FIG. 3B, surface 116 of intermediate portion 114 has continuous curvature 306 between first grip portion 110 and second grip portion 112 such that gauge portion 120 lies in a plane, perpendicular to longitudinal symmetry axis 106. The preceding subject matter of this paragraph characterizes example 6 of the present disclosure, wherein example 6 also includes the subject matter according to example 4, above.

Continuous curvature 306 between first grip portion 110 and second grip portion 112, such that gauge portion 120 lies in a plane, perpendicular to longitudinal symmetry axis 106, facilitates forming gauge portion 120 with a preselected stress profile, and further provides a relatively narrow region in which test coupon 900 (shown in FIG. 9) is expected to fail during certain material property testing methods, which simplifies calculation of material properties from results of testing test coupon 900. In some examples, continuous curvature 306 is formed with a single, constant radius of curvature 316, between first grip portion 110 and second grip portion 112.

Referring generally to FIG. 1A and particularly to, e.g., FIG. 4, intermediate portion 114 further comprises notch 400 and notch 400 comprises gauge portion 120. The preceding subject matter of this paragraph characterizes example 7 of the present disclosure, wherein example 7 also includes the subject matter according to any one of examples 4 to 6, above.

Notch 400 provides a relatively narrow region in which test coupon 900 (shown in FIG. 9) is expected to fail during certain material property testing methods, and also facilitates forming gauge portion 120 with a preselected stress profile, which simplifies calculation of material properties from results of testing test coupon 900.

Referring generally to FIG. 1A and particularly to, e.g., FIG. 4, notch 400 has, in a plane that contains longitudinal symmetry axis 106, one of angular profile 402 along longitudinal symmetry axis 106, arcuate profile 404 along longitudinal symmetry axis 106, or rectangular profile 406 along longitudinal symmetry axis 106. The preceding subject matter of this paragraph characterizes example 8 of the present disclosure, wherein example 8 also includes the subject matter according to example 7, above.

Notch 400 having one of one of angular profile 402, arcuate profile 404, or rectangular profile 406 further facilitates forming gauge portion 120 with a preselected stress profile, which simplifies calculation of material properties from results of testing test coupon 900 (shown in FIG. 9).

Referring generally to FIG. 1A and particularly to, e.g., FIG. 4, notch 400 is symmetrical about longitudinal symmetry axis 106. The preceding subject matter of this paragraph characterizes example 9 of the present disclosure, wherein example 9 also includes the subject matter according to example 7 or 8, above.

Notch 400 being symmetrical about longitudinal symmetry axis 106 facilitates forming gauge portion 120 with a preselected symmetrical stress profile, which simplifies calculation of certain material properties from results of testing test coupon 900 (shown in FIG. 9).

Referring generally to FIG. 1A and particularly to, e.g., FIG. 4, notch 400 is asymmetrical about longitudinal symmetry axis 106. The preceding subject matter of this paragraph characterizes example 10 of the present disclosure, wherein example 10 also includes the subject matter according to example 7 or 8, above.

Notch 400 being asymmetrical about longitudinal symmetry axis 106 facilitates forming gauge portion 120 with a preselected stress concentration in the asymmetric region, which simplifies calculation of certain material properties from results of testing test coupon 900 (shown in FIG. 9).

Referring generally to FIG. 1A and particularly to, e.g., FIGS. 2A, 2B, and 2C, runners of one pair of runners 130, adjacent to each other, and runners of any other pair of runners 130, adjacent to each other, have equal angular separations about longitudinal symmetry axis 106. The preceding subject matter of this paragraph characterizes example 11 of the present disclosure, wherein example 11 also includes the subject matter according to any one of examples 2 to 10, above.

Runners 130 having equal angular separations about longitudinal symmetry axis 106 facilitates increased stability of monolithic precursor test coupon 100.

Referring generally to FIG. 1A and particularly to, e.g., FIG. 5, total length 500 of monolithic precursor test coupon 100, measured along longitudinal symmetry axis 106, is between about 10.1 cm (4 inches) and about 30.5 cm (12 inches), and length 514 of intermediate portion 114 is between about 2.5 cm (1 inch) and about 15.2 cm (6 inches). The preceding subject matter of this paragraph characterizes example 12 of the present disclosure, wherein example 12 also includes the subject matter according to any one of examples 2 to 11, above.

In some examples, total length 500 and length 514 in the disclosed ranges enable test coupon 900 (shown in FIG. 9) formed from monolithic precursor test coupon 100 to be tested accurately in a standard, off-the-shelf material property testing apparatus (not shown; for example, a tensile-test machine) with little or no modification required.

Referring generally to FIG. 1A and particularly to, e.g., FIG. 5, grip diameter 510 of each of first grip portion 110 and second grip portion 112 is between about 0.25 cm (0.1 inches) and about 3.0 cm (1.2 inches), and least diameter 515 of intermediate portion 114 is between about 0.51 cm (0.2 inches) and about 1.52 cm (0.6 inches). The preceding subject matter of this paragraph characterizes example 13 of the present disclosure, wherein example 13 also includes the subject matter according to example 12, above.

In some examples, grip diameter 510 in the disclosed range enables test coupon 900 (shown in FIG. 9) formed from monolithic precursor test coupon 100 to be tested accurately in a standard, off-the-shelf material property testing apparatus (not shown; for example, a tensile-test machine) with little or no modification required.

Referring generally to FIG. 1A and particularly to, e.g., FIG. 5, each of runners 130 has, in a plane that contains longitudinal symmetry axis 106, radius of curvature 530 between about 7.6 cm (3 inches) and about 28.0 cm (11 inches). The preceding subject matter of this paragraph characterizes example 14 of the present disclosure, wherein example 14 also includes the subject matter according to example 12 or 13, above.

In some examples, radius of curvature 530 in the disclosed range provides sufficient separation between runners 130 and gauge portion 120 to enable flash 180 (shown in FIG. 10E) to be removed from gauge portion 120 before runners 130 are removed from monolithic precursor test coupon 100 to form test coupon 900 (shown in FIG. 9).

Referring generally to FIG. 1A and particularly to, e.g., FIGS. 5 and 6, each of runners 130 defines runner thickness 531, measured in a plane, intersecting intermediate portion 114. Runner thickness 531 is between about 0.25 cm (0.1 inches) and about 1.52 cm (0.6 inches). The preceding subject matter of this paragraph characterizes example 15 of the present disclosure, wherein example 15 also includes the subject matter according to any one of examples 12 to 14, above.

In some examples, runner thickness 531 in the disclosed range enables runners 130 to provide structural stability to monolithic precursor test coupon 100 to resist cracking or warping of monolithic precursor test coupon 100 during one or more of: removal, in the green state, from a mold, such as mold 800 (shown in FIG. 8A); de-binding; and sintering.

Referring generally to FIG. 1A and particularly to, e.g., FIG. 2A, runners 130 are three in number. The preceding subject matter of this paragraph characterizes example 16 of the present disclosure, wherein example 16 also includes the subject matter according to any one of examples 1 to 15, above.

In some examples, runners 130 being three in number enables runners 130 to provide structural stability to monolithic precursor test coupon 100 to resist cracking or warping of monolithic precursor test coupon 100 during one or more of: removal, in the green state, from a mold, such as mold 800 (shown in FIG. 8A); de-binding; and sintering.

Referring generally to FIG. 1A and particularly to, e.g., FIG. 2B, runners 130 are two in number. The preceding subject matter of this paragraph characterizes example 17 of the present disclosure, wherein example 17 also includes the subject matter according to any one of examples 1 to 15, above.

In some examples, runners 130 being two in number enables runners 130 to provide structural stability to monolithic precursor test coupon 100 to resist cracking or warping of monolithic precursor test coupon 100 during one or more of: removal, in the green state, from a mold, such as mold 800 (shown in FIG. 8A); de-binding; and sintering.

Referring generally to FIG. 1A and particularly to, e.g., FIG. 2C, runners 130 are four in number. The preceding subject matter of this paragraph characterizes example 18 of the present disclosure, wherein example 18 also includes the subject matter according to any one of examples 1 to 15, above.

In some examples, runners 130 being four in number enables runners 130 to provide structural stability to monolithic precursor test coupon 100 to resist cracking or warping of monolithic precursor test coupon 100 during one or more of: removal, in the green state, from a mold, such as mold 800 (shown in FIG. 8A); de-binding; and sintering.

Referring generally to FIG. 1A and particularly to, e.g., FIGS. 5 and 6, runners 130 are three or more in number, and runner width 533 increases in radial direction 534 away from intermediate portion 114. The preceding subject matter of this paragraph characterizes example 19 of the present disclosure, wherein example 19 also includes the subject matter according to any one of examples 1 to 15, above.

In some examples, runner width 533 increasing in radial direction 534 enables monolithic precursor test coupon 100 to be removed from mold 800 (shown in FIG. 8A) along a parting plane of mold 800 without interference from mold 800, while enabling runners 130 to provide structural stability to monolithic precursor test coupon 100 to resist cracking or warping of monolithic precursor test coupon 100 during one or more of: removal, in the green state, from mold 800; de-binding; and sintering.

Referring generally to FIG. 1A and particularly to, e.g., FIGS. 5 and 6, each of runners 130 is spaced apart from intermediate portion 114 by gap 532 along an entire extent of intermediate portion 114. The preceding subject matter of this paragraph characterizes example 20 of the present disclosure, wherein example 20 also includes the subject matter according to any one of examples 1 to 19, above.

Gap 532 decreases a risk of damage to intermediate portion 114 during a process of removing runners 130 from monolithic precursor test coupon 100 to form test coupon 900 (shown in FIG. 9).

Referring generally to FIG. 1B and particularly to, e.g., FIGS. 7 and 8A, 8B, 8E, and 8F, metal-injection-molding (MIM) apparatus 700 for making monolithic precursor test coupon 100 is disclosed. MIM apparatus 700 comprises mold 800, defining mold cavity 808. Mold cavity 808 comprises first-grip-portion cavity 810 and second-grip-portion cavity 812. Mold cavity 808 also comprises intermediate-portion cavity 814, interconnecting first-grip-portion cavity 810 and second-grip-portion cavity 812. Mold cavity 808 further comprises runner cavities 830, directly interconnecting first-grip-portion cavity 810 and second-grip-portion cavity 812 and not directly connected to intermediate-portion cavity 814. MIM apparatus 700 additionally comprises injector 701, operable to inject feedstock material 750, comprising metal powder 748, into mold cavity 808 to form monolithic precursor test coupon 100. The preceding subject matter of this paragraph characterizes example 21 of the present disclosure.

MIM apparatus 700 enables homogeneous distribution of feedstock material 750 within first-grip-portion cavity 810, intermediate-portion cavity 814, and second-grip-portion cavity 812 to facilitate formation of monolithic precursor test coupon 100 in mold 800 with reduced or eliminated voids, and further with reduced or eliminated shearing of binder 749 that is included in feedstock material 750 along with metal powder 748. More specifically, runner cavities 830 enable a portion of feedstock material 750 to bypass a flow restriction caused by intermediate-portion cavity 814 and provide back-fill of downstream portions of monolithic precursor test coupon 100 (shown in FIG. 1A). The bypass flow area provided by runner cavities 830 thus enables formation of monolithic precursor test coupon 100 having a proper distribution and integrity of feedstock material 750 at an injection rate that avoids problems of binder shearing or premature binder cross-linking.

Referring generally to FIG. 1B and particularly to, e.g., FIGS. 8A, 8B, 8E, and 8F, mold 800 comprises mold sections 860, shaped, when assembled together, to define mold cavity 808. The preceding subject matter of this paragraph characterizes example 22 of the present disclosure, wherein example 22 also includes the subject matter according to example 21, above.

Mold sections 860 enable disassembly of mold 800 to facilitate extraction of monolithic precursor test coupon 100 (shown in FIG. 1A) from mold 800 after the injection process is complete.

Referring generally to FIG. 1B and particularly to, e.g., FIGS. 8A, 8B, and 8E, runner cavities 830 are three or more in number, and mold sections 860 each comprise two parting surfaces 870. Each of parting surfaces 870 of one of mold sections 860 is shaped to abut a single one of parting surfaces 870 of another one of mold sections 860 when mold sections 860 are assembled together. Each of runner cavities 830 is defined between precisely two of mold sections 860. The preceding subject matter of this paragraph characterizes example 23 of the present disclosure, wherein example 23 also includes the subject matter according to example 22, above.

In examples in which runner cavities 830 are three or more in number, runner cavities 830 each being defined between precisely two of mold sections 860 reduces or eliminates interference of runners 130 (shown in FIG. 1A) with mold sections 860 during disassembly of mold sections 860 to remove monolithic precursor test coupon 100.

Referring generally to FIG. 1B and particularly to, e.g., FIGS. 8A, 8B, 8E, and 8F, mold sections 860 are equal in number to runner cavities 830. The preceding subject matter of this paragraph characterizes example 24 of the present disclosure, wherein example 24 also includes the subject matter according to example 22 or 23, above.

Mold sections 860 being equal in number to runner cavities 830 is a least number of mold sections 860 that enables runner cavities 830 to be defined between respective pairs of mold sections 860, which reduces or eliminates interference of runners 130 (shown in FIG. 1A) formed in runner cavities 830 with mold sections 860 during disassembly of mold sections 860 to remove monolithic precursor test coupon 100.

Referring generally to FIG. 1B and particularly to, e.g., FIGS. 8B, 8C, and 8D, at least one of mold sections 860 comprises mold cavity wall 866, oriented to define a boundary of mold cavity 808, and pin chamber 862, defined in at least one of mold sections 860 and depending from mold cavity wall 866. MIM apparatus 700 further comprises ejector pin 850, coupled to pin chamber 862 and selectively movable between, inclusively, a recessed position relative to pin chamber 862 and an extended position relative to pin chamber 862. Ejector pin 850 comprises pin head 852, having tapered lower surface 854 and upper surface 856, contiguous with tapered lower surface 854. Ejector pin 850, in the recessed position, is seated in pin chamber 862 so that upper surface 856 of pin head 852 is flush with mold cavity wall 866. Ejector pin 850, in the extended position, extends from pin chamber 862 so that pin head 852 is spaced from mold cavity wall 866. The preceding subject matter of this paragraph characterizes example 25 of the present disclosure, wherein example 25 also includes the subject matter according to any one of examples 22 to 24, above.

Ejector pin 850 movable from the recessed position to the extended position facilitates separating monolithic precursor test coupon 100 from mold sections 860 after mold sections 860 are disassembled for removal of monolithic precursor test coupon 100. More specifically, moving ejector pin 850 from the recessed position to the extended position pushes monolithic precursor test coupon 100 away from mold cavity wall 866.

Referring generally to FIG. 1B and particularly to, e.g., FIGS. 8A-8F, upper surface 856 of pin head 852 is contoured to match a local contour of mold cavity wall 866. The preceding subject matter of this paragraph characterizes example 26 of the present disclosure, wherein example 26 also includes the subject matter according to example 25, above.

Upper surface 856 of pin head 852 in the recessed position being contoured to match the local contour of mold cavity wall 866 facilitates reducing or eliminating imperfections imprinted by ejector pin 850 on a surface of monolithic precursor test coupon 100 during the MIM process.

Referring generally to FIG. 1B and particularly to, e.g., FIGS. 7 and 8A-8F, pin chamber 862 comprises tapered portion 864, contoured to receive tapered lower surface 854 of pin head 852 in direct sealing contact when ejector pin 850 is in the recessed position. The preceding subject matter of this paragraph characterizes example 27 of the present disclosure, wherein example 27 also includes the subject matter according to example 25 or 26, above.

Tapered portion 864 of pin chamber 862 being contoured to receive tapered lower surface 854 of pin head 852 facilitates creating a positive seal between pin head 852 and mold cavity wall 866 when injection pressure is applied by MIM apparatus 700. More specifically, ejector pin 850 in the recessed position, positive pressure inside mold cavity 808 reacts against pin head 852 and tends to force ejector pin 850 deeper into pin chamber 862, such that the greater the pressure inside mold cavity 808, the better the seal created between tapered lower surface 854 and tapered portion 864 of pin chamber 862. Accordingly, tapered portion 864 of pin chamber 862 tends to reduce or eliminate a potential for ejector pin 850 to become adhered in the recessed position, and thus inoperable to eject monolithic precursor test coupon 100, due to binder 749 seeping between pin head 852 and mold cavity wall 866 when MIM apparatus 700 applies pressure to mold cavity 808.

Referring generally to FIG. 1B and particularly to, e.g., FIGS. 8A and 8B, runner cavities 830 are three in number. The preceding subject matter of this paragraph characterizes example 28 of the present disclosure, wherein example 28 also includes the subject matter according to any one of examples 21 to 27, above.

Runner cavities 830 being three in number results in monolithic precursor test coupon 100 being formed with three runners 130, which provides for more efficient back-fill of monolithic precursor test coupon 100 and added stability to monolithic precursor test coupon 100 formed in mold cavity 808, as compared to runner cavities 830 being fewer than three in number.

Referring generally to FIG. 1B and particularly to, e.g., FIG. 8F, runner cavities 830 are two in number. The preceding subject matter of this paragraph characterizes example 29 of the present disclosure, wherein example 29 also includes the subject matter according to any one of examples 21 to 27, above.

Runner cavities 830 being two in number enables mold 800 to be assembled from as few as two mold sections 860, which results in a simpler mold design as compared to runner cavities 830 being greater than two in number.

Referring generally to FIG. 1B and particularly to, e.g., FIG. 8E, runner cavities 830 are four in number. The preceding subject matter of this paragraph characterizes example 30 of the present disclosure, wherein example 30 also includes the subject matter according to any one of examples 21 to 27, above.

Runner cavities 830 being four in number results in monolithic precursor test coupon 100 being formed with four runners 130, which provides for more efficient back-fill of monolithic precursor test coupon 100 and added stability to monolithic precursor test coupon 100 formed in mold cavity 808, as compared to runner cavities 830 being fewer than four in number.

Referring generally to FIG. 1B and particularly to, e.g., FIGS. 7, 8A, 8B, 8E, and 8F, mold 800 further defines sacrificial cavity 840 in downstream flow communication with mold cavity 808. The preceding subject matter of this paragraph characterizes example 31 of the present disclosure, wherein example 31 also includes the subject matter according to any one of examples 21 to 30, above.

Sacrificial cavity 840 provides a space for impurities and/or air initially present in mold cavity 808 and/or feedstock material 750 to be expelled from mold cavity 808 at a downstream location as additional an additional amount of feedstock material 750 continues to be injected into mold cavity 808 at an upstream location. For example, feedstock material 750 may initially be at a temperature that partially melts binder 749 out of feedstock material 750, which would undesirably alter a material property of monolithic precursor test coupon 100. The initial portion of feedstock material 750 is forced through mold cavity 808 into sacrificial cavity 840 as the temperature of feedstock material 750 is adjusted, enabling mold cavity 808 to be filled with feedstock material 750 having reduced or eliminated melt-out of binder 749.

Referring generally to FIG. 1B and particularly to, e.g., FIGS. 7, 8A, 8B, 8E, and 8F, downstream end 842 of sacrificial cavity 840 is closed. The preceding subject matter of this paragraph characterizes example 32 of the present disclosure, wherein example 32 also includes the subject matter according to example 31, above.

Downstream end 842 of sacrificial cavity 840 being closed reduces or eliminates the need for capturing and handling feedstock material 750, expelled during the MIM process.

Referring generally to FIG. 1B and particularly to, e.g., FIGS. 7, 8A, 8B, 8E, and 8F, downstream end 842 of sacrificial cavity 840 is open. The preceding subject matter of this paragraph characterizes example 33 of the present disclosure, wherein example 33 also includes the subject matter according to example 31, above.

Downstream end 842 of sacrificial cavity 840 being open facilitates inspection and evaluation of a quality of feedstock material 750, expelled during the MIM process to enable estimation of a quality of feedstock material 750, currently filling mold cavity 808. Downstream end 842 of sacrificial cavity 840 being open also enables an unlimited amount of feedstock material 750 to be expelled during the MIM process until a selected quality threshold is achieved.

Referring generally to FIG. 1B and particularly to, e.g., FIGS. 7, 8A, 8B, 8E, and 8F, injector 701 comprises barrel 702, configured to receive feedstock material 750. Injector 701 also comprises press 703, operable to force feedstock material 750 from barrel 702 through injection port 802 of mold 800 into first-grip-portion cavity 810. Press 703 is further operable to force feedstock material 750 from first-grip-portion cavity 810, in parallel through intermediate-portion cavity 814 and runner cavities 830, into second-grip-portion cavity 812. The preceding subject matter of this paragraph characterizes example 34 of the present disclosure, wherein example 34 also includes the subject matter according to any one of examples 21 to 33, above.

Barrel 702 and press 703 cooperate to provide a controllably pressurized delivery of feedstock material 750 into mold cavity 808. For example, barrel 702 is in flow communication with hopper 718. Feedstock material 750 is gravity-fed into hopper 718 and flows into barrel 702. After a suitable initial fill of barrel 702 with feedstock material 750, press 703 is operated to inject feedstock material 750 into mold cavity 808.

Referring generally to FIG. 1B and particularly to, e.g., FIG. 7, press 703 comprises cylinder 710, selectively fillable with pressurized fluid 708. Press 703 also comprises piston head 706, located within cylinder 710 and translatable toward barrel 702 in response to receipt of pressurized fluid 708 in cylinder 710. Press 703 further comprises piston rod 704, extending from piston head 706 out of cylinder 710 into barrel 702 and shaped to force feedstock material 750 from barrel 702 through injection port 802 in response to translation of piston head 706 toward barrel 702. The preceding subject matter of this paragraph characterizes example 35 of the present disclosure, wherein example 35 also includes the subject matter according to example 34, above.

Piston head 706, piston rod 704, and cylinder 710 cooperate to provide a hydraulically controllable pressurization mechanism to implement press 703.

Referring generally to FIG. 1B and particularly to, e.g., FIG. 7, MIM apparatus 700 further comprises feedstock heater 721, operable to heat feedstock material 750 in barrel 702. The preceding subject matter of this paragraph characterizes example 36 of the present disclosure, wherein example 36 also includes the subject matter according to example 34 or 35, above.

Feedstock heater 721 facilitates heating feedstock material 750 to within a temperature range that is sufficiently high to enable suitable flow of feedstock material 750 through mold cavity 808, yet not sufficiently high to melt binder 749 out of feedstock material 750 and not sufficiently high to cross-link and solidify binder 749 prior to adequate fill of mold cavity 808.

Referring generally to FIG. 1B and particularly to, e.g., FIG. 7, feedstock heater 721 comprises resistance heater 720, coupled to barrel 702. The preceding subject matter of this paragraph characterizes example 37 of the present disclosure, wherein example 37 also includes the subject matter according to example 36, above.

Resistance heater 720 coupled to barrel 702 provides an electrically controllable heating mechanism to implement feedstock heater 721.

Referring generally to FIG. 1B and particularly to, e.g., FIG. 7, MIM apparatus 700 further comprises barrel 702, configured to receive feedstock material 750. MIM apparatus 700 also comprises screw 711, operable to advance feedstock material 750 through barrel 702 toward mold 800 and to compact feedstock material 750, adjacent to mold 800. The preceding subject matter of this paragraph characterizes example 38 of the present disclosure, wherein example 38 also includes the subject matter according to any one of examples 21 to 37, above.

Barrel 702 and screw 711 cooperate to provide an efficient mechanism to compact feedstock material 750 received in barrel 702, for example from hopper 718, adjacent to mold 800.

Referring generally to FIG. 1B and particularly to, e.g., FIG. 7, injector 701 comprises piston rod 704, extending into barrel 702 and shaped to force feedstock material 750 from barrel 702 through injection port 802 of mold 800. Screw 711 comprises thread 712, located on an outer surface of piston rod 704. Screw 711 also comprises motor 714, operable to rotate piston rod 704. The preceding subject matter of this paragraph characterizes example 39 of the present disclosure, wherein example 39 also includes the subject matter according to example 38, above.

Thread 712 on the outer surface of piston rod 704, wherein piston rod 704 is rotatable by motor 714 and also is shaped to force feedstock material 750 from barrel 702 into mold 800, provides a spatially compact and efficient mechanism to implement screw 711. For example, motor 714 is operable to selectively rotationally drive piston rod 704 through a cooperating gear 716, affixed to piston rod 704. In some implementations, piston rod 704 further is selectively linearly drivable by hydraulic action on piston head 706 positioned within cylinder 710, as described above, further enhancing spatial compactness and efficiency.

In other examples, screw 711 is implemented independently of piston rod 704.

Referring generally to FIG. 1B and particularly to, e.g., FIG. 7, MIM apparatus 700 further comprises mold heater 791, operable to heat mold 800. The preceding subject matter of this paragraph characterizes example 40 of the present disclosure, wherein example 40 also includes the subject matter according to any one of examples 21 to 39, above.

Mold heater 791 facilitates maintaining feedstock material 750 during injection within the temperature range that is sufficiently high to enable suitable flow of feedstock material 750 through mold cavity 808, yet not sufficiently high to melt binder 749 out of feedstock material 750 and not sufficiently high to cross-link and solidify binder 749 prior to adequate fill of mold cavity 808. For example, mold heater 791 is operable to maintain feedstock material 750, during injection, at approximately the same temperature initially induced by feedstock heater 721 while feedstock material 750 is in barrel 702.

Referring generally to FIG. 1B and particularly to, e.g., FIGS. 7, and 8A, 8B, 8E, and 8F, mold heater 791 comprises at least one channel 890, defined in mold 800. Mold heater 791 also comprises at least one heat exchanger 790, operable to heat fluid 792 circulated through at least one channel 890. The preceding subject matter of this paragraph characterizes example 41 of the present disclosure, wherein example 41 also includes the subject matter according to example 40, above.

Heat exchanger 790 operable to heat fluid 792 circulated through at least one channel 890 provides a controllable heating mechanism to implement mold heater 791. For example, at least one channel 890 is implemented as a plurality of channels, with a respective one of at least one channel 890 extending through each of mold sections 860 to facilitate consistent heating among mold sections 860.

Referring generally to FIG. 1B and particularly to, e.g., FIG. 7, MIM apparatus 700 further comprises mold cooler 793, operable to cool mold 800. The preceding subject matter of this paragraph characterizes example 42 of the present disclosure, wherein example 42 also includes the subject matter according to any one of examples 21 to 41, above.

After injection of feedstock material 750 is complete, mold cooler 793 facilitates cooling feedstock material 750 within mold cavity 808 to facilitate removal of monolithic precursor test coupon 100 from mold cavity 808. For example, cooling of feedstock material 750 facilitates handling of monolithic precursor test coupon 100 after formation in mold 800, and also tends to cause monolithic precursor test coupon 100 to shrink, which facilitates separation of monolithic precursor test coupon 100 from mold cavity wall 866.

Referring generally to FIG. 1B and particularly to, e.g., FIGS. 7, 8A, 8B, 8E, and 8F, mold cooler 793 comprises at least one channel 890, defined in mold 800. Mold cooler 793 also comprises at least one heat exchanger 790, operable to cool fluid 792, circulated through at least one channel 890. The preceding subject matter of this paragraph characterizes example 43 of the present disclosure, wherein example 43 also includes the subject matter according to example 42, above.

Heat exchanger 790 operable to cool fluid 792 circulated through at least one channel 890 provides a controllable cooling mechanism to implement mold cooler 793. For example, at least one channel 890 is implemented as a plurality of channels, with a respective one of at least one channel 890 extending through each of mold sections 860 to facilitate consistent cooling among mold sections 860. In some implementations, heat exchanger 790 is also operable to heat fluid 792 circulated through at least one channel 890, as described above, enabling both heating and cooling of mold 800 to be implemented by the same ones of heat exchanger 790 and at least one channel 890, enhancing spatial compactness and efficiency of MIM apparatus 700.

Referring generally to FIG. 1B and particularly to, e.g., FIGS. 8A, 8B, 8E, and 8F, first-grip-portion cavity 810, intermediate-portion cavity 814, and second-grip-portion cavity 812 are arranged in series along longitudinal mold-cavity axis 806. Intermediate-portion cavity 814 comprises gauge-portion cavity 820, defining a gauge cross-sectional flow area, perpendicular to longitudinal mold-cavity axis 806. The gauge cross-sectional flow area is a least value of a set of values of cross-sectional flow areas, perpendicular to longitudinal mold-cavity axis 806 at all locations along first-grip-portion cavity 810, intermediate-portion cavity 814, and second-grip-portion cavity 812. The preceding subject matter of this paragraph characterizes example 44 of the present disclosure, wherein example 44 also includes the subject matter according to any one of examples 21 to 43, above.

The gauge cross-sectional flow area being a least value of a set of values of cross-sectional flow areas at all locations along first-grip-portion cavity 810, intermediate-portion cavity 814, and second-grip-portion cavity 812 creates gauge portion 120 of monolithic precursor test coupon 100 (shown in FIG. 1) as an expected site of failure of test coupon 900 (shown in FIG. 9) during material properties testing. The cross-section of gauge portion 120 is usable, along with applied force measurements from a standard, off-the-shelf material property testing apparatus (not shown; for example, a tensile-test machine), to calculate the material properties of the material of test coupon 900.

Referring generally to FIG. 1C and particularly to, e.g., FIGS. 10A-10E, flash-removal tool 1000 is disclosed. Flash-removal tool 1000 comprises tool body 1002, extending along longitudinal tool axis 1004. Flash-removal tool 1000 also comprises tooth 1010, projecting from tool body 1002 in first direction 1090. Flash-removal tool 1000 further comprises engagement surface 1020, located preselected distance 1022 away from tooth 1010 along longitudinal tool axis 1004 and perpendicular to longitudinal tool axis 1004. Tooth 1010 comprises shearing surface 1014, facing in first direction 1090 and located offset distance 1012 away from longitudinal tool axis 1004 in second direction 1092. First direction 1090 and second direction 1092 are orthogonal to each other and define a plane, perpendicular to longitudinal tool axis 1004. The preceding subject matter of this paragraph characterizes example 45 of the present disclosure.

Engagement surface 1020 being located preselected distance 1022 away from tooth 1010 enables tooth 1010 to align longitudinally with gauge portion 120 when engagement surface 1020 engages monolithic precursor test coupon 100 (shown in FIG. 1). Moreover, tooth 1010 projecting from tool body 1002 in first direction 1090 and having shearing surface 1014, located offset distance 1012 away from longitudinal tool axis 1004 in second direction 1092 enables tooth 1010 to slide between runners 130 (shown in FIG. 1) of monolithic precursor test coupon 100 such that shearing surface 1014 aligns precisely with flash 180 on gauge portion 120. Thus, flash-removal tool 1000 facilitates removal of flash 180 from gauge portion 120, while runners 130 are still attached to monolithic precursor test coupon 100, without requiring complex alignment procedures or adjustments.

Referring generally to FIG. 1C and particularly to, e.g., FIGS. 10A-10E, engagement surface 1020 is defined on tool body 1002, such that preselected distance 1022 is non-adjustable. The preceding subject matter of this paragraph characterizes example 46 of the present disclosure, wherein example 46 also includes the subject matter according to example 45, above.

Preselected distance 1022 being non-adjustable simplifies manufacture and facilitates the use of flash-removal tool 1000. For example, monolithic precursor test coupon 100 is manufactured such that first precursor-coupon end 102 is separated from gauge portion 120 (shown in FIG. 1) by a standard longitudinal distance, and flash-removal tool 1000 is manufactured having preselected distance 1022 that is non-adjustable and equal to the standard longitudinal distance from first precursor-coupon end 102 to gauge portion 120.

Referring generally to FIG. 1C and particularly to, e.g., FIGS. 10A and 10C, flash-removal tool 1000 further comprises extendable portion 1041, movable with respect to tool body 1002 to adjust preselected distance 1022. The preceding subject matter of this paragraph characterizes example 47 of the present disclosure, wherein example 47 also includes the subject matter according to example 45 or 46, above.

Preselected distance 1022 being adjustable, via extendable portion 1041 movable with respect to tool body 1002, facilitates adaptability of flash-removal tool 1000 to monolithic precursor test coupon 100 (shown in FIG. 1) having various sizes. For example, monolithic precursor test coupon 100 is manufactured in different longitudinal sizes corresponding to different sizes of test coupon 900 needed for use with different material property testing machines (not shown). Preselected distance 1022 being adjustable enables a single tool, such as flash-removal tool 1000, to be used with more than one size of monolithic precursor test coupon 100.

Referring generally to FIG. 1C and particularly to, e.g., FIGS. 10A and 10C, extendable portion 1041 comprises telescoping portion 1040, coupled to tool body 1002. Engagement surface 1020 is defined on telescoping portion 1040. The preceding subject matter of this paragraph characterizes example 48 of the present disclosure, wherein example 48 also includes the subject matter according to example 47, above.

Telescoping portion 1040 coupled to tool body 1002 provides a mechanically simple and effective structure for implementation of extendable portion 1041.

Referring generally to FIG. 1C and particularly to, e.g., FIGS. 10A and 10C, flash-removal tool 1000 further comprises lock 1043, operable to selectively lock telescoping portion 1040 in position relative to tool body 1002 after preselected distance 1022 is adjusted. The preceding subject matter of this paragraph characterizes example 49 of the present disclosure, wherein example 49 also includes the subject matter according to example 48, above.

Lock 1043 promotes stability and ease of use of flash-removal tool 1000, having preselected distance 1022 that is adjustable.

Referring generally to FIG. 1C and particularly to, e.g., FIG. 10A, lock 1043 comprises detent 1044, located on one of telescoping portion 1040 or tool body 1002, and plurality of catches 1046, arranged longitudinally on another of telescoping portion 1040 or tool body 1002. Each one of catches 1046 is configured to interfere with detent 1044 when telescoping portion 1040 is correspondingly adjusted relative to tool body 1002. The preceding subject matter of this paragraph characterizes example 50 of the present disclosure, wherein example 50 also includes the subject matter according to example 49, above.

Detent 1044 and catches 1046 provides a mechanically simple and effective structure for implementation of lock 1043.

Referring generally to FIG. 1C and particularly to, e.g., FIGS. 10A-10C, flash-removal tool 1000 further comprises positioning groove 1006, defined in tool body 1002. Positioning groove 1006 extends longitudinally between engagement surface 1020 and tooth 1010 and faces in first direction 1090. The preceding subject matter of this paragraph characterizes example 51 of the present disclosure, wherein example 51 also includes the subject matter according to any one of examples 45 to 50, above Positioning groove 1006 facilitates stable positioning of flash-removal tool 1000 against monolithic precursor test coupon 100 (shown in FIG. 1).

Referring generally to FIG. 1C and particularly to, e.g., FIGS. 10A-10C, engagement surface 1020 forms longitudinal end-wall 1034 of positioning groove 1006. The preceding subject matter of this paragraph characterizes example 52 of the present disclosure, wherein example 52 also includes the subject matter according to example 51, above.

Engagement surface 1020 forming longitudinal end-wall 1034 of positioning groove 1006 combines the mechanism for longitudinally positioning tooth 1010 within an additional mechanism for stable positioning of flash-removal tool 1000 against monolithic precursor test coupon 100 (shown in FIG. 1), facilitating a compact design for flash-removal tool 1000.

Referring generally to FIG. 1C and particularly to, e.g., FIGS. 10A-10C, positioning groove 1006 comprises cylindrically contoured portion 1030, extending parallel to longitudinal tool axis 1004. The preceding subject matter of this paragraph characterizes example 53 of the present disclosure, wherein example 53 also includes the subject matter according to example 51 or 52, above.

Cylindrically contoured portion 1030 of positioning groove 1006 facilitates stable positioning of flash-removal tool 1000 against first grip portion 110 of monolithic precursor test coupon 100 (shown in FIG. 1) for implementations in which first grip portion 110 has a cylindrical profile complementary to cylindrically contoured portion 1030.

Referring generally to FIG. 1C and particularly to, e.g., FIGS. 10A-10C, positioning groove 1006 further comprises tapered portion 1032, extending longitudinally between cylindrically contoured portion 1030 and tooth 1010 and parallel to longitudinal tool axis 1004. The preceding subject matter of this paragraph characterizes example 54 of the present disclosure, wherein example 54 also includes the subject matter according to example 53, above.

Tapered portion 1032 of positioning groove 1006 facilitates stable positioning of flash-removal tool 1000 against intermediate portion 114 of monolithic precursor test coupon 100 (shown in FIG. 1) for implementations in which intermediate portion 114, adjacent to first grip portion 110, has a longitudinally tapering profile complementary to tapered portion 1032.

Referring generally to FIG. 1C and particularly to, e.g., FIGS. 10A and 10C, flash-removal tool 1000 further comprises secondary groove 1035, defined in tool body 1002. Tooth 1010 divides tool body 1002 longitudinally into two sides. Positioning groove 1006 extends longitudinally on one of the two sides, and secondary groove 1035 extends longitudinally on another of the two sides and faces in first direction 1090. The preceding subject matter of this paragraph characterizes example 55 of the present disclosure, wherein example 55 also includes the subject matter according to any one of examples 51 to 54, above.

Secondary groove 1035 further facilitates stable positioning of flash-removal tool 1000 against monolithic precursor test coupon 100 (shown in FIG. 1).

Referring generally to FIG. 1C and particularly to, e.g., FIGS. 10A and 10C, secondary groove 1035 comprises cylindrically contoured secondary portion 1036, extending parallel to longitudinal tool axis 1004. The preceding subject matter of this paragraph characterizes example 56 of the present disclosure, wherein example 56 also includes the subject matter according to example 55, above.

Cylindrically contoured secondary portion 1036 of secondary groove 1035 facilitates stable positioning of flash-removal tool 1000 against second grip portion 112 of monolithic precursor test coupon 100 (shown in FIG. 1) for implementations in which second grip portion 112 has a cylindrical profile complementary to cylindrically contoured secondary portion 1036.

Referring generally to FIG. 1C and particularly to, e.g., FIGS. 10A and 10C, secondary groove 1035 further comprises tapered secondary portion 1038, parallel to longitudinal tool axis 1004 and extending longitudinally between cylindrically contoured secondary portion 1036 and tooth 1010. The preceding subject matter of this paragraph characterizes example 57 of the present disclosure, wherein example 57 also includes the subject matter according to example 56, above.

Tapered secondary portion 1038 of secondary groove 1035 facilitates stable positioning of flash-removal tool 1000 against intermediate portion 114 of monolithic precursor test coupon 100 (shown in FIG. 1) for implementations in which intermediate portion 114, adjacent to second grip portion 112, has a longitudinally tapering profile complementary to tapered secondary portion 1038.

Referring generally to FIG. 1C and particularly to, e.g., FIG. 10B, flash-removal tool 1000 further comprises second tooth 1011. Longitudinal tool axis 1004 is located between tooth 1010 and second tooth 1011. The preceding subject matter of this paragraph characterizes example 58 of the present disclosure, wherein example 58 also includes the subject matter according to any one of examples 45 to 57, above.

Second tooth 1011 positioned opposite tooth 1010 facilitates removal of multiple portions of flash 180 (shown in FIG. 10E) without requiring disengagement of flash-removal tool 1000 from monolithic precursor test coupon 100 (shown in FIG. 1) and subsequent re-positioning of flash-removal tool 1000 to re-position tooth 1010.

Referring generally to FIG. 1C and particularly to, e.g., FIG. 10B, second tooth 1011 is located preselected distance 1022 away from engagement surface 1020 along longitudinal tool axis 1004. The preceding subject matter of this paragraph characterizes example 59 of the present disclosure, wherein example 59 also includes the subject matter according to example 58, above.

Engagement surface 1020 being located preselected distance 1022 away from second tooth 1011 enables second tooth 1011 to align longitudinally with gauge portion 120, simultaneously to tooth 1010 aligning longitudinally with gauge portion 120, when engagement surface 1020 engages monolithic precursor test coupon 100 (shown in FIG. 1).

Referring generally to FIG. 1C and particularly to, e.g., FIG. 10B, tooth 1010 is monolithic with tool body 1002. The preceding subject matter of this paragraph characterizes example 60 of the present disclosure, wherein example 60 also includes the subject matter according to any one of examples 45 to 59, above.

Tooth 1010 being monolithic with tool body 1002 simplifies manufacture of flash-removal tool 1000.

Referring generally to FIG. 1C and particularly to, e.g., FIG. 10A, tooth 1010 is formed separately from, and coupled to, tool body 1002. The preceding subject matter of this paragraph characterizes example 61 of the present disclosure, wherein example 61 also includes the subject matter according to any one of examples 45 to 59, above.

Tooth 1010 being formed separately from, and coupled to, tool body 1002 facilitates manufacture of flash-removal tool 1000 having various longitudinal sizes from standard elements used to form tool body 1002 and tooth 1010.

Referring generally to FIG. 1C and particularly to, e.g., FIGS. 10A and 10B, tool body 1002 extends along longitudinal tool axis 1004 from first end 1050 to second end 1052. Engagement surface 1020 is located adjacent to first end 1050. The preceding subject matter of this paragraph characterizes example 62 of the present disclosure, wherein example 62 also includes the subject matter according to any one of examples 45 to 61, above.

Engagement surface 1020 being located adjacent to first end 1050 of flash-removal tool 1000 facilitates a compact design for flash-removal tool 1000.

Referring generally to FIG. 1C and particularly to, e.g., FIGS. 10A and 10B, tooth 1010 is located at second end 1052. The preceding subject matter of this paragraph characterizes example 63 of the present disclosure, wherein example 63 also includes the subject matter according to example 62, above.

Tooth 1010 being located at second end 1052 of flash-removal tool 1000 facilitates a compact design for flash-removal tool 1000.

Referring generally to FIG. 1C and particularly to, e.g., FIGS. 10A and 10B, tooth 1010 is spaced apart from second end 1052 along longitudinal tool axis 1004. The preceding subject matter of this paragraph characterizes example 64 of the present disclosure, wherein example 64 also includes the subject matter according to example 62, above.

Tooth 1010 being spaced apart longitudinally from second end 1052 of flash-removal tool 1000 facilitates stability of coupling flash-removal tool 1000 to monolithic precursor test coupon 100 (shown in FIG. 1). For example, secondary groove 1035 is included in the longitudinal portion of tool body 1002 between tooth 1010 and second end 1052.

Referring generally to FIGS. 11A-11C and particularly to, e.g., FIGS. 2A-2C, 8A-8F, and 9, method 1100 of making test coupon 900 using mold 800 is disclosed. Mold 800 defines mold cavity 808 that comprises first-grip-portion cavity 810, second-grip-portion cavity 812, and intermediate-portion cavity 814, interconnecting first-grip-portion cavity 810 and second-grip-portion cavity 812. Mold cavity 808 further comprises runner cavities 830, directly interconnecting first-grip-portion cavity 810 and second-grip-portion cavity 812 and not directly connected to intermediate-portion cavity 814. Method 1100 comprises (block 1118) injecting feedstock material 750, comprising metal powder 748, into mold cavity 808 to form monolithic precursor test coupon 100 in mold cavity 808. Monolithic precursor test coupon 100 comprises first grip portion 110, having a shape complementary to that of first-grip-portion cavity 810, and second grip portion 112, having a shape complementary to that of second-grip-portion cavity 812. Monolithic precursor test coupon 100 also comprises intermediate portion 114, having a shape complementary to that of intermediate-portion cavity 814, and runners 130, each having a shape complementary to that of a corresponding one of runner cavities 830. Method 1100 also comprises (block 1142) removing runners 130 from monolithic precursor test coupon 100. The preceding subject matter of this paragraph characterizes example 65 of the present disclosure.

Method 1100 enables homogeneous distribution of feedstock material 750 within first-grip-portion cavity 810, intermediate-portion cavity 814, and second-grip-portion cavity 812 to facilitate formation of monolithic precursor test coupon 100 in mold 800 with reduced or eliminated voids, and further with reduced or eliminated shearing of binder 749 that is included in feedstock material 750 along with metal powder 748. More specifically, runner cavities 830 enable a portion of feedstock material 750 to bypass a flow restriction, caused by intermediate-portion cavity 814 and provide back-fill of downstream portions of monolithic precursor test coupon 100 (shown in FIG. 1A). The bypass flow area provided by runner cavities 830 thus enables formation of monolithic precursor test coupon 100 having a proper distribution and integrity of feedstock material 750 at an injection rate that avoids problems of binder shearing or premature binder cross-linking. Removal of runners 130 from monolithic precursor test coupon 100 leaves first grip portion 110, intermediate portion 114, and second grip portion 112 of test coupon 900 for material property testing, such as in a tensile-test machine (not shown).

Referring generally to FIGS. 11A-11C and particularly to, e.g., FIGS. 7, 8A, 8B, 8E, and 8F, according to method 1100, (block 1118) injecting feedstock material 750 into mold cavity 808 comprises (block 1120) pressurizing feedstock material 750 in barrel 702. Feedstock material 750 is forced from barrel 702, through injection port 802 of mold 800, into first-grip-portion cavity 810 and then from first-grip-portion cavity 810, in parallel through intermediate-portion cavity 814 and runner cavities 830, into second-grip-portion cavity 812. The preceding subject matter of this paragraph characterizes example 66 of the present disclosure, wherein example 66 also includes the subject matter according to example 65, above.

Barrel 702 provides a suitable supply structure in which to pressurize feedstock material 750 to cause injection of feedstock material 750 into mold cavity 808. For example, barrel 702 is in flow communication with hopper 718. Feedstock material 750 is gravity-fed into hopper 718 and flows into barrel 702. After a suitable initial fill of barrel 702 with feedstock material 750, feedstock material 750 is pressurized to cause injection of feedstock material 750 into mold cavity 808. Runner cavities 830 provide flow paths for feedstock material 750 that is injected in parallel to intermediate-portion cavity 814 to facilitate back-fill of downstream portions of monolithic precursor test coupon 100 (shown in FIG. 1A).

Referring generally to FIGS. 11A-11C and particularly to, e.g., FIG. 7, according to method 1100, (block 1120) pressurizing feedstock material 750 in barrel 702 comprises (block 1122) applying hydraulic pressure to feedstock material 750. The preceding subject matter of this paragraph characterizes example 67 of the present disclosure, wherein example 67 also includes the subject matter according to example 66, above.

Hydraulic pressurization provides a suitably controllable pressurization mechanism to inject feedstock material 750. For example, piston head 706 is located within cylinder 710 and is translatable toward barrel 702 in response to receipt of pressurized fluid 708 (e.g., hydraulic fluid or water) in cylinder 710. Piston rod 704, extending from piston head 706 out of cylinder 710 into barrel 702, is shaped to force feedstock material 750 from barrel 702 through injection port 802 in response to the hydraulically pressurized translation of piston head 706 toward barrel 702.

Referring generally to FIGS. 11A-11C and particularly to, e.g., FIG. 7, method 1100 further comprises (block 1104) heating feedstock material 750 before (block 1118) injecting feedstock material 750 into mold cavity 808. The preceding subject matter of this paragraph characterizes example 68 of the present disclosure, wherein example 68 also includes the subject matter according to example 66 or 67, above.

Heating feedstock material 750 before injecting feedstock material 750 into mold cavity 808 facilitates having feedstock material 750 within a temperature range that is sufficiently high to enable suitable flow of feedstock material 750 through mold cavity 808, yet not sufficiently high to melt binder 749 out of feedstock material 750 and not sufficiently high to cross-link and solidify binder 749 prior to adequate fill of mold cavity 808.

Referring generally to FIGS. 11A-11C and particularly to, e.g., FIG. 7, method 1100 further comprises (block 1102) receiving feedstock material 750 in barrel 702. Method 1100 also comprises, before (block 1118) injecting feedstock material 750 into mold cavity 808, (block 1106) advancing feedstock material 750 through barrel 702 toward mold 800. Feedstock material 750 is compacted adjacent to mold 800. The preceding subject matter of this paragraph characterizes example 69 of the present disclosure, wherein example 69 also includes the subject matter according to any one of examples 65 to 68, above.

Advancing feedstock material 750 through barrel 702 to compact feedstock material 750 adjacent to mold 800 reduces air pockets in, and increases homogeneity of, feedstock material 750 before injection of feedstock material 750 into mold cavity 808. For example, screw 711 positioned within barrel 702 advances feedstock material 750 received from hopper 718 toward, and compacts feedstock material 750 adjacent to, mold 800.

Referring generally to FIGS. 11A-11C and particularly to, e.g., FIG. 7, method 1100 further comprises (block 1108) heating mold 800 before (block 1118) injecting feedstock material 750 into mold cavity 808. The preceding subject matter of this paragraph characterizes example 70 of the present disclosure, wherein example 70 also includes the subject matter according to any one of examples 65 to 69, above.

Heating mold 800 facilitates maintaining feedstock material 750 during injection within the temperature range that is sufficiently high to enable suitable flow of feedstock material 750 through mold cavity 808, yet not sufficiently high to melt binder 749 out of feedstock material 750 and not sufficiently high to cross-link and solidify binder 749 prior to adequate fill of mold cavity 808. For example, mold 800 is heated to a temperature that, during injection, maintains feedstock material 750 at approximately the same temperature initially induced by heating feedstock material 750 in barrel 702.

Referring generally to FIGS. 11A-11C and particularly to, e.g., FIGS. 7, 8A, 8B, 8E, and 8F, according to method 1100, (block 1108) heating mold 800 comprises (block 1110) circulating fluid 792 through at least one heat exchanger 790 and through at least one channel 890, defined in mold 800. The preceding subject matter of this paragraph characterizes example 71 of the present disclosure, wherein example 71 also includes the subject matter according to example 70, above.

Circulating fluid 792 through heat exchanger 790 and through at least one channel 890 defined in mold 800 provides a controllable heating mechanism to heat mold 800. For example, at least one channel 890 is implemented as a plurality of channels, with a respective one of at least one channel 890 extending through each of mold sections 860 to facilitate consistent heating among mold sections 860.

Referring generally to FIGS. 11A-11C and particularly to, e.g., FIG. 7, method 1100 further comprises (block 1112) cooling mold 800 after (block 1118) injecting feedstock material 750 into mold cavity 808. The preceding subject matter of this paragraph characterizes example 72 of the present disclosure, wherein example 72 also includes the subject matter according to any one of examples 65 to 71, above.

Cooling mold 800, after injection of feedstock material 750 is complete, facilitates cooling feedstock material 750 within mold cavity 808 to facilitate removal of monolithic precursor test coupon 100 from mold cavity 808. For example, cooling of feedstock material 750 facilitates handling of monolithic precursor test coupon 100 after formation in mold 800, and also tends to cause monolithic precursor test coupon 100 to shrink, which facilitates separation of monolithic precursor test coupon 100 from mold cavity wall 866.

Referring generally to FIGS. 11A-11C and particularly to, e.g., FIGS. 7, 8A, 8B, 8E, and 8F, according to method 1100, (block 1112) cooling mold 800 comprises (block 1114) circulating fluid 792 through at least one heat exchanger 790 and through at least one channel 890, defined in mold 800. The preceding subject matter of this paragraph characterizes example 73 of the present disclosure, wherein example 73 also includes the subject matter according to example 72, above.

Circulating fluid 792 through heat exchanger 790 and through at least one channel 890 defined in mold 800 provides a controllable cooling mechanism to cool mold 800. For example, at least one channel 890 is implemented as a plurality of channels, with a respective one of at least one channel 890 extending through each of mold sections 860 to facilitate consistent cooling among mold sections 860.

Referring generally to FIGS. 11A-11C and particularly to, e.g., FIGS. 7, 8A, 8B, 8E, and 8F, according to method 1100, (block 1118) injecting feedstock material 750 into mold cavity 808 comprises (block 1126) forcing a portion of feedstock material 750 out of mold cavity 808 into sacrificial cavity 840 in downstream flow communication with mold cavity 808. The preceding subject matter of this paragraph characterizes example 74 of the present disclosure, wherein example 74 also includes the subject matter according to any one of examples 65 to 73, above.

Forcing a portion of feedstock material 750 out of mold cavity 808 into sacrificial cavity 840 enables impurities and/or air initially present in mold cavity 808 and/or feedstock material 750 to be expelled from mold cavity 808 at a downstream location as an additional amount of feedstock material 750 continues to be injected into mold cavity 808 at an upstream location. For example, feedstock material 750 may initially be at a temperature that partially melts binder 749 out of feedstock material 750, which would undesirably alter a material property of monolithic precursor test coupon 100. The initial portion of feedstock material 750 is forced through mold cavity 808 into sacrificial cavity 840 as the temperature of feedstock material 750 is adjusted, enabling mold cavity 808 to be filled with feedstock material 750 having reduced or eliminated melt-out of binder 749. In some examples, sacrificial cavity 840 has downstream end 842 open, and feedstock material 750 flowing through downstream end 842 is observed to determine whether adjustment of, e.g., the temperature of feedstock material 750 in barrel 702 and/or other parameters that affect a quality of feedstock material 750, is needed.

Referring generally to FIGS. 11A-11C and particularly to, e.g., FIGS. 7 and 8A-8F, method 1100 further comprises, after (block 1118) injecting feedstock material 750 into mold cavity 808, (block 1130) separating mold sections 860 of mold 800 along at least one of parting surfaces 870 and (block 1132) extending ejector pin 850 from at least one of mold sections 860 into mold cavity 808, such that monolithic precursor test coupon 100 separates from mold 800. The preceding subject matter of this paragraph characterizes example 75 of the present disclosure, wherein example 75 also includes the subject matter according to any one of examples 65 to 74, above.

Extending ejector pin 850 into mold cavity 808 facilitates separating monolithic precursor test coupon 100 from mold sections 860 after mold sections 860 are disassembled for removal of monolithic precursor test coupon 100. More specifically, extending ejector pin 850 into mold cavity 808 pushes monolithic precursor test coupon 100 away from mold cavity wall 866.

Referring generally to FIGS. 11A-11C and particularly to, e.g., FIG. 8D, method 1100 further comprises (block 1116) positioning, before (block 1118) injecting feedstock material 750 into mold cavity 808, ejector pin 850 in a recessed position, such that during (block 1118) injecting feedstock material 750 into mold cavity 808, tapered lower surface 854 of pin head 852 of ejector pin 850 is in direct sealing contact with tapered portion 864 of pin chamber 862 in which ejector pin 850 is seated. The preceding subject matter of this paragraph characterizes example 76 of the present disclosure, wherein example 76 also includes the subject matter according to example 75, above.

Tapered lower surface 854 of pin head 852 being in direct sealing contact with tapered portion 864 of pin chamber 862 facilitates creating a positive seal between pin head 852 and mold cavity wall 866 during injection of feedstock material 750. More specifically, with ejector pin 850 in the recessed position, positive pressure inside mold cavity 808 reacts against pin head 852 and tends to force ejector pin 850 deeper into pin chamber 862, such that the greater the pressure inside mold cavity 808, the better the seal created between tapered lower surface 854 and tapered portion 864 of pin chamber 862. Accordingly, tapered portion 864 of pin chamber 862 tends to reduce or eliminate a potential for ejector pin 850 to become adhered in the recessed position, and thus inoperable to eject monolithic precursor test coupon 100, due to binder 749 seeping between pin head 852 and mold cavity wall 866.

Referring generally to FIGS. 11A-11C and particularly to, e.g., FIGS. 2A-2C and 7, feedstock material 750 further comprises binder 749, and, according to method 1100, (block 1118) injecting feedstock material 750 into mold cavity 808 comprises (block 1128) forming monolithic precursor test coupon 100 in a green state. Method 1100 further comprises (block 1138) de-binding monolithic precursor test coupon 100 from the green state to a brown state. The preceding subject matter of this paragraph characterizes example 77 of the present disclosure, wherein example 77 also includes the subject matter according to any one of examples 65 to 76, above.

De-binding monolithic precursor test coupon 100 from the green state to the brown state facilitates eventual production of test coupon 900 (shown in FIG. 9) having desired material properties. For example, monolithic precursor test coupon 100 is subjected to a suitable thermal or solvent-based process to remove binder 749.

Referring generally to FIGS. 11A-11C and particularly to, e.g., FIGS. 2A-2C and 9, according to method 1100, (block 1142) removing runners 130 is performed before (block 1138) de-binding monolithic precursor test coupon 100 from the green state to the brown state. The preceding subject matter of this paragraph characterizes example 78 of the present disclosure, wherein example 78 also includes the subject matter according to example 77, above.

Removing runners 130 before de-binding simplifies removal of runners 130 from monolithic precursor test coupon 100 due to a lack of structural strength of monolithic precursor test coupon 100 in the green state as compared to the finished material state.

Referring to FIGS. 11A-11C and particularly to, e.g., FIGS. 2A-2C and 9, according to method 1100, (block 1142) removing runners 130 is performed after (block 1138) de-binding monolithic precursor test coupon 100 from the green state to the brown state. The preceding subject matter of this paragraph characterizes example 79 of the present disclosure, wherein example 79 also includes the subject matter according to example 77, above.

Removing runners 130 after de-binding facilitates maintaining a structural integrity of monolithic precursor test coupon 100 during the de-binding process. More specifically, runners 130 interconnecting first grip portion 110 and second grip portion 112 increase a structural stability of first grip portion 110, second grip portion 112, and intermediate portion 114, thereby inhibiting breakage or warping of first grip portion 110, second grip portion 112, and intermediate portion 114 during and after de-binding.

Referring to FIGS. 11A-11C and particularly to, e.g., FIGS. 2A-2C and 9, method 1100 further comprises (block 1140) sintering monolithic precursor test coupon 100 from the brown state to a finished material state. The preceding subject matter of this paragraph characterizes example 80 of the present disclosure, wherein example 80 also includes the subject matter according to any one of examples 77 to 79, above.

Sintering monolithic precursor test coupon 100 from the brown state to the finished material state facilitates production of test coupon 900 (shown in FIG. 9) having desired material properties. For example, monolithic precursor test coupon 100 is subjected to a temperature greater than 1100 degrees Celsius (2012 degrees Fahrenheit) in a suitable vacuum or other non-oxidizing atmosphere. In the finished material state, metal powder 748 originally included in feedstock material 750 and retained in substance 150 has been transformed into post-sintered metal 950.

Referring to FIGS. 11A-11C and particularly to, e.g., FIGS. 2A-2C and 9, according to method 1100, (block 1142) removing runners 130 is performed before (block 1140) sintering monolithic precursor test coupon 100 from the brown state to the finished material state. The preceding subject matter of this paragraph characterizes example 81 of the present disclosure, wherein example 81 also includes the subject matter according to example 80, above.

Removing runners 130 before sintering simplifies removal of runners 130 from monolithic precursor test coupon 100 due to a lack of structural strength of monolithic precursor test coupon 100 in the brown state as compared to the finished material state.

Referring generally to FIGS. 11A-11C and particularly to, e.g., FIGS. 2A-2C and 9, according to method 1100, (block 1142) removing runners 130 is performed after (block 1140) sintering monolithic precursor test coupon 100 from the brown state to the finished material state. The preceding subject matter of this paragraph characterizes example 82 of the present disclosure, wherein example 82 also includes the subject matter according to example 80, above.

Removing runners 130 after sintering facilitates maintaining a structural integrity of monolithic precursor test coupon 100 during the sintering process. More specifically, runners 130 interconnecting first grip portion 110 and second grip portion 112 increase a structural stability of first grip portion 110, second grip portion 112, and intermediate portion 114, thereby inhibiting breakage or warping of first grip portion 110, second grip portion 112, and intermediate portion 114 during and after sintering (e.g., during a cool-down process after sintering).

Referring generally to FIGS. 11A-11C and particularly to, e.g., FIGS. 7, 8A, 8B, 8E, and 8F, first-grip-portion cavity 810, intermediate-portion cavity 814, and second-grip-portion cavity 812 are arranged in series along longitudinal mold-cavity axis 806. Intermediate-portion cavity 814 comprises gauge-portion cavity 820, which defines a gauge cross-sectional flow area, perpendicular to longitudinal mold-cavity axis 806. The gauge cross-sectional flow area is a least value of a set of cross-sectional flow areas, perpendicular to longitudinal mold-cavity axis 806 at all locations along first-grip-portion cavity 810, intermediate-portion cavity 814, and second-grip-portion cavity 812. According to method 1100, (block 1118) injecting feedstock material 750 into mold cavity 808 comprises (block 1124) flowing feedstock material 750 simultaneously through a first flow path, from first-grip-portion cavity 810, through intermediate-portion cavity 814, and into second-grip-portion cavity 812, and through second flow paths, arranged in parallel to the first flow path and each other, from first-grip-portion cavity 810, through runner cavities 830, and into second-grip-portion cavity 812. The preceding subject matter of this paragraph characterizes example 83 of the present disclosure, wherein example 83 also includes the subject matter according to any one of examples 65 to 82, above.

Runner cavities 830 enable a portion of feedstock material 750 to bypass a flow restriction, caused by the gauge cross-sectional flow area being the least value of the set of cross-sectional flow areas, perpendicular to longitudinal mold-cavity axis 806. More specifically, the plurality of second flow paths in parallel to the first flow path through gauge-portion cavity 820 and each other provide back-fill of downstream portions of monolithic precursor test coupon 100 (shown in FIG. 1A). The bypass flow area provided by runner cavities 830 thus enables formation of monolithic precursor test coupon 100 having a proper distribution and integrity of feedstock material 750 at an injection rate that avoids problems of binder shearing or premature binder cross-linking.

Referring generally to FIGS. 12A-12D and particularly to, e.g., FIGS. 10A-10E, method 1200 of removing flash 180 from gauge portion 120 of monolithic precursor test coupon 100 using flash-removal tool 1000 is disclosed. Flash-removal tool 1000 comprises tool body 1002, extending along longitudinal tool axis 1004. Flash-removal tool 1000 also comprises tooth 1010 and engagement surface 1020, spaced apart from tooth 1010 along longitudinal tool axis 1004. Tooth 1010 projects from tool body 1002 in first direction 1090 and comprises shearing surface 1014, facing in first direction 1090 and located offset distance 1012 away from longitudinal tool axis 1004 in second direction 1092. First direction 1090 and second direction 1092 are orthogonal to each other and define a plane, perpendicular to longitudinal tool axis 1004. Method 1200 comprises (block 1210) coupling engagement surface 1020 of flash-removal tool 1000 against first precursor-coupon end 102 of monolithic precursor test coupon 100. Method 1200 also comprises (block 1214) orienting longitudinal tool axis 1004 parallel to longitudinal symmetry axis 106 of monolithic precursor test coupon 100. Shearing surface 1014 registers longitudinally with flash 180. Method 1200 further comprises (block 1236) shearing, using shearing surface 1014, flash 180 from gauge portion 120. The preceding subject matter of this paragraph characterizes example 84 of the present disclosure.

Tooth 1010 projecting from tool body 1002 in first direction 1090 and having shearing surface 1014, located offset distance 1012 away from longitudinal tool axis 1004 in second direction 1092, such that shearing surface 1014 registers longitudinally with flash 180 when engagement surface 1020 of flash-removal tool 1000 couples against first precursor-coupon end 102 and longitudinal tool axis 1004 is oriented parallel to longitudinal symmetry axis 106 of monolithic precursor test coupon 100, facilitates removal of flash 180 from gauge portion 120 at an increased speed, without requiring complex alignment procedures or adjustments. For example, as shown in FIG. 10E, gauge portion 120 has a circular cross-section and a radius 118, and offset distance 1012 equals radius 118 plus tolerance 1016.

Referring generally to FIGS. 12A-12D and particularly to, e.g., FIG. 10E, according to method 1200, (block 1214) orienting longitudinal tool axis 1004 parallel to longitudinal symmetry axis 106 of monolithic precursor test coupon 100 comprises (block 1216) positioning shearing surface 1014 at radial distance 119 from longitudinal symmetry axis 106. Flash 180 projects radially from surface 116 of gauge portion 120 through radial distance 119. The preceding subject matter of this paragraph characterizes example 85 of the present disclosure, wherein example 85 also includes the subject matter according to example 84, above.

Positioning shearing surface 1014 at radial distance 119 from longitudinal symmetry axis 106 enables shearing surface 1014 to register with flash 180 projecting from surface 116, without requiring complex alignment procedures or adjustments beyond coupling engagement surface 1020 to monolithic precursor test coupon 100 and orienting longitudinal tool axis 1004 parallel to longitudinal symmetry axis 106 of monolithic precursor test coupon 100.

Referring generally to FIGS. 12A-12D and particularly to, e.g., FIGS. 10C and 10D, monolithic precursor test coupon 100 further comprises first grip portion 110, second grip portion 112, and intermediate portion 114, interconnecting first grip portion 110 and second grip portion 112. Monolithic precursor test coupon 100 also comprises runners 130, directly interconnecting first grip portion 110 and second grip portion 112 and not directly connected to intermediate portion 114. Intermediate portion 114 of monolithic precursor test coupon 100 comprises gauge portion 120. The preceding subject matter of this paragraph characterizes example 86 of the present disclosure, wherein example 86 also includes the subject matter according to example 84 or 85, above.

Coupling engagement surface 1020 to monolithic precursor test coupon 100 and orienting longitudinal tool axis 1004 parallel to longitudinal symmetry axis 106 of monolithic precursor test coupon 100 enables tooth 1010 to slide between runners 130 of monolithic precursor test coupon 100 such that shearing surface 1014 aligns precisely with flash 180 on gauge portion 120.

Referring generally to FIGS. 12A-12D and particularly to, e.g., FIGS. 10C and 10D, method 1200 further comprises (block 1209) inserting tool body 1002 between two of runners 130. The preceding subject matter of this paragraph characterizes example 87 of the present disclosure, wherein example 87 also includes the subject matter according to example 86, above.

Inserting tool body 1002 between two of runners 130 enables tooth 1010 to slide between runners 130 of monolithic precursor test coupon 100 such that shearing surface 1014 aligns precisely with flash 180 on gauge portion 120.

Referring generally to FIGS. 12A-12D and particularly to, e.g., FIGS. 10D and 10E, according to method 1200, (block 1214) orienting longitudinal tool axis 1004 parallel to longitudinal symmetry axis 106 of monolithic precursor test coupon 100 comprises (block 1218) circumferentially spacing shearing surface 1014 away from flash 180, and (block 1236) shearing flash 180 comprises (block 1238) rotating tool body 1002 about longitudinal symmetry axis 106 such that shearing surface 1014 moves circumferentially toward, and contacts, flash 180. The preceding subject matter of this paragraph characterizes example 88 of the present disclosure, wherein example 88 also includes the subject matter according to example 86 or 87, above.

Circumferentially spacing shearing surface 1014 away from flash 180 (as shown in position 1001 in FIG. 10E), and then rotating tool body 1002 about longitudinal symmetry axis 106 (as indicated by the large curved arrow in FIG. 10D) such that shearing surface 1014 moves circumferentially toward, and contacts, flash 180 (as shown in position 1003 in FIG. 10E), enables flash-removal tool 1000 to be inserted between a pair of runners 130 and used to remove flash 180 without interference between tool body 1002 and runners 130.

Referring generally to FIGS. 12A-12D and particularly to, e.g., FIGS. 10D and 10E, flash 180 has portions each radially aligned with a respective one of runners 130, and, according to method 1200, (block 1238) rotating tool body 1002 comprises (block 1240) shearing one of the portions of flash 180 before tool body 1002 contacts the respective one of runners 130. The preceding subject matter of this paragraph characterizes example 89 of the present disclosure, wherein example 89 also includes the subject matter according to example 88, above.

Rotating tool body 1002 to shear one of the portions of flash 180 before tool body 1002 contacts the respective one of runners 130 enables flash-removal tool 1000 to be used to remove flash 180 radially aligned with runners 130. For example, mold 800 includes runner cavities 830 defined between respective pairs of mold sections 860 (shown in FIGS. 8A, 8B, 8E, and 8F), which reduces or eliminates interference of runners 130, formed in runner cavities 830, with mold sections 860 during disassembly of mold sections 860. This placement of runner cavities 830 causes portions of flash 180, formed by seepage of feedstock material 750 between parting surfaces 870 of mold sections 860, to be formed in radial alignment with each runner 130, with respect to radial direction 132. Radial direction 132 is defined with respect to a cross section of intermediate portion 114 taken along longitudinal symmetry axis 106, as shown in FIG. 10E. For example, tooth 1010 projecting from tool body 1002 in first direction 1090, and having shearing surface 1014, located offset distance 1012 away from longitudinal tool axis 1004 in second direction 1092, enables tooth 1010 to slide between runners 130 such that, when tool body 1002 is inserted between runners 130, shearing surface 1014 is contactable against flash 180 under one of runners 130.

Referring generally to FIGS. 12A-12D and particularly to, e.g., FIGS. 10C and 10D, flash-removal tool 1000 further comprises positioning groove 1006 defined in tool body 1002, positioning groove 1006 extending longitudinally between engagement surface 1020 and tooth 1010. According to method 1200, (block 1214) orienting longitudinal tool axis 1004 parallel to longitudinal symmetry axis 106 of monolithic precursor test coupon 100 comprises (block 1222) receiving a portion of monolithic precursor test coupon 100 in positioning groove 1006. The preceding subject matter of this paragraph characterizes example 90 of the present disclosure, wherein example 90 also includes the subject matter according to any one of examples 84 to 89, above.

Receiving a portion of monolithic precursor test coupon 100 in positioning groove 1006 facilitates stable positioning of flash-removal tool 1000 against monolithic precursor test coupon 100.

Referring generally to FIGS. 12A-12D and particularly to, e.g., FIGS. 10C and 10D, according to method 1200, (block 1210) coupling engagement surface 1020 of flash-removal tool 1000 against first precursor-coupon end 102 comprises (block 1212) coupling longitudinal end-wall 1034 of positioning groove 1006 against first precursor-coupon end 102 of monolithic precursor test coupon 100. The preceding subject matter of this paragraph characterizes example 91 of the present disclosure, wherein example 91 also includes the subject matter according to example 90, above.

Coupling engagement surface 1020 against first precursor-coupon end 102 by coupling longitudinal end-wall 1034 of positioning groove 1006 against first precursor-coupon end 102 combines the step for longitudinally positioning tooth 1010 with an additional step for stable positioning of flash-removal tool 1000 against monolithic precursor test coupon 100, facilitating faster performance of method 1200.

Referring generally to FIGS. 12A-12D and particularly to, e.g., FIGS. 10C and 10D, monolithic precursor test coupon 100 further comprises first grip portion 110, second grip portion 112, and intermediate portion 114, interconnecting first grip portion 110 and second grip portion 112. Intermediate portion 114 comprises gauge portion 120, and positioning groove 1006 comprises cylindrically contoured portion 1030, extending parallel to longitudinal tool axis 1004. According to method 1200, (block 1222) receiving the portion of monolithic precursor test coupon 100 in positioning groove 1006 comprises (block 1224) coupling cylindrically contoured portion 1030 of positioning groove 1006 against first grip portion 110. The preceding subject matter of this paragraph characterizes example 92 of the present disclosure, wherein example 92 also includes the subject matter according to example 90 or 91, above.

Coupling cylindrically contoured portion 1030 of positioning groove 1006 against first grip portion 110 facilitates stable positioning of flash-removal tool 1000 against monolithic precursor test coupon 100 for implementations in which first grip portion 110 has a cylindrical profile complementary to cylindrically contoured portion 1030.

Referring generally to FIGS. 12A-12D and particularly to, e.g., FIGS. 10C and 10D, positioning groove 1006 further comprises tapered portion 1032, parallel to longitudinal tool axis 1004 and extending longitudinally between cylindrically contoured portion 1030 and tooth 1010. According to method 1200, (block 1222) receiving the portion of monolithic precursor test coupon 100 in positioning groove 1006 further comprises (block 1226) coupling tapered portion 1032 of positioning groove 1006 against intermediate portion 114. The preceding subject matter of this paragraph characterizes example 93 of the present disclosure, wherein example 93 also includes the subject matter according to example 92, above.

Coupling tapered portion 1032 of positioning groove 1006 against intermediate portion 114 facilitates stable positioning of flash-removal tool 1000 against monolithic precursor test coupon 100 for implementations in which intermediate portion 114, adjacent to first grip portion 110, has a longitudinally tapering profile complementary to tapered portion 1032.

Referring generally to FIGS. 12A-12D and particularly to, e.g., FIGS. 10C and 10D, flash-removal tool 1000 further comprises secondary groove 1035, defined in tool body 1002. Tooth 1010 divides tool body 1002 longitudinally into two sides. Positioning groove 1006 extends longitudinally on one of the two sides, and secondary groove 1035 extends longitudinally on another of the two sides and faces in first direction 1090. According to method 1200, (block 1214) orienting longitudinal tool axis 1004 parallel to longitudinal symmetry axis 106 of monolithic precursor test coupon 100 further comprises (block 1230) receiving an additional portion of monolithic precursor test coupon 100 in secondary groove 1035. The preceding subject matter of this paragraph characterizes example 94 of the present disclosure, wherein example 94 also includes the subject matter according to any one of examples 90 to 93, above.

Receiving another portion of monolithic precursor test coupon 100 in secondary groove 1035 further facilitates stable positioning of flash-removal tool 1000 against monolithic precursor test coupon 100.

Referring generally to FIGS. 12A-12D and particularly to, e.g., FIGS. 10C and 10D, monolithic precursor test coupon 100 further comprises first grip portion 110, second grip portion 112, and intermediate portion 114, interconnecting first grip portion 110 and second grip portion 112. Secondary groove 1035 comprises cylindrically contoured secondary portion 1036, extending parallel to longitudinal tool axis 1004. According to method 1200, (block 1230) receiving the additional portion of monolithic precursor test coupon 100 in secondary groove 1035 comprises (block 1232) coupling cylindrically contoured secondary portion 1036 of secondary groove 1035 against second grip portion 112. The preceding subject matter of this paragraph characterizes example 95 of the present disclosure, wherein example 95 also includes the subject matter according to example 94, above.

Coupling cylindrically contoured secondary portion 1036 of secondary groove 1035 against second grip portion 112 further facilitates stable positioning of flash-removal tool 1000 against monolithic precursor test coupon 100 for implementations in which second grip portion 112 has a cylindrical profile complementary to cylindrically contoured secondary portion 1036.

Referring generally to FIGS. 12A-12D and particularly to, e.g., FIGS. 10C and 10D, secondary groove 1035 further comprises tapered secondary portion 1038, parallel to longitudinal tool axis 1004 and extending longitudinally between cylindrically contoured secondary portion 1036 and tooth 1010. According to method 1200, (block 1230) receiving the additional portion of monolithic precursor test coupon 100 in secondary groove 1035 further comprises (block 1234) coupling tapered secondary portion 1038 of secondary groove 1035 against intermediate portion 114. The preceding subject matter of this paragraph characterizes example 96 of the present disclosure, wherein example 96 also includes the subject matter according to example 95, above.

Coupling tapered secondary portion 1038 of secondary groove 1035 against intermediate portion 114 further facilitates stable positioning of flash-removal tool 1000 against monolithic precursor test coupon 100 for implementations in which intermediate portion 114, adjacent to second grip portion 112, has a longitudinally tapering profile complementary to tapered secondary portion 1038.

Referring generally to FIGS. 12A-12D and particularly to, e.g., FIG. 10E, according to method 1200, (block 1222) receiving the portion of monolithic precursor test coupon 100 in positioning groove 1006 comprises (block 1228) maintaining gap 1018 between tool body 1002 of flash-removal tool 1000 and gauge portion 120. The preceding subject matter of this paragraph characterizes example 97 of the present disclosure, wherein example 97 also includes the subject matter according to any one of examples 90 to 96, above.

Maintaining gap 1018 between tool body 1002 of flash-removal tool 1000 and gauge portion 120 facilitates reducing or eliminating damage or marring, during removal of flash 180, to gauge portion 120 of monolithic precursor test coupon 100. Integrity of gauge portion 120 is necessary to enable accurate determination of material properties from testing of test coupon 900 (shown in FIG. 9) subsequently formed from monolithic precursor test coupon 100. For example, a depth of positioning groove 1006 and, in some examples, a depth of secondary groove 1035, is selected to create gap 1018 when first grip portion 110 is received in positioning groove 1006 and second grip portion 112 is received in secondary groove 1035.

Referring generally to FIGS. 12A-12D and particularly to, e.g., FIGS. 10C and 10D, engagement surface 1020 is located preselected distance 1022 away from tooth 1010 along longitudinal tool axis 1004. According to method 1200, (block 1214) orienting longitudinal tool axis 1004 parallel to longitudinal symmetry axis 106 of monolithic precursor test coupon 100 comprises (block 1220) aligning shearing surface 1014 longitudinally with gauge portion 120. The preceding subject matter of this paragraph characterizes example 98 of the present disclosure, wherein example 98 also includes the subject matter according to any one of examples 84 to 97, above.

Engagement surface 1020 being located preselected distance 1022 away from tooth 1010 along longitudinal axis 1004 enables shearing surface 1014 to align longitudinally with gauge portion 120 when engagement surface 1020 engages monolithic precursor test coupon 100 and longitudinal tool axis 1004 is aligned with longitudinal symmetry axis 106.

Referring generally to FIGS. 12A-12D and particularly to, e.g., FIGS. 10A and 10C, method 1200 further comprises (block 1202) adjusting preselected distance 1022 before (block 1214) orienting longitudinal tool axis 1004 parallel to longitudinal symmetry axis 106 of monolithic precursor test coupon 100. The preceding subject matter of this paragraph characterizes example 99 of the present disclosure, wherein example 99 also includes the subject matter according to example 98, above.

Adjusting preselected distance 1022 prior to use on monolithic precursor test coupon 100 facilitates an adaptability of flash-removal tool 1000 to monolithic precursor test coupon 100 having various sizes. For example, monolithic precursor test coupon 100 is manufactured in different longitudinal sizes corresponding to different sizes of test coupon 900 needed for use with different material property testing machines (not shown). Preselected distance 1022 being adjustable enables a single tool, such as flash-removal tool 1000, to be used with more than one size of monolithic precursor test coupon 100.

Referring generally to FIGS. 12A-12D and particularly to, e.g., FIG. 10A, flash-removal tool 1000 comprises telescoping portion 1040, coupled to tool body 1002, and engagement surface 1020 is defined on telescoping portion 1040. According to method 1200, (block 1202) adjusting preselected distance 1022 comprises (block 1204) re-positioning telescoping portion 1040 along longitudinal tool axis 1004 with respect to tool body 1002. The preceding subject matter of this paragraph characterizes example 100 of the present disclosure, wherein example 100 also includes the subject matter according to example 99, above.

Re-positioning of telescoping portion 1040 with respect to tool body 1002 provides a mechanically simple implementation for adjusting preselected distance 1022.

Referring generally to FIGS. 12A-12D and particularly to, e.g., FIG. 10A, according to method 1200, (block 1202) adjusting preselected distance 1022 further comprises (block 1206) selectively locking telescoping portion 1040 in position relative to tool body 1002 after (block 1204) re-positioning telescoping portion 1040 along longitudinal tool axis 1004 with respect to tool body 1002. The preceding subject matter of this paragraph characterizes example 101 of the present disclosure, wherein example 101 also includes the subject matter according to example 100, above.

Selectively locking telescoping portion 1040 facilitates a stability and ease of use of flash-removal tool 1000 after adjusting preselected distance 1022.

Referring generally to FIGS. 12A-12D and particularly to, e.g., FIG. 10A, detent 1044 is located on one of telescoping portion 1040 or tool body 1002, and plurality of catches 1046 is arranged longitudinally on another of telescoping portion 1040 or tool body 1002. According to method 1200, (block 1206) selectively locking telescoping portion 1040 in position relative to tool body 1002 comprises (block 1208) moving detent 1044 into interference with one of plurality of catches 1046. The preceding subject matter of this paragraph characterizes example 102 of the present disclosure, wherein example 102 also includes the subject matter according to example 101, above.

Moving detent 1044 into interference with one of catches 1046 corresponding to preselected distance 1022 provides a mechanically simple and effective implementation of locking telescoping portion 1040.

Referring generally to FIGS. 12A-12D and particularly to, e.g., FIGS. 10B AND 10E, monolithic precursor test coupon 100 further comprises first grip portion 110, second grip portion 112, intermediate portion 114, interconnecting first grip portion 110 and second grip portion 112. Monolithic precursor test coupon 100 also comprises runners 130, directly interconnecting first grip portion 110 and second grip portion 112 and not directly connected to intermediate portion 114. Intermediate portion 114 comprises gauge portion 120, and flash 180 has portions each radially aligned with a respective one of runners 130. Flash-removal tool 1000 further comprises second tooth 1011. Longitudinal tool axis 1004 is located between tooth 1010 and second tooth 1011. According to method 1200, (block 1236) shearing flash 180 from gauge portion 120 comprises (block 1242) shearing a first one of the portions of flash 180 with tooth 1010 and a second one of the portions of flash 180 with second tooth 1011. The preceding subject matter of this paragraph characterizes example 103 of the present disclosure, wherein example 103 also includes the subject matter according to any one of examples 84 to 102, above.

Shearing a first one of the portions of flash 180 with tooth 1010 and a second one of the portions of flash 180 with second tooth 1011 facilitates removal of multiple portions of flash 180 without requiring disengagement of flash-removal tool 1000 from monolithic precursor test coupon 100 and subsequent re-positioning of flash-removal tool 1000 to re-position tooth 1010 adjacent to the second portion of flash 180, facilitating increased speed of removal of flash 180 from monolithic precursor test coupon 100.

Referring generally to FIGS. 12A-12D and particularly to, e.g., FIG. 10E, according to method 1200, (block 1236) shearing flash 180 from gauge portion 120 comprises (block 1244) shearing flash 180 from monolithic precursor test coupon 100 that is in a green state. The preceding subject matter of this paragraph characterizes example 104 of the present disclosure, wherein example 104 also includes the subject matter according to any one of examples 84 to 103, above.

Shearing flash 180 from monolithic precursor test coupon 100 in the green state simplifies removal of flash 180 from monolithic precursor test coupon 100 due to a lack of structural strength of monolithic precursor test coupon 100 in the green state as compared to the finished material state. Monolithic precursor test coupon 100 remains in the green state until subjected to a de-binding process, which results in a transformation to a brown state.

Referring generally to FIGS. 12A-12D and particularly to, e.g., FIG. 10E, according to method 1200, (block 1236) shearing flash 180 from gauge portion 120 comprises (block 1246) shearing flash 180 from monolithic precursor test coupon 100 that is in a brown state. The preceding subject matter of this paragraph characterizes example 105 of the present disclosure, wherein example 105 also includes the subject matter according to any one of examples 84 to 103, above.

Shearing flash 180 from monolithic precursor test coupon 100 in the brown state simplifies removal of flash 180 from monolithic precursor test coupon 100 due to a lack of structural strength of monolithic precursor test coupon 100 in the brown state as compared to the finished material state. After de-binding, monolithic precursor test coupon 100 remains in the brown state until subjected to a sintering process, which results in a transformation to a finished material state.

Referring generally to FIGS. 12A-12D and particularly to, e.g., FIG. 10E, according to method 1200, (block 1236) shearing flash 180 from gauge portion 120 comprises (block 1248) shearing flash 180 from monolithic precursor test coupon 100 that is in a finished material state. The preceding subject matter of this paragraph characterizes example 106 of the present disclosure, wherein example 106 also includes the subject matter according to any one of examples 84 to 103, above.

Shearing flash 180 from monolithic precursor test coupon 100 in the finished material state facilitates reducing or eliminating a risk of damage to gauge portion 120 during removal of flash 180, due to increased structural strength of monolithic precursor test coupon 100 in the finished material state.

Referring generally to FIGS. 12A-12D and particularly to, e.g., FIG. 10E, monolithic precursor test coupon 100 further comprises first grip portion 110, second grip portion 112, and intermediate portion 114, interconnecting first grip portion 110 and second grip portion 112. Monolithic precursor test coupon 100 also comprises runners 130, directly interconnecting first grip portion 110 and second grip portion 112 and not directly connected to intermediate portion 114. Intermediate portion 114 comprises gauge portion 120, and flash 180 has portions each radially aligned with a respective one of runners 130. According to method 1200, (block 1236) shearing flash 180 from gauge portion 120 comprises (block 1250) shearing a first one of the portions of flash 180. The preceding subject matter of this paragraph characterizes example 107 of the present disclosure, wherein example 107 also includes the subject matter according to any one of examples 84 to 106, above.

Shearing a first portion of flash 180 that is radially aligned with one of runners 130 facilitates maintaining runners 130 intact during flash removal, which in turn increases a structural stability of monolithic precursor test coupon 100 during flash removal, particularly for examples in which monolithic precursor test coupon 100 is in a green state or a brown state during flash removal.

Referring generally to FIGS. 12A-12D and particularly to, e.g., FIGS. 10C-10E, method 1200 further comprises, after (block 1250) shearing the first one of the portions of flash 180, (block 1254) removing flash-removal tool 1000 from between a first adjacent pair of runners 130, (block 1256) re-positioning flash-removal tool 1000 between a second adjacent pair of runners 130, and (block 1258) shearing, by shearing surface 1014, a second one of the portions of flash 180 from gauge portion 120. The preceding subject matter of this paragraph characterizes example 108 of the present disclosure, wherein example 108 also includes the subject matter according to example 107, above.

Re-positioning flash-removal tool 1000 between a second adjacent pair of runners 130 and shearing a second portion of the flash that is radially aligned with another of runners 130 facilitates maintaining runners 130 intact during flash removal using flash-removal tool 1000 having a single tooth 1010, which simplifies manufacture and maintenance of flash-removal tool 1000.

Referring generally to FIGS. 12A-12D and particularly to, e.g., FIGS. 9 and 10E, monolithic precursor test coupon 100 further comprises first grip portion 110, second grip portion 112, and intermediate portion 114, interconnecting first grip portion 110 and second grip portion 112. Monolithic precursor test coupon 100 also comprises runners 130, directly interconnecting first grip portion 110 and second grip portion 112 and not directly connected to intermediate portion 114. Intermediate portion 114 of monolithic precursor test coupon 100 comprises gauge portion 120. Method 1200 further comprises (block 1252) removing runners 130 from monolithic precursor test coupon 100. According to method 1200, (block 1236) shearing flash 180 from gauge portion 120 is performed before (block 1252) removing runners 130 from monolithic precursor test coupon 100. The preceding subject matter of this paragraph characterizes example 109 of the present disclosure, wherein example 109 also includes the subject matter according to any one of examples 84 to 108, above.

Shearing flash 180 before removal of runners 130 increases a structural stability of monolithic precursor test coupon 100 during flash removal, particularly for examples in which monolithic precursor test coupon 100 is in a green state or a brown state during flash removal.

Referring generally to FIGS. 12A-12D and particularly to, e.g., FIGS. 9 and 10E, monolithic precursor test coupon 100 further comprises first grip portion 110, second grip portion 112, and intermediate portion 114, interconnecting first grip portion 110 and second grip portion 112. Monolithic precursor test coupon 100 also comprises runners 130, directly interconnecting first grip portion 110 and second grip portion 112 and not directly connected to intermediate portion 114. Intermediate portion 114 of monolithic precursor test coupon 100 comprises gauge portion 120. Method 1200 further comprises (block 1252) removing runners 130 from monolithic precursor test coupon 100. According to method 1200, (block 1236) shearing flash 180 from gauge portion 120 is performed after (block 1252) removing runners 130 from monolithic precursor test coupon 100. The preceding subject matter of this paragraph characterizes example 110 of the present disclosure, wherein example 110 also includes the subject matter according to any one of examples 84 to 108, above.

Shearing flash 180 after removal of runners 130 facilitates reducing or eliminating interference of runners 130 with flash-removal tool 1000, while maintaining ease of alignment, provided by flash-removal tool 1000.

Examples of the present disclosure may be described in the context of aircraft manufacturing and service method 1300 as shown in FIG. 13 and aircraft 1302 as shown in FIG. 14. During pre-production, illustrative method 1300 may include specification and design (block 1304) of aircraft 1302 and material procurement (block 1306). During production, component and subassembly manufacturing (block 1308) and system integration (block 1310) of aircraft 1302 may take place. Thereafter, aircraft 1302 may go through certification and delivery (block 1312) to be placed in service (block 1314). While in service, aircraft 1302 may be scheduled for routine maintenance and service (block 1316). Routine maintenance and service may include modification, reconfiguration, refurbishment, etc. of one or more systems of aircraft 1302.

Each of the processes of illustrative method 1300 may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

As shown in FIG. 14, aircraft 1302 produced by illustrative method 1300 may include airframe 1318 with a plurality of high-level systems 1320 and interior 1322. Examples of high-level systems 1320 include one or more of propulsion system 1324, electrical system 1326, hydraulic system 1328, and environmental system 1330. Any number of other systems may be included. Although an aerospace example is shown, the principles disclosed herein may be applied to other industries, such as the automotive industry. Accordingly, in addition to aircraft 1302, the principles disclosed herein may apply to other vehicles, e.g., land vehicles, marine vehicles, space vehicles, etc.

Apparatus(es) and method(s) shown or described herein may be employed during any one or more of the stages of the manufacturing and service method 1300. For example, components or subassemblies corresponding to component and subassembly manufacturing (block 1308) may be fabricated or manufactured in a manner similar to components or subassemblies produced while aircraft 1302 is in service (block 1314). Also, one or more examples of the apparatus (es), method(s), or combination thereof may be utilized during production stages 1308 and 1310, for example, by substantially expediting assembly of or reducing the cost of aircraft 1302. Similarly, one or more examples of the apparatus or method realizations, or a combination thereof, may be utilized, for example and without limitation, while aircraft 1302 is in service (block 1314) and/or during maintenance and service (block 1316).

Different examples of the apparatus(es) and method(s) disclosed herein include a variety of components, features, and functionalities. It should be understood that the various examples of the apparatus(es) and method(s) disclosed herein may include any of the components, features, and functionalities of any of the other examples of the apparatus (es) and method(s) disclosed herein in any combination, and all of such possibilities are intended to be within the scope of the present disclosure.

Many modifications of examples set forth herein will come to mind to one skilled in the art to which the present disclosure pertains having the benefit of the teachings presented in the foregoing descriptions and the associated drawings.

Therefore, it is to be understood that the present disclosure is not to be limited to the specific examples illustrated and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims. Accordingly, parenthetical reference numerals in the appended claims are presented for illustrative purposes only and are not intended to limit the scope of the claimed subject matter to the specific examples provided in the present disclosure.

What is claimed is:

1. A method of making a test coupon using a mold, the mold defining a mold cavity that comprises a first-grip-portion cavity, a second-grip-portion cavity, an intermediate-portion cavity, interconnecting the first-grip-portion cavity and the second-grip-portion cavity, and runner cavities, directly interconnecting the first-grip-portion cavity and the second-grip-portion cavity and not directly connected to the intermediate-portion cavity, the method comprising steps of:

injecting feedstock material, comprising a metal powder, into the mold cavity to form a monolithic precursor test coupon in the mold cavity, wherein the monolithic precursor test coupon comprises a first grip portion, having a shape complementary to that of the first-grip-portion cavity, a second grip portion, having a shape complementary to that of the second-grip-portion cavity, an intermediate portion, having a shape complementary to that of the intermediate-portion cavity, and runners, each having a shape complementary to that of a corresponding one of the runner cavities; and removing the runners from the monolithic precursor test coupon.

2. The method according to claim 1, wherein:
the step of injecting the feedstock material into the mold cavity comprises pressurizing the feedstock material in a barrel; and
the feedstock material is forced from the barrel, through an injection port of the mold, into the first-grip-portion cavity, and then from the first-grip-portion cavity, in parallel through the intermediate-portion cavity and the runner cavities, into the second-grip-portion cavity.

3. The method according to claim 2, further comprising, heating the feedstock material before the step of injecting the feedstock material into the mold cavity.

4. The method according to claim 2, wherein the step of pressurizing the feedstock material in the barrel comprises applying hydraulic pressure to the feedstock material.

5. The method according to claim 2, wherein:
the first-grip-portion cavity, the intermediate-portion cavity, and the second-grip-portion cavity are arranged in series along a longitudinal mold-cavity axis;
the intermediate-portion cavity comprises a gauge-portion cavity;
the gauge-portion cavity defines a gauge cross-sectional flow area, perpendicular to the longitudinal mold-cavity axis;
the gauge cross-sectional flow area is a least value of a set of cross-sectional flow areas, perpendicular to the longitudinal mold-cavity axis at all locations along the first-grip-portion cavity, the intermediate-portion cavity, and the second-grip-portion cavity; and
the step of injecting the feedstock material into the mold cavity comprises flowing the feedstock material simultaneously through:
a first flow path, from the first-grip-portion cavity, through the intermediate-portion cavity, and into the second-grip-portion cavity; and
second flow paths, arranged in parallel to the first flow path and each other, from the first-grip-portion cavity, through the runner cavities, and into the second-grip-portion cavity.

6. The method according to claim 1, further comprising: receiving the feedstock material in a barrel; and
before the step of injecting the feedstock material into the mold cavity, advancing the feedstock material through the barrel toward the mold, wherein the feedstock material is compacted adjacent to the mold.

7. The method according to claim 1, further comprising, a step of heating the mold before the step of injecting the feedstock material into the mold cavity.

8. The method according to claim 7, wherein the step of heating the mold comprises circulating a fluid through at least one heat exchanger and through at least one channel, defined in the mold.

9. The method according to claim 1, further comprising a step of cooling the mold after the step of injecting the feedstock material into the mold cavity.

10. The method according to claim 9, wherein the step of cooling the mold comprises circulating a fluid through at least one heat exchanger and through at least one channel, defined in the mold.

11. The method according to claim 1, wherein the step of injecting the feedstock material into the mold cavity comprises forcing a portion of the feedstock material out of the mold cavity into a sacrificial cavity in downstream flow communication with the mold cavity.

12. The method according to claim 1, further comprising, after the step of injecting the feedstock material into the mold cavity:
separating mold sections of the mold along at least one of parting surfaces; and
extending an ejector pin from at least one of the mold sections into the mold cavity such that the monolithic precursor test coupon separates from the mold.

13. The method according to claim 12, further comprising positioning, before the step of injecting the feedstock material into the mold cavity, the ejector pin in a recessed position, such that during the step of injecting the feedstock material into the mold cavity, a tapered lower surface of a pinhead of the ejector pin is in direct sealing contact with a tapered portion of a pin chamber in which the ejector pin is seated.

14. The method according to claim 1, wherein:
the feedstock material further comprises a binder;
the step of injecting the feedstock material into the mold cavity comprises forming the monolithic precursor test coupon in a green state; and
the method further comprises de-binding the monolithic precursor test coupon from the green state to a brown state.

15. The method according to claim 14, wherein the step of removing the runners is performed before the step of de-binding the monolithic precursor test coupon from the green state to the brown state.

16. The method according to claim 14, wherein the step of removing the runners is performed after the step of de-binding the monolithic precursor test coupon from the green state to the brown state.

17. The method according to claim 16, further comprising sintering the monolithic precursor test coupon from the brown state to a finished material state.

18. The method according to claim 17, wherein the step of removing the runners is performed before the step of sintering the monolithic precursor test coupon from the brown state to the finished material state.

19. The method according to claim 17, wherein the step of removing the runners is performed after the step of sintering the monolithic precursor test coupon from the brown state to the finished material state.

20. The method according to claim 1, wherein:
the first-grip-portion cavity, the intermediate-portion cavity, and the second-grip-portion cavity are arranged in series along a longitudinal mold-cavity axis;
the intermediate-portion cavity comprises a gauge-portion cavity;
the gauge-portion cavity defines a gauge cross-sectional flow area, perpendicular to the longitudinal mold-cavity axis;
the gauge cross-sectional flow area is a least value of a set of cross-sectional flow areas, perpendicular to the longitudinal mold-cavity axis at all locations along the first-grip-portion cavity, the intermediate-portion cavity; and the second-grip-portion cavity; and
the step of injecting the feedstock material into the mold cavity comprises flowing the feedstock material simultaneously through:
a first flow path, from the first-grip-portion cavity; through the intermediate-portion cavity, and into the second-grip-portion cavity; and
second flow paths, arranged in parallel to the first flow path and each other, from the first-grip-portion cavity, through the runner cavities, and into the second-grip-portion cavity.

* * * * *